United States Patent
Gronthos et al.

(10) Patent No.: US 10,544,394 B2
(45) Date of Patent: Jan. 28, 2020

(54) METHOD OF INCREASING PROLIFERATION OF BONE MARROW MONONUCLEAR CELLS EXPRESSING STRO1-$^{dim}$

(71) Applicants: Stan Gronthos, Adelaide (AU); Andrew Christopher William Zannettino, Highbury (AU)

(72) Inventors: Stan Gronthos, Adelaide (AU); Andrew Christopher William Zannettino, Highbury (AU)

(73) Assignee: Mesoblast, Inc., New York, NY (US)

( * ) Notice: Subject to any disclaimer, the term of this patent is extended or adjusted under 35 U.S.C. 154(b) by 0 days.

(21) Appl. No.: 14/470,769

(22) Filed: Aug. 27, 2014

(65) Prior Publication Data

US 2015/0072422 A1   Mar. 12, 2015

Related U.S. Application Data

(63) Continuation of application No. 12/924,008, filed on Sep. 16, 2010, now abandoned, which is a continuation of application No. 11/663,570, filed as application No. PCT/AU2005/000953 on Jun. 29, 2005, now abandoned.

(60) Provisional application No. 60/613,021, filed on Sep. 24, 2004.

(51) Int. Cl.
- *C12N 15/00* (2006.01)
- *C12N 5/00* (2006.01)
- *C12N 5/077* (2010.01)

(52) U.S. Cl.
CPC ...... *C12N 5/0652* (2013.01); *C12N 2501/125* (2013.01); *C12N 2501/135* (2013.01); *C12N 2501/22* (2013.01); *C12N 2501/2301* (2013.01); *C12N 2501/2303* (2013.01); *C12N 2501/2306* (2013.01); *C12N 2501/25* (2013.01); *C12N 2501/999* (2013.01); *C12N 2502/13* (2013.01)

(58) Field of Classification Search
CPC ........................................................ C12N 5/00
USPC .................................... 424/93.21; 435/325
See application file for complete search history.

(56) References Cited

U.S. PATENT DOCUMENTS

| | | |
|---|---|---|
| 5,197,985 A | 3/1993 | Caplan et al. |
| 5,226,914 A | 7/1993 | Caplan et al. |
| 5,405,722 A | 1/1995 | Ponting et al. |
| 5,486,359 A | 1/1996 | Caplan et al. |
| 5,580,754 A | 12/1996 | Samal |
| 5,591,625 A | 1/1997 | Gerson et al. |
| 5,811,094 A | 9/1998 | Caplan et al. |
| 5,827,740 A | 10/1998 | Pittenger |
| 5,837,539 A | 11/1998 | Caplan et al. |
| 5,922,597 A | 7/1999 | Verfaille et al. |
| 5,980,887 A | 11/1999 | Isner et al. |
| 6,022,540 A | 2/2000 | Bruder et al. |
| 6,087,113 A | 7/2000 | Caplan et al. |
| 6,261,549 B1 | 7/2001 | Fernandez et al. |
| 6,322,784 B1 | 11/2001 | Pittenger et al. |
| 6,335,195 B1 | 1/2002 | Rodgers et al. |
| 6,387,367 B1 | 5/2002 | Davis-Sproul et al. |
| 6,387,369 B1 | 5/2002 | Pittenger et al. |
| 6,645,727 B2 | 11/2003 | Thomas et al. |
| 6,709,864 B1 | 3/2004 | Pittinger et al. |
| 6,875,430 B2 | 4/2005 | McIntosh et al. |
| 7,122,178 B1 | 10/2006 | Simmons et al. |
| 2002/0085996 A1 | 7/2002 | McIntosh et al. |
| 2004/0107453 A1 | 6/2004 | Furcht et al. |
| 2005/0019911 A1 | 1/2005 | Gronthos et al. |
| 2005/0158289 A1 | 7/2005 | Simmons et al. |
| 2005/0281790 A1 | 12/2005 | Simmons et al. |
| 2006/0008452 A1 | 1/2006 | Simmons et al. |
| 2006/0193840 A1 | 8/2006 | Gronthos et al. |
| 2006/0286077 A1 | 12/2006 | Gronthos et al. |
| 2007/0065938 A1 | 3/2007 | Gronthos et al. |
| 2009/0029912 A1 | 1/2009 | Gronthos et al. |

FOREIGN PATENT DOCUMENTS

| | | | |
|---|---|---|---|
| WO | WO 99/003973 A | | 1/1999 |
| WO | WO 00/06701 | | 2/2000 |
| WO | WO 01/04268 | * | 1/2001 |
| WO | WO 01/04268 A1 | | 1/2001 |
| WO | WO 01/011011 | | 2/2001 |
| WO | WO 02/007679 | | 1/2002 |
| WO | WO 04/84921 A1 | | 10/2004 |
| WO | WO 04/85630 A1 | | 10/2004 |

(Continued)

OTHER PUBLICATIONS

Nigh (Biochem Biophys Res Commun Sep. 2011 vol. 413, No. 2, p. 353-357).*
Lin (Stem Cells and Develop. Oct. 2011, vol. 20, No. 10, p. 1747-1752).*
Lin (Histol Histopathol Sep. 2013 vol. 28, No. 9, p. 1109-1116).*
Andreson (Perfusion, 2002, vol. 17, p. 15-21).*
Description of CD90 on Wikipedia, 2015.*
Definition of CD146, Wikipedia, 2015.*
Gronthos, J. Cell Sci 116:1827-1835, 2003.*

(Continued)

*Primary Examiner* — Michael C Wilson
(74) *Attorney, Agent, or Firm* — John P. White; Gary J. Gershik; Cooper & Dunham LLP

(57) ABSTRACT

The present invention relates to methods of enhancing proliferation and/or survival of mesenchymal precursor cells (MPC) and/or progeny derived therefrom in vitro or in vivo comprising exposing the MPC or progeny to SDF-1 or analog thereof. The invention also relates to compositions comprising isolated MPCs or progeny derived therefrom and SDF-1 or analogues thereof. The present invention also relates to using such methods and compositions for ex vivo or in vivo bone formation in mammals.

2 Claims, 28 Drawing Sheets

Specification includes a Sequence Listing.

(56) References Cited

FOREIGN PATENT DOCUMENTS

| WO | WO 2004/084921 | * | 10/2004 |
| WO | WO 2004/085630 | * | 10/2004 |

OTHER PUBLICATIONS

Shi, JBMR 18(4): 696-704, 2003.*
U.S. Appl. No. 11/663,563, filed Mar. 23, 2007.
Gronthos, S., et al. (2003) "Molecular and Cellular Characterization of Highly Purified Stromal Stem Cells Derived from Human Bone Marrow." J. Cell Sci. 116:9, pp. 1827-1835.
Hellström M, Kalén M, Lindahl P, Abramsson A, and Betsholtz C. (1999) Role of PDGF-B and PDGFR-β in recruitment of vascular smooth muscle cells and pericytes during embryonic blood vessel formation in the mouse. Development 126: 3047-3055.
Jones, E.A. et al (2002) "Isolation and Characterization of Bone Marrow Multipotential Mesenchymal Progenitor Cells" Arthritis & Rheumatism 46(12), pp. 3349-3360.
Shi, S. et al. (2001) "Comparison of Human Dental Pulp and Bone Marrow Stromal Stem Cells by cDNA Microarray Analysis" Bone 29(6), pp. 532-539.
Shi S et al: "Perivascular niche of postnatal mesenchymal stem cells in human bone marrow and dental pulp." Journal of Bone and Mineral Research, vol. 17, No. Suppl 1, Sep. 2002 (Sep. 2002), p. S446, XP009083412 & Twenty-Fourth Annual meeting of the American Society for Bone and Mineral Research; San Antonio, Texas, USA; Sep. 20-24, 2002.
Gronthos S et al: "Postnatal human dental pulp stem cells (DPSCs) in vitro and in vivo." Proceedings of the National Academy of Sciences of USA, National Academy of Science, Washington, DC, US, vol. 97, No. 25, Dec. 5, 2000 (Dec. 5, 2000), pp. 13625-13630.
Shi S et al: "Perivascular niche of postnatal mesenchymal stem cells in human bone marrow and dental pulp." Journal of Bone and Mineral Research, New York, NY, US, vol. 18, No. 4, Apr. 2003 (Apr. 2003), p. 696-704.
Tse H F et al: "Angiogenesis in ischaemic myocardium by intramyocardial autologous bone marrow mononuclear cell implantation." Lancet The, Lancet Limited, London, GB, vol. 361, No. 9351, Jan. 4, 2003 (Jan. 4, 2003), pp. 47-49.
Supplementary European Search Report from European Patent Office, Application No. EP 04 72 3935, dated May 10, 2007.
Supplementary European Search Report from European Patent Office, Application No. EP 04 72 3937, dated May 25, 2007.
International Search Report issued by the International Searching Authority (ISA/AU) dated May 17, 2004 in connection with International Application No. PCT/AU2004/000417.
International Preliminary Report on Patentability issued by the International Bureau of WIPO dated Oct. 1, 2005 in connection with International Application No. PCT/AU2004/000417.
Alberico et al. (1987) Blood 69, p. 1120-1127.
Allen, T.D., (1981) "Haemopoietic Microenvironments in vitro: ultrastructural aspects" CIBA Found. Symposium 84, pp. 38-67.
Allen et al. (1990) "Marrow Biology and Stem Cells" Immunol. Ser. 49, pp. 1-38.
Anklesaria et al. (1989) Blood 74, p. 1144-1151.
Anklesaria et al. (1987) Proc. Nat'l Acad. Sci. USA 84, p. 7681-7685.
Bennett, J.H. et al. (1991) J. Cell Sci. 99, p. 131-139.
Bentley, S.A. (1982) Br. J. Haematol 50(1), pp. 1-6.
Castro-Malaspina et al. (1980) "Characterization of Human Bone Marrow Fibroblast Colony-Forming Cells and Their Progeny" Blood 56, pp. 289-301.
Castro-Malaspina et al. (1981) "Human Megakaryocyte Stimulation of Proliferation of Bone Marrow Fibroblasts" Blood 57, pp. 731-787.
Clarke, Emer, "Mesenchymal Cells" www.stemcell.com (mini-review).
Dexter et al. (1977) "Conditions Controlling the Proliferation of Haemopoietic Stem Cells in Vitro" J. Cell Physiol. 91, pp. 335-344.
Dexter et al. (1984) Kroc Found. Ser. 18, pp. 57-96.
Doherty, M.J. et al. (1998) "Vascular Pericytes Express Osteogenic Potential in Vitro and in Vitro" J. Bone and Mineral Research 13, pp. 828-838.
Fong et al. (1997) "Nonradioactive, Agarose Minigel Procedure for Telomeric Repeat Amplification Protocol" BioTechniques 23, pp. 1029-1032.
Friedenstein (1976) Int'l R. Cytology 47, p. 327.
Friedenstein (1980) "Stromal Mechanisms of Bone Marrow: Cloning in Vitro and Retransplantation in Vivo" Immunology of Bone Marrow Transplantation, pp. 19-29 Haematol. Blood Transfusion.
Friedenstein et al. (1970) "The Development of Fibroblast Colonies in Monolayer Cultures of Guinea-Pig Bone Marrow and Spleen Cells" Cell Tissue Kinetics 3, pp. 393-403.
Friedenstein et al. (1992) Bone and Mineral 18, pp. 199-213.
Gronthos, S. et al. (2002) "Stem Cell Properties of Human Dental Pulp Stem Cells" J. Dent. Res. 81(8), pp. 531-535.
Gronthos, S., et al. (1994) "The STRO-1+ Fraction of Adult Human Bone Marrow Contains the Osteogenic Precursors," Blood 84, pp. 4164-4173.
Gronthos, S., et al. (1995) Blood 85, pp. 929-940.
Huang and Terstappen (1992) Nature 360, pp. 745-749.
Keating et al. (1982) Nature 298, pp. 280-283.
Kim et al. (1994) Science 266, pp. 2011-2015.
Knospe et al. (1966) Blood 28, pp. 398-415.
Knospe et al. (1972) Blood 39, pp. 331-340.
Lichtman (1981) Experimental Hematology 9, pp. 391-410.
Long (1992) Experimental Hematology 20, pp. 288-301.
McManus and Weiss (1984) Blood 64, pp. 1036-1041.
McIntyre and Bjornson (1986) Exp. Hematol. 14, pp. 833- 839.
Miltenyi et al. (1990) Cytometry 11, pp. 231-238.
Owen (1985) Bone and Mineral Research 3, pp. 1-25.
Owen and Friedenstein (1988) CIBA Found. Symposium 136, pp. 42-60.
Perkins and Fleischman (1990) Blood 75, pp. 620-625.
Piersma et al. (1983) Br. J. Haematol. 54, pp. 285-290.
Rothstein et al. (1985) Blood 65, p. 744-752.
Simmons and Gronthos (1991) Int'l J. Cell Cloning 9, p. 408 (abstract).
Simmons, P.J., et al. (1994) "Isolation, Characterization and Functional Activity of Human Marrow Stromal Progenitors in Hemopoiesis" Advances in Bone Marrow Purging and Processing: Progress in Clinical and Biological Research; Fourth Int'l Symposium 389, pp. 271-280.
Simmons et al. (1987) Nature 328, pp. 429-432.
Simmons and Torok-Storb (1991) Blood 78, pp. 55-62.
Simmons and Torok-Storb (1991) Blood 78, pp. 2848-2853.
Tavassoli and Friedenstein (1983) Ann. J. Hematol. 15, pp. 195-203.
Tavassoli and Crosby (1968) Science 161, pp. 54-56.
Testa et al. (1988) "Long-Term Bone Marrow Damage After Cytotoxic Treatment: Stem Cells and Microenvironment in Hematopoiesis: Long-Term Effects of Chemotherapy and Radiation" Hematol. Published by Marcel & Deaker, Inc. 8, pp. 75-91.
Van Vlasselaer et al. (1994) Blood 84, p. 753-763.
Waller et al. (1995) Blood 85, p. 2422-2435.
Weiss (1976) Anatomical Record 186, p. 161-184.
Zóltowska A, Stepiński J, Lewko B, Zamorska B, Roszkiewicz A, Serkies K, and Kruszewski WJ. (2001) Malformations of Angiogenesis in the Low Differentiated Human Carcinomas. Immunohistochemical Study. Arch. Immunol. Ther. Ex. 49: 59-61.
Axelrad et al., New Technologies for the Enhancement of Skeletal Repair, Injury, Int. J. Care Injured (2007) 38S1:S49-S62.
Bruder et al., Mesenchymal Stem Cells in Bone Development, Bone Repair, and Skeletal Regeneration Therapy, J. Cell Biochem; (1994) 56:283-294.
Dennis et al., Osteogenesis in Marrow-Derived Mesenchymal Cell Porous Ceramic Composites Transplanted Subcutaneously: Effect of Fibronectin and Laminin on Cell Retention and Rate of Osteogenic Expression, Cell Transplant (1992) 1:23-32, Abstract.
Gronthos, S., et al., (1999) "Differential Cell Surface Expression of the STRO-1 and Alkaline Phosphatase Antigens on Discrete Developmental Stages in Primary Culture of Human Bone Cells," Journal of Bone and Mineral Research, 14(1): 47-56.

(56) References Cited

OTHER PUBLICATIONS

Stewart, K., et al., (1999) "Further Characterization of Cells Expressing STRO-1 in Cultures of Adult Human Bone Marrow Stromal Cells," Journal of Bone and Mineral Research, 14(8): 1345-1356.
International Search Report issued by the International Searching Authority (ISA/AU) dated May 17, 2004 in connection with International Application No. PCT/AU2004/000416.
International Preliminary Report on Patentability issued by the International Bureau of WIPO dated Oct. 1, 2005 in connection with International Application No. PCT/AU2004/000416.
International Search Report issued by the International Searching Authority (ISA/AU) dated Nov. 25, 2005 in connection with International Application No. PCT/AU2005/001445.
Office Action dated Jan. 12, 2005 in connection with U.S. Appl. No. 10/030,411.
Office Action dated Jun. 28, 2005 in connection with U.S. Appl. No. 10/030,411.
Final Office Action dated Jan. 9, 2006 in connection with U.S. Appl. No. 10/030,411.
Office Action dated Apr. 20, 2007 in connection with U.S. Appl. No. 10/955,709.
Office Action dated Aug. 24, 2007 in connection with U.S. Appl. No. 11/178,920.
Office Action dated Aug. 25, 2006 in connection with 110/955,709.
Examiner Interview Summary dated Jun. 27, 2006 in connection with U.S. Appl. No. 10/030,411.
Office Action dated Dec. 15, 2006 in connection with U.S. Appl. No. 11/178,920.
Office Action dated Jul. 10, 2006 in connection with U.S. Appl. No. 11/178,920.
Office Action dated Jan. 22, 2007 in connection with U.S. Appl. No. 11/169,875.
Office Action dated Jul. 10, 2006 in connection with U.S. Appl. No. 10/813,747.
Office Action dated Dec. 15, 2006 in connection with U.S. Appl. No. 10/813,747.
Office Action dated Apr. 3, 2007 in connection with U.S. Appl. No. 10/813,747.
Office Action dated Oct. 19, 2007 in connection with U.S. Appl. No. 10/813,747.
Restriction Requirement dated Jan. 8, 2008 in connection with U.S. Appl. No. 10/551,162.
Restriction Requirement dated Jan. 8, 2008 in connection with U.S. Appl. No. 11/326,736.
Final Office Action dated Jan. 10, 2008 in connection with U.S. Appl. No. 10/955,709.
Restriction Requirement dated Apr. 4, 2008 in connection with U.S. Appl. No. 10/551,326.
Extended European Search Report dated Dec. 27, 2007 in connection with European Application No. 05787106.3.
Cochlovius, B. et al. (2003) "Therapeutic Antibodies," Modern Drug Discovery pp. 33-34, 37-38.
Gronthos et al. Journal of Hematotherapy, 1996. 5, 15-23 (Abstract).
Hansson, M. et al. (2007) "Commentary: Isolated Stem Cells—Patentable as Cultural Artifacts?" V.25, pp. 1507-1510.
Pan, Beiqing et al. (2004) "The nitrogen-containing bisphosphonate, zaledronic acid, increases mineralisation of human bone-derived cells in vitro." Bone 34:112-123.
Cassiede, P. et al. (1996) "Osteochondrogenic Potential of Marrow Mesenchymal Progenitor Cells Exposed to TGF-β1 or PDGF-BB as Assayed in Vivo and in Vitro" Journal of Bone and Mineral Research vol. 11(9):1264-1273.
Kang Yong Jung et al. (2004) "Involvement of PI-3-kinase, JNK, PKC, and PKA in the PDGF-induced proliferation in himan adipose tissue-derived mesenchymal stem cells" vol. 18(8) p. C253.
Barry, F.P. (2003) "Biology and Clinical Applications of Mesenchymal Stem Cells." Birth Defect Research (Part C), 69:250-256.
Chopp, M. and Li, Y. (2002) "Treatment of Neural Injury with Marrow Stromal Cells." The Lancet Neurology 1:92-100.

Dennis JE, et al. (2002), "The STRO-1+ Marrow Cell Population is Multipotential." Cells Tissues Organs, 170:73-82.
Greenberger, J. and Keating, A. (1996) "The Hematopoietic Microenvironment." Keystone Symposium, Taos, New Mexico14:366-367.
Hoerstrup SP et al. (2002), "Tissue Engineering of Functional Trileaflet Heart Valves From Human Marrow Stromal Cells." Circulation 106(Suppl):I-143-I-150.
Kassem, M. (2004) "Mesenchymal Stem Cells: Biological Characteristics and Potential Clinical Applications." Cloning Stem Cells 6:369-374.
Le Blanc, K. and Ringden, O. (2005) "Immunobiology of Human Mesenchymal Stem Cells and Future Use in Hematopoietic Stem Cell Transportation." Biology of Blood and Marrow Transplantation 11:321-334.
Murray et al. (1996) "Fetal Bone Marrow $CD34^+CD41^+$ Cells are Enriched for Multipotent Hematopoietic Progenitors, but not for Pluripotent Stem Cells." Exp. Hematol. 24:236-245.
Summer, R. and Fine, A. (2008) "Mesenchymal Progenitor Limitations and Recommendations." Proc.Am, Thorac. Soc 5:707-710.
Supplementary European Search Report dated Jan. 2, 2008 in connection with European Application No. 05754008.0.
Nov. 13, 2007 Office Action issued in connection with U.S. Appl. No. 11/169,875.
Sep. 12, 2008 Office Action issued in connection with U.S. Appl. No. 10/551,162.
Oct. 16, 2008 Office Action issued in connection with U.S. Appl. No. 10/955,709.
Nov. 13, 2008 Office Action issued in connection with U.S. Appl. No. 10/551,326.
Nov. 17, 2008 Office Action issued in connection with U.S. Appl. No. 11/326,736.
Nov. 26, 2008 Office Action issued in connection with U.S. Appl. No. 11/169,875.
Finney, M.R. et al. (2006) "Direct Comparison of Umbilical Cord Blood versus Bone Marrow-Derived Endothelial Precursor Cells in mediating Neovascularization in Response to Vascular Ischemia." Biol. Blood and Marrow Transplant. 12:585-593.
Feb. 27, 2009 European Examination Report issued in connection with European Application No. 04723937.1.
Apr. 28, 2009 Final Office Action issued in connection with U.S. Appl. No. 10/813,747.
Holden et al. (2002) "Plasticity Time for a Reappraisal?" Science vol. 296 pp. 2126-2129.
Poulsom et al. (2003) "Bone Marrow Stem Cells Contribute to Healing of the Kidney." Journal of the American Society of Nephrology. vol. 14 pp. s48-s54.
International Search Report issued by the International Searching Authority (ISA/AU) dated Aug. 22, 2005 in connection with International Application No. PCT/AU2005/000953.
Zvaifler, et al., (2000) "Mesenchymal precursor cells in the blood of normal individuals," *Arthritis Research and Therapy*, 2: 477-488.
Ji, et al., (2004) "Interactions of Chemokines and Chemokine Receptors Mediate the Migration of Mesenchymal Stem Cells to the Impaired Site in the Brain After Hypoglossal Nerve Injury," *Stem Cells*, 22: 415-427.
Sordi, et al., (2005) "Bone marrow mesenchymal stem cells express a restricted set of functionally active chemokine receptors capable of promoting migration to pancreatic islets," *Blood*, 106(2): 419-427.
Wynn, et al., (2004) "A small proportion of mesenchymal stem cells strongly expresses functionally active CXCR4 receptor capable of promoting migration to bone marrow," *Blood*, 104(9): 2643-2645.
Kortesidis, et al., (2005) "Stromal-derived factor-1 promotes the growth, survival, and development of human bone marrow stromal stem cells," *Blood*, 105(10): 3793-3801.
Yang XB, et al. (2006), "Evaluation of Human Bone Marrow Stromal Cell Growth on Biodegradable Polymer/Bioglass Composites," Biochemical and Biophysical Research Communications 342:1098-1107.
Fujii, S. et al. (2008), "Investigating a Clonal Human Periodontal Ligament Progenitor/Stem Cell Line in Vitro and in Vivo," J. Cell. Physiol. 215:743-749.

(56) References Cited

OTHER PUBLICATIONS

Bianco, P. et al. (2001), "Bone Marrow Stromal Stem Cells: Nature, Biology, and Potential Applications," Stem Cells 19:180-192.
Final Office Action dated Jun. 22, 2009 in connection with U.S. Appl. No. 10/551,162.
Final Office Action dated Jun. 23, 2009 in connection with U.S. Appl. No. 11/169,875.
Final Office Action dated Jul. 16, 2009 in connection with U.S. Appl. No. 10/955,709.
Final Office Action dated Sep. 29, 2009 in connection with U.S. Appl. No. 10/551,326.
Final Office Action dated Oct. 8, 2009 in connection with U.S. Appl. No. 11/326,736.
Notice of Allowance dated Oct. 29, 2009 in connection with U.S. Appl. No. 10/813,747.
Final Office Action dated Dec. 9, 2009 in connection with U.S. Appl. No. 11/169,875.
Examination Report dated Oct. 10, 2009 in connection with corresponding European Application No. 05754008.0.
Neuhaus T. et al. (2003) "Stromal cell-derived factor 1alpha (SDF-1alpha) induces gene-expression of early growth response-1 (Egr-1) and VEGF in human arterial endothelial cells and enhances VEGF induced cell proliferation" Cell Proliferation, 36:75-86.
Salcedo R. et al. (1999) "Vascular endothelial growth factor and basic fibroblast growth factor induce expression of CXCR4 on human endothelial cells: In vivo neovascularization induced by stromal-derived factor-1alpha" American Journal of Pathology, 154:1125-1135.
Kanbe K. et al. (2002) "Stimulation of Matrix Matalloprotease 3 Release from Human Chondrocytes by the Interaction of Stromal Cell-Derived Factor 1 and CXC Chemokine Receptor 4" Arthritis & Rheumatism 46:130-137.
Office Action dated Jan. 19, 2010 in connection with corresponding Japanese Application No. 2006-503989.
Office Action dated Sep. 22, 2009 in connection with U.S. Appl. No. 11/663,570.
Office Action dated Mar. 16, 2010 in connection with U.S. Appl. No. 11/663,570.
Final Office Action dated Jun. 2, 2010 in connection with U.S. Appl. No. 11/169,875.
Office Action dated Aug. 26, 2010 in connection with U.S. Appl. No. 10/551,162.
English Translation of Office Action dated May 23, 2016 by the Korean Patent Office in connection with Korean Application No. 10-2016-7004806.
Neuhaus et al. "Stromal cell-dreived factor 1α (SDF-1α) induces gene-expression of early growth response-1 (Egr-1) and VEGF in human arterial endothelial cells and enhances VEGF induced cell proliferation," Cell Prolif. 36:75-86 (2003).

* cited by examiner

A

B

Negative Controls

Bone

Bone (continued)

Epithelial

Chondrocytes

Cardiomyocytes

Basal Fibroblasts

Smooth Muscle

Endothelial Cells

Growth Factor Receptors-Various Cell Types

Neural

SEQUENCE LISTING

<160> NUMBER OF SEQ ID NOS: 3

<210> SEQ ID NO 1
<211> LENGTH: 89
<212> TYPE: PRT
<213> ORGANISM: Homo sapiens

<400> SEQUENCE: 1

Met Asn Ala Lys Val Val Val Leu Val Leu Val Leu Thr Ala Leu
1               5                   10                  15

```
Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 2
<211> LENGTH: 93
<212> TYPE: PRT
<213> ORGANISM: Homo sapiens

<400> SEQUENCE: 2

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 3
<211> LENGTH: 352
<212> TYPE: PRT
<213> ORGANISM: Homo sapiens

<400> SEQUENCE: 3

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160
```

-continued

```
Trp Ile Pro Ala Leu Leu Thr Ile Pro Asp Phe Ile Phe Ala Asn
            165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
            195                 200                 205

Ile Leu Pro Gly Ile Val Ile Leu Ser Cys Tyr Cys Ile Ile Ile Ser
            210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                    245                 250                 255

Ile Gly Ile Ser Ile Asp Ser Phe Ile Leu Leu Glu Ile Ile Lys Gln
                    260                 265                 270

Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                    325                 330                 335

His Ser Ser Val Ser Thr Glu Ser Glu Ser Ser Ser Phe His Ser Ser
            340                 345                 350
```

METHOD OF INCREASING PROLIFERATION OF BONE MARROW MONONUCLEAR CELLS EXPRESSING STRO1-$^{dim}$ This application is a continuation-in-part of U.S. Ser. No. 12/924,008, filed Sep. 16, 2010, which is a continuation of U.S. Ser. No. 11/663,570, filed Mar. 23, 2007, now abandoned, which is a § 371 national stage of PCT International Application No. PCT/AU2005/000953, filed Jun. 29, 2005, which claims the benefit of U.S. Provisional Application No. 60/613,021, filed Sep. 24, 2004, the contents of all of which are hereby incorporated by reference into this application.

FIELD OF THE INVENTION

The present invention relates to compositions comprising mesenchymal precursor cells (MPC) and/or precursor cells derived therefrom and to methods for enhancing the proliferation and/or survival of these cells in vitro or in vivo. The present invention also relates to methods for ex vive or In vivo formation of bone in mammals.

REFERENCE TO SEQUENCE LISTING

This application incorporates-by-reference nucleotide and/or amino acid sequences which are present in the file named "191029_77677-AA_Substitute_Sequence_Listing_ND", which is 7 kilobytes in size, was created Oct. 22, 2019 in the IBM-PC machine format, has an operating system compatibility with MS-Windows, and is contained in the text file submitted Oct. 29, 2019.

BACKGROUND OF THE INVENTION

Bone remodelling is a continuous physiological process that occurs in adult skeleton in which bone resorption is followed by new bone formation, maintaining mechanical strength and structure. Bone cells that are responsible for this coupled process include bone-resorbing cells (osteoclasts, which are derived from haematopoietic cells of the monocyte/macrophage lineage) and bone-forming cells (osteoblasts, which are of mesenchymal origin). The bone resorption process is involved in many clinical situations that are relevant to the work of rheumatologists, such as focal bone destruction or erosion in RA and other inflammatory arthritides, and the diffuse bone loss that is encountered in osteoporosis.

Osteoclast activation is a critical cellular process for pathological bone resorption, such as erosions in rheumatoid arthritis (RA) or generalized bone loss. Among many factors triggering excessive osteoclast activity, cytokines such as IL-1 or tumour necrosis factor (TNF)-α play a central role. More recently, the chemokine stromal cell-derived factor-1 (SDF-1) has been shown to promote the chemotactic recruitment, development and survival of human osteoclasts (Wright et al., Bone 36:840-853, 2005; Zannettino et al., Cancer Res 65(5): 1700-1709, 2005; Grassi et al., J. Cell. Physiol. 199:244-251, 2004).

Chemokines are a superfamily of chemoattractant proteins which regulate a variety of biological responses and they promote the recruitment of multiple lineages of leukocytes and lymphocytes to a body organ tissue. Chemokines may be classified into two families according to the relative position of the first two cysteine residues in the protein. In one family, the first two cysteines are separated by one amino acid residue, the CXC chemokines, and in the other family the first two cysteines are adjacent, the CC chemokines. In humans, the genes of the CXC chemokines are clustered on chromosome 4 (with the exception of SDF-1 gene, which has been localized to chromosome 10) and those of the CC chemokines on chromosome 17.

The molecular targets for chemokines are cell surface receptors. One such receptor is CXC chemokine receptor 4 (CXCR4), which is a 7 transmembrane protein, coupled to G1 and was previously called LESTR (Loetscher et al., (1994) J. Biol. Chem, 269: 232-237, 1994), HUMSTR (Federappiel et al., Genomics 16, 707-712, 1993) and Fusin (Feng et al., Science 272: 872-877, 1996). CXCR4 is widely expressed on cells of hemopoietic origin, and is a major co-receptor with CD4$^+$ for human immunodeficiency virus 1 (HIV-1) (Feng at al., Science 272: 872-877, 1996).

Currently, the only known natural ligand for CXCR4 is SDF-1. Stromal cell derived factor-1 alpha (SDF-1 alpha) and stromal cell derived factor-1 beta (SDF-1 beta) are closely related proteins (together referred to herein as SDF-1). The native amino acid sequences of SDF-1 alpha and SDF-1 beta are known, as are the genomic sequences encoding these proteins (U.S. Pat. Nos. 5,563,048 and 5,756,084).

The 3-dimensional crystallographic structure of SDF-1 has been described (Crump et al., EMBO J. 16: 6996-7007, 1997). Structure-activity analysis of SDF-1 indicates that although N-terminal residues 1-8 or 1-9 are involved in receptor binding, the 1-8 and 1-9 peptides alone exhibited no in vitro activity indicative of receptor binding, supporting a reported conclusion that the peptides do not assume the conformation necessary for binding to the receptor. This result was taken to imply that the remainder of the protein scaffold, and/or various consensus receptor binding sites elsewhere in the protein are important for mediating the conformational requirements for N-terminal binding to the receptor (Crump et al., EMBO J. 16: 6996-7007, 1997). Based on these results, a two-site model has been proposed for SDF-1 binding to CXCR4, involving two binding sites in residues 1-17, an N-terminal site and an upstream RFFESH site (Crump at al., EMBO J. 16: 6996-7007, 1997). The two putative binding sites are joined by the CXC motif that characterizes the whole CXC chemokine family. These two putative binding regions have been identified as being important in other CC and CXC chemokines (Crump et al., EMBO J. 16: 6996-7007, 1997). This is consistent with the finding that although N-terminal regions of a wide variety of chemokines are critical for receptor activation, N-terminal peptides of chemokines other than SDF-1 have been reported to lack receptor binding activity and not to be receptor agonists (Crump et al., EMBO J. 16: 6996-7007, 1997).

Postnatal human bone marrow stromal stem cells (BMSSCs) or mesenchymal precursor cells (MPCs) have the capacity to regenerate a hematopoietic-supportive bone marrow organ and associated bone trabecular, when transplanted into immunocompromised mice (Friedenstein et al. Exp Hematol. 6: 440-444, 1978; Kuznetsov et al. J Bone Miner Res. 12: 1335-1347, 1997; Pittenger et al. Science 284: 143-147, 1999; Bianco et al., Stem Cells 19: 180-192, 2001; Gronthos et al. J Cell Sci. 116: 1827-1835, 2003). Recent studies have also reported that BMSSCs are more plastic than first realized, by virtue of their ability to develop into diverse cell lineages such as myelosupportive stroma, osteoblasts, chondrocytes, adipocytes, myoblasts, hepatocytes, cardiomyocytes, and neural cells (Liechty et al. Nat Med. 6: 1282-1286, 2000; Zhao et al. Exp Neurol. 174: 11-20, 2002; Verfaillie et al. Ann N Y Acad Sci. 996: 231-234, 2003).

These developments have prompted investigations into the possible use of ex vivo-expanded BMSSC populations for bone regeneration. However, the progress of these studies has largely been restrained because of a lack of understanding of the critical factors that regulate the growth and survival of human multipotential BMSSCs and the eventual development of these cells into bone.

SUMMARY OF THE INVENTION

The present inventors have now identified SDF-1 as a differentially expressed gene that is highly expressed by purified BMSSCs prior to culture. In particular, the present inventors have found that immature preosteogenic cells cultured in vitro expressed greater levels of SDF-1 when compared with mature cell types representative of osteoblasts and osteocytes/bone lining cells. Furthermore, SDF-1 expression was rapidly down-regulated when BMSSCs were cultured under osteoinductive conditions.

BMSSCs were also shown to express functional cell surface SDF-1 receptors (CXCR4). Transduced BMSSC lines, secreting high SDF-1 levels, displayed an enhanced ability to form ectopic bone in vivo, in comparison with control BMSSC lines. Moreover, high SDF-1-expressing BMSSCs displayed an increased capacity for cellular growth and protection against interleukin-4-induced apoptosis. Similarly, fibroblast colony-forming units (CFU-Fs) also displayed increased growth and resistance to α-interferon-2a-induced apoptosis, in synergy with platelet-derived growth factor BB (PDGF-BB) and SDF-1 in vitro.

These findings indicate that the chemokine SDF-1 plays a role in the proliferation, survival, and osteogenic capacity of immature BMSSC populations.

Accordingly, the present invention provides a method of enhancing proliferation and/or survival of mesenchymal precursor cells (MPC) or progeny derived therefrom, the method comprising exposing the MPC or progeny to SDF-1 or an analog thereof.

The present invention also provides a method of developing a tissue specific committed cell population, the method comprising the steps of contacting MPC or progeny derived therefrom with SDF-1 or an analog thereof to enhance proliferation and/or survival of the MPC or progeny, and subjecting the proliferated population to conditions biasing differentiation of the MPC or progeny derived therefrom to a specific tissue type.

The present invention also provides an MPC or precursor cell derived therefrom that has been genetically modified to overexpress SDF-1 or an analog thereof.

The present invention also provides a composition comprising a population of transfected MPC of the present invention.

The present invention also provides a composition comprising MPC or progeny derived therefrom and SDF-1 or an analog thereof.

The present invention also provides a method of generating bone in a subject, the method comprising exposing MPC or progeny derived therefrom in the subject to exogenous SDF-1 or an analog thereof.

The present invention also provides a method of generating bone in a subject, the method comprising administering a composition of the invention to the subject at the site of desired bone generation.

Figure 19:
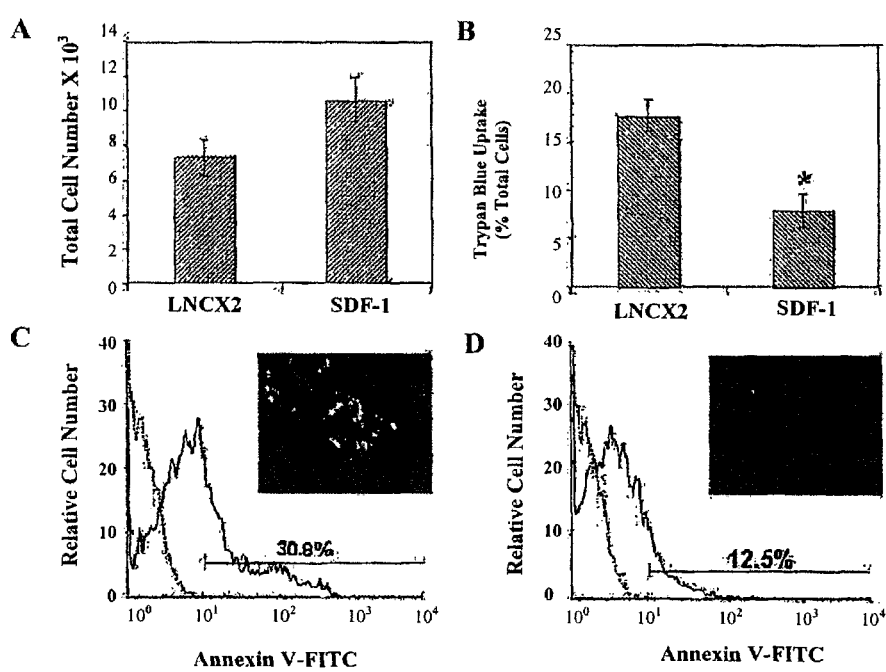

FIG. 19. Enforced expression of SDF-1 by BMSSCs improves cell survival (A) Proliferation studies were performed by plating high SDF-1-expressing BMSSCs and vector control cell lines in triplicate wells at a density of 5×10$^3$ cells/well in 96-well plates in regular growth medium for 5 days. Single-cell suspensions were then prepared by trypsin/EDTA digest and counted to assess the total number of cells. (B) Parallel cultures were established in the presence of interleukin 4 (IL-4; 30 ng/mL), and the percentage of apoptotic cells was measured by using trypan blue exclusion. (C) The histogram represents the level of cell surface annexin V staining (solid line) by control cell lines compared with the isotype-matched control antibody (dotted line) cultured in the presence of IL-4. A representative image is shown of the intensity of fluorescence staining on living cells in situ (×100). (D) The histogram represents the level of cell surface annexin V staining (solid line) by high SDF-1-expressing BMSSC lines compared with the isotype-matched control (dotted line) cultured in the presence of IL-4. A representative image is shown of the intensity of fluorescence staining on living cells in situ (×100). The data represent the mean values±standard errors of triplicate experiments. Statistical differences (*) of P<0.05 between the SDF-1 high-expressing BMSSC lines and corresponding controls were determined by using the unpaired t test.

Figure 20:
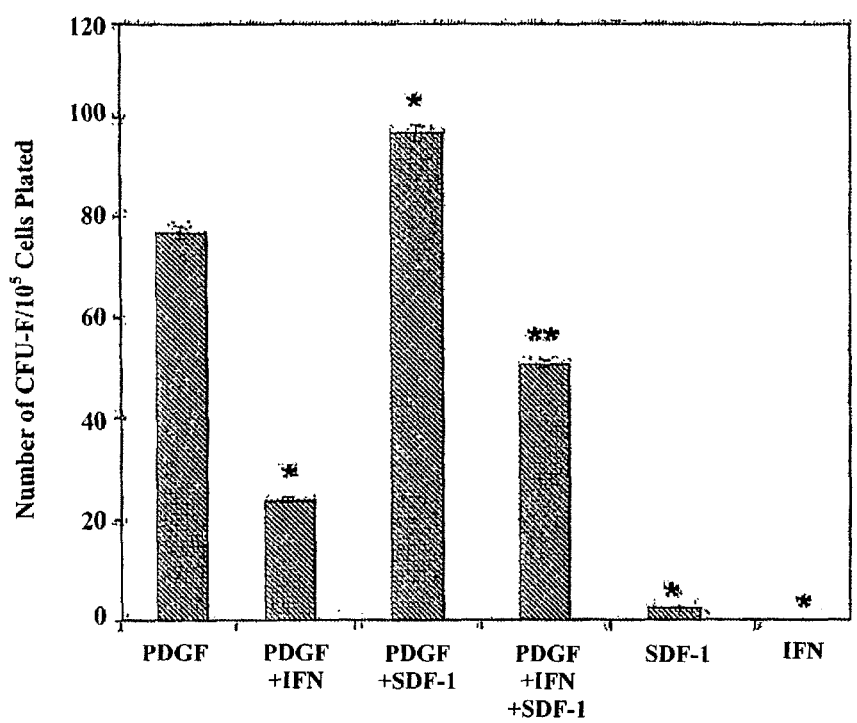

FIG. 20. SDF-1 promotes the growth and survival of CFU-F. The total number of CFU-F colonies derived from MACS/FACS-solated STRO-1$^{bright}$ BMMNCs plated in serum-free media in the presence of different cytokine combinations was enumerated. Recombinant human PDGF-BB, SDF-1α, and α-interferon 2a were used at the optimal concentrations 5 ng/mL, 30 000 IU/mL and 30 ng/mL, respectively. The data represent the mean values t standard errors of triplicate wells. Similar results were obtained by using 3 different bone marrow aspirates. Statistical significance (P<0.01) was determined by using one-way ANOVA for all treatments. The Fisher test was then used to determine the differences between all groups. Significant differences (P<0.05) were found between all treatments compared with PDGF-BB alone (*), and PDGPF+IFN (interferon) verses PDGF+SDF-1+IFN (**) at a significance of P<0.05.

Figure 21:
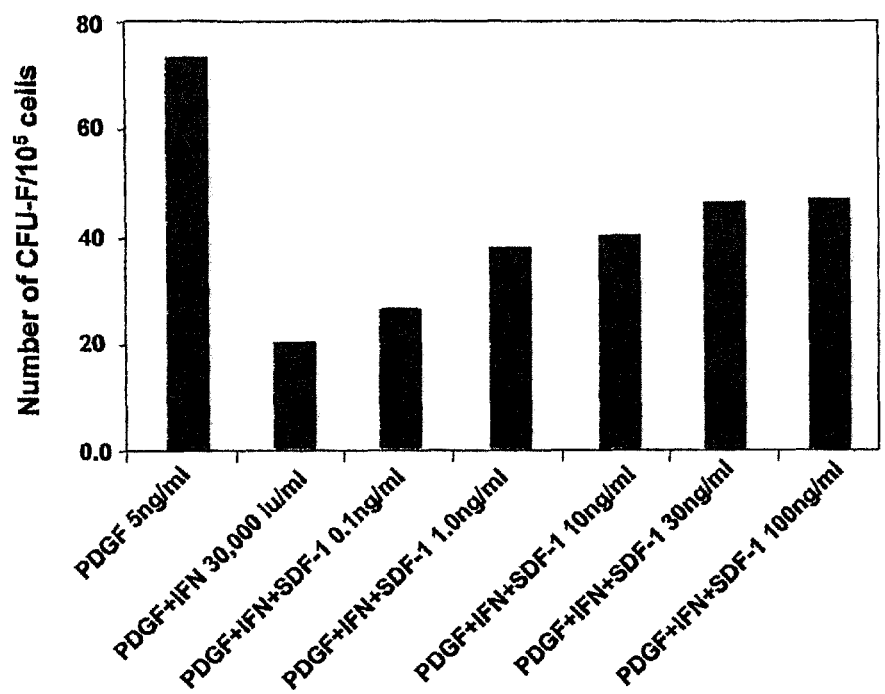

FIG. 21. SDF-1 protects CFU-F formation against the apoptotic effects of IFN-alpha in a dose dependent manner. STRO-1 MACS selected human bone marrow mononuclear cells were plated into serum-deprived media in the presence of either PDGF (5 ng/ml) alone or PDGF and IFN-alpha (30,000 i.u./ml) or PDGF and IFN-alpha and SDF-1 (0.1-100 ng/ml). Following 14 days of culture the plates were fixed and stained as described in the Methods for CFU-F colony enumeration.

DETAILED DESCRIPTION OF THE INVENTION

The present inventors have made the surprising finding that the chemokine SDF-1 plays a role in the proliferation, survival, and osteogenic capacity of immature BMSSC populations.

Accordingly, the present invention provides a method of enhancing proliferation and/or survival of mesenchymal precursor cells (MPC) or progeny derived therefrom, the method comprising exposing the MPC or progeny to SDF-1 or an analog thereof.

As used herein, MPC are non-hematopoietic progenitor cells that are capable of forming large numbers of multipotential cell colonies.

In a preferred example of the present invention the MPC are positive for at least one marker selected from the group consisting of STRO-1$^{bright}$, VCAM-1$^{bright}$, THY-1$^{bright}$, CD146$^{bright}$ and STRO-2$^{bright}$.

The term "bright", when used herein, refers to a marker on a cell surface that generates a relatively high signal when detectably labelled. Whilst not wishing to be limited by theory, it is proposed that "bright" cells express more of the target marker protein (for example the antigen recognised by STRO-1) than other cells in the sample. For instance, STRO-1$^{bright}$ cells produce a greater fluorescent signal, when labelled with a FITC-conjugated STRO-1 antibody as determined by FACS analysis, than non-bright cells (STRO-1$^{dull/neg}$). Preferably, "bright" cells constitute at least about 0.1% of the most brightly labelled bone marrow mononuclear cells contained in the starting sample. In other embodiments, "bright" cells constitute at least about 0.1%, at least about 0.5%, at least about 1%, at least about 1.5%, or at least about 2%, of the most brightly labelled bone marrow mononuclear cells contained in the starting sample. Preferably, the "bright" cells are STRO-1$^{bright}$, VCAM-1$^{bright}$, THY-1$^{bright}$, STRO-2$^{bright}$ and/or CD146$^{bright}$ cells. As discussed in WO 01/04268, a sub-population of cells selected upon the basis of label intensity, such as STRO-1$^{bright}$ cells, have a greater proportion of MPCs than sub-populations solely selected on a positive/negative identification of the cell marker.

In a further preferred example of the present invention the MPC carry at least two markers selected from the group of surface markers specific for mesenchymal precursor cells consisting of STRO-1$^{bri}$, LFA-3, THY-1, VCAM-1, ICAM-1, PECAM-1, P-selectin, L-selectin, CD49a/CD49b/CD29, CD49c/CD29, CD49d/CD29, CD29, CD18, CD61, beta-1 integrin, 6-19, thrombomodulin, CD10, CD13, SCF, PDGF-R, EGF-R, IGF1-R, NGF-R, FGF-R, Leptin-R, (STRO-2=Leptin-R), RANKL and CD146 or any combination of these markers.

In a further preferred example of the present invention the MPC are negative for at least one marker selected from the group consisting of CD34, CD14, CD45, CBFA-1, collagen type II, PPARγ2, and glycophorin A.

Methods for preparing enriched populations of MPC are described in WO01/04268 and WO2004/085630.

In an in vitro context MPCs will rarely be present as an absolutely pure preparation and will generally be present with other cells that are tissue specific committed cells (TSCC). WO01/04268 refers to harvesting such cells from bone marrow at purity levels of about 0.1% to 90%. Alternative harvesting methods may result in proportions of MPC that are present at lower levels.

The population comprising MPC to which the method of the invention is applied may be directly harvested from a tissue source, or alternatively it may be a population that has already been expanded ex vivo.

For example, the method of the invention may be applied to a harvested, unexpanded, population of substantially purified MPC, comprising at least about 0.1, 1, 5, 10, 20, 30, 40, 50, 60, 70, 80 or 95% of total cells of the population in which they are present. This level may be achieved, for example, by selecting for cells that are positive for at least one marker selected from the group consisting of STRO-$1^{bright}$, VCAM-$1^{bright}$, THY-$1^{bright}$, CD$146^{bright}$ and STRO-$2^{bright}$.

The MPC may be derived from any one or more tissue types set out in WO01/04268 or WO2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, *thymus*, pancreas, bone, ligament, bone marrow, tendon and skeletal muscle.

The preferred source of such cells is human, however, it is expected that the invention is also applicable to animals, including agricultural animals such as cows, sheep, pigs and the like, domestic animals such as dogs and cats, laboratory animals such as mice, rats, hamsters and rabbits or animals that are be used for sport such as horses.

The term "progeny" as used herein is intended to refer to cells derived from MPC. The progeny may be precurosor cells or fully differentiated cells (such as bone cells).

In one preferred embodiment, the progeny is a precursor cell.

As used herein, a "precursor cell" derived from an MPC is a partially specialized or tissue specific committed cell (TSCC) that divides and gives rise to differentiated cells.

Although a precursor cell is committed to a differentiation pathway it generally does not express the markers of or function as a mature, fully differentiated cell. Thus, precursor cells give rise to related types of cells but in their normal state do not generate a wide variety of cell types. Precursor cells tend to be committed to one cell or tissue lineage type, however they may be bi-potential, that is capable of further differentiation into one of two different cell or tissue types.

Non-limiting examples of the lineages to which precursor cells may be committed include bone precursor cells; hepatocyte progenitors, which are pluripotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other committed precursor cells include but are not limited to chondrocytes, odontoblast, dentin-producing and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal; astrocyte and oligodendrocyte cells. Precursor cells also include those that specifically lead to connective tissue including adipose, areolar, osseous, cartilaginous, elastic and fibrous connective tissues.

In a preferred example of the present invention, the precursor cells are bone precursor cells.

As used herein, a "bone precursor cell" is any cell that is capable of differentiating or expanding into an osteoblast cell. Preferred bone precursor cells include osteoprogenitor cells and preosteoblast cells.

The enhanced proliferation effected by the method of the invention may result in increases in MPC numbers of greater than 10, 20, 30, 40 or 50% relative to non stimulated controls. Alternatively the increases may be 1, 2 or more fold.

In a preferred example of the present invention, the SDF-1 analog is a ligand that activates CXCR4 signalling. The SDF-1 analog may be, for example, a biologically active fragment, variant or derivatives of naturally occurring SDF-1.

In a further preferred example of the present invention, the SDF-1 analog is selected from the group consisting of the HIV-1 coat protein gp120, AMD3100 (AnorMED Inc, British Columbia, Canada) and ALX40-4C (Allelix Biopharmaceuticals Inc, Canada).

In a further preferred example of the present invention the MPC or progeny derived therefrom are also exposed to a stimulatory factor selected from the group consisting of exogenous platelet derived growth factor (PDGF), stem cell factor (SCF), flt 3 ligand (FL), granulocyte colony-stimulating factor (G-CSF), interleukin-3 (IL-3), interleukin-6 (IL-6), 1α,25-dihydroxyvitamin D3 (1,25D), tumour necrosis factor α (TNF-α) and interleukin-1β (IL-1β).

It is generally contemplated that the method of the invention has applicability to in vitro cultivation of cells, for example, in relation to freshly harvested or ex vivo expanded cultures, however, the invention may also have applicability where the MPC or progeny derived therefrom are in situ in a body tissue site and exogenous SDF-1 or an analog thereof is delivered to the site. One such delivery may be adequate, however temporally spaced delivery may provide an accelerated or greater benefit.

The exogenous SDF-1 or analog thereof may be administered to the subject in the form of a polypeptide or in the form of a nucleic acid that can be expressed to produce a polypeptide. For example, the exogenous SDF-1 or analog thereof may be administered in the form of a nucleic acid-containing composition or in the form of a host cell that has been genetically modified to overexpress SDF-1 or analog thereof.

In the context of in vivo delivery it might also be desirable to deliver (at the same time as the SDF-1 or analog thereof) a composition comprising MPC or progeny derived therefrom. For example, in the case of a lesion in a bone, a cardiac muscle, a vascular tissue or endothelial cells, the progeny that are delivered are preferably at least partially committed to a relevant cell type (e.g., an osteoblast, a cardiomyocyte or an endothelial cell). These may be provided as part of a mixed precursor cell culture or in a more purified form, for example, being sorted for markers known to be present on the tissue specific committed cell type. Alternatively or additionally the composition being delivered may include one or more differentiation stimulatory factors to differentiate MPC either present in the composition or present in situ at the target site to one or more tissue types of interest.

The present invention also provides a method of developing a tissue specific committed cell population, the method comprising exposing MPC or progeny derived therefrom to exogenous SDF-1 or an analog thereof to enhance proliferation and/or survival of the MPC or progeny, and subjecting the proliferated population to conditions biasing differentiation of the MPC or progeny derived therefrom to a specific tissue type.

The tissue type may be selected from the group consisting of cardiac muscle, a vascular tissue, osteoblast, odontoblast, osteocyte, bone lining cell and endothelial cell. Exemplified conditions for in vitro development of these tissue types and for in vivo promotion of these tissue types will be known to those skilled in the art.

The above method may be applied the generation or repair of skeletal muscle, cardiac muscle, bone, teeth, or vascular tissue. In particular, the method may be applied to the generation or repair of cells or tissue selected from the group consisting of cardiac muscle, cardiomyocytes, chondrocytes, osteoblasts, osteoclast, odontoblast, dentin-producing chrondocyte, osteocyte, bone lining cell, skeletal muscle cells, vascular endothelial cells, marrow stroma, osteoclast and haemopoietic-supportive stroma, cardiac muscle, skeletal muscle, endothelial cell and a vascular cell.

In one particular example the present invention provides a method for generating bone ex vivo, the method comprising exposing MPC or progeny derived therefrom to exogenous SDF-1 or an analog thereof to enhance proliferation and/or survival of the MPC or progeny, and subjecting the proliferated population to conditions biasing differentiation of the MPC to bone precursor cells, or to conditions biasing differentiation of bone precursor cells to bone.

Conditions that bias differentiation of the MPC or bone precursor cells derived therefrom to bone may involve, for example, culturing in αMEM supplemented with 10% FCS, 100 µM L-ascorbate-2-phosphate, dexamethasone $10^{-7}$ M and 3 mM inorganic phosphate. These conditions have been shown to induce human BM stromal cells to develop a mineralized bone matrix in vitro (Gronthos et al., *Blood* 84:4164-73, 1994).

In an alternative example, the method may involve differentiating the bone precursor cells into osteoblasts by cultivating the bone precursor cells in the presence of type I collagen, fibrinogen, fibrin, polyglycolic acid, polylactic acid, osteocalcin, or osteonectin. In one particular example, bone precursor cells are cultivated in the presence of type I collagen, fibrinogen, and fibrin. In an alternative example, bone precursor cells are cultivated in the presence of type I collagen, fibrinogen, fibrin, osteocalcin, and osteonectin. In the context of this method, type I collagen, fibrinogen, fibrin, polyglycolic acid, polylactic acid, osteocalcin, or osteonectin may be used alone or in the presence of a growth factor. It will be understood that any combination of the compounds listed above in this paragraph is contemplated by the present invention.

The present invention also provides a composition comprising isolated MPC or progeny derived therefrom and SDF-1 or an analog thereof.

In a preferred example, the composition comprises substantially purified MPC or progeny, comprising at least about 0.1, 1, 5, 10, 20, 30, 40, 50, 60, 70, 80 or 95% of total cells of the composition.

In a further preferred example, the SDF-1 or analog thereof is present in the composition at a concentration of about 0.1 nM-0.1 M, 0.1 mM-0.05 M, 0.05 nM-15 µM or 0.01 nM-10 µM.

The present invention also provides an MPC or precursor cell derived therefrom that has been genetically modified to overexpress SDF-1.

In one example the MPC or precursor cell derived therefrom is transfected with a polynucleotide encoding SDF-1.

In another example, the genome of the MPC or precursor cell derived therefrom is modified to effect overexpression of the SDF-1 protein. In one example, a regulatory region of the SDF-1 gene of the MPC or precursor cell derived therefrom is modified to effect overexpression of the SDF-1 protein.

The present invention also provides a composition comprising a population of transfected MPC of the present invention.

The composition of the present invention may further comprises one or more additional stimulatory factors. For example, the additional stimulatory factor may be selected from the group consisting of PDGF, SCF, FL, G-CSF, IL-3, IL-6, 1,25D, TNF-α and IL-1β.

The present invention encompasses delivery systems in which a composition of the present invention (for example, a composition comprising genetically modified MPC) is administered systemically or locally to colonize a selected type of tissue, e.g., an injured tissue. For example, a composition of the present invention may be directly injected into the target tissue. The injection site is preferably at a site of injury, or nearby the injured tissue. Alternatively, genetically modified MPC expressing SDF-1 and a specific recombinant ligand or receptor may be introduced to the subject and then the cells targeted to a desired target tissue by inducing expression of the cognate binding partner in the target tissue.

It will be appreciated that the compositions of the present invention are useful for enhancing survival of grafted MPC or cells derived therefrom used in repairing or regenerating tissue, e.g., cardiomyocytes undergoing apoptosis due to an ischemic or reperfusion related injury; chondrocytes following traumatic injury to bone, ligament, tendon or cartilage; or hepatocytes in an alcohol-induced cirrhotic liver.

In one particular example the compositions of the invention are useful for enhancing survival of grafted MPC or cells derived therefrom used in repairing or regenerating bone. Thus, the compositions of the invention may further comprise a matrix such as absorbable gelatin, cellulose or collagen. The composition can be used in the form of a sponge, strip, powder, gel or web.

The present invention also provides a method of generating bone in a subject, the method comprising exposing MPC or progeny derived therefrom in the subject to exogenous SDF-1 or an analog thereof.

The present invention also provides a method of generating bone in a subject, the method comprising administering a composition of the invention to the subject at the site of desired bone generation.

This method may be used, for example, in the repair of bones, and as such a composition of the present invention and optionally a suitable support may be introduced into a site requiring bone formation. Thus, for example, skeletal defects caused by bone injury or the removal of sections of bone infected with tumour may be repaired by implanting compositions of the present invention into the defect site. Such defects include, for example, segmental bone defects, non-unions, malunions or delayed unions, cysts, tumors, necroses or developmental abnormalities. Other conditions requiring bone augmentation, such as joint reconstruction, cosmetic reconstruction or bone fusion, such as spinal fusion or joint fusion, may be treated in an individual by administering into the site of bone in need of augmentation, a composition of the present invention. The composition may be in combination with, for example, a resorbable biopolymer such as gelatin, cellulose or collagen based medium, or in a calcium phosphate ceramic vehicle to an extent sufficient to augment bone formation therefrom. The resorbable biopolymer can be in the form of a powder or sponge, and is preferably a porcine skin-derived gelatin. The ceramic vehicle can be in particulate form or can be in the form of a structurally stable, three dimensional implant. The structurally stable, three dimensional implant can be, for example, a cube, cylinder, block or an appropriate anatomical form. The composition can also contain one or more other components which degrade, resorb or remodel at rates approximating the formation of new tissue. For appropriate methods and techniques see Caplan et al. in U.S. Pat. Nos. 5,226,914 and 5,837,539.

This method may also be used to assist in anchoring prosthetic devices. Thus, the surface of a prosthetic device such as those used in hip, knee and shoulder replacement, may be coated with a composition of the present invention prior to implantation. The MPC or progeny derived therefrom in the composition may then differentiate into osteogenic cells to thereby speed up the process of bony ingrowth and incorporation of the prosthetic device (see Caplan et al. in U.S. Pat. Nos. 5,226,914 and 5,837,539).

The above methods may further comprise administering to the individual at least one bioactive factor which induces or accelerates the differentiation of MPC or progeny derived therefrom into the osteogenic lineage. The bioactive factor can be, for example, a synthetic glucocorticoid, such as dexamethasone, or a bone morphogenic protein, such as BMP-2, BMP-3, BMP-4, BMP-6 or BMP-7. The bone morphogenic protein can be in a liquid or semi-solid carrier suitable for intramuscular, intravenous, intramedullary or intra-articular injection.

The present invention also provides a method of generating vascular tissue in a subject, the method comprising exposing MPC or progeny derived therefrom in the subject to exogenous SDF-1 or an analog thereof.

The present invention also provides a method of generating vascular tissue in a subject, the method comprising administering a composition of the invention to the subject at the site of desired vascular tissue generation.

The present invention also provides a method of generating cardiac muscle or smooth muscle in a subject, the method comprising exposing MPC or progeny derived therefrom in the subject to exogenous SDF-1 or an analog thereof.

The present invention also provides a method of generating cardiac muscle or smooth muscle in a subject, the method comprising administering a composition of the invention to the subject at the site of cardiac muscle or smooth muscle generation.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Stromal Derived Factor-1 and Analogs Thereof

Stromal Derived Factor-1 (SDF-1) has also be referred to in the art as Chemokine CXC motif ligand 12 (CXCL12) and pre-B cell growth stimulating factor (PBSF). Stromal cell-derived factors 1-alpha and 1-beta are small cytokines that belong to the intercrine family, members of which activate leukocytes and are often induced by proinflammatory stimuli such as lipopolysaccharide, TNF or IL-1. The intercrines are characterized by the presence of 4 conserved cysteines which form 2 disulfide bonds. They can be classified into 2 subfamilies. In the CC subfamily, the cysteine residues are adjacent to each other. In the CXC subfamily, they are separated by an intervening amino acid. The SDF-1 proteins belong to the latter group.

As indicated above, there are at least two known isoforms of SDF-1 known as SDF-1 alpha and SDF-1 beta. Shirozu et al. (Genomics, 28:495, 1995) identified human SDF-1 genomic clones and showed that the alpha and beta isoforms are a consequence of alternative splicing of a single gene. The alpha form is derived from exons 1-3 while the beta form contains additional sequence from exon 4. The entire human gene is approximately 10 kb and is located at chromosome 10q11.1.

Unless stated to the contrary, the term "SDF-1" as used herein refers to at least the alpha and/or beta isoform. This term also includes biologically active fragments, variants and derivatives of the naturally occurring molecules which maintain at least some activity such that they are useful for the methods of the invention. In a preferred embodiment, the invention relates to the use of the alpha isoform.

The amino acid sequence of a number of different native mammalian SDF-1 alpha and/or beta proteins are known, including human, rat, mouse, and cat (see, for example, Shirozu et al., Genomics, 28:495, 1995; Tashiro et al., Science 261:600, 1993; Nishimura et al., Eur. J. Immunogenet. 25:303, 1998); and GenBank Accession No. AF189724). The amino acid sequence of the human alpha isoform is provided as SEQ ID NO:1, and the amino acid sequence of the human beta isoform is provided as SEQ ID NO:2. A preferred form of SDF-1 protein is a purified native SDF-1 protein that has an amino acid sequence identical to one of the foregoing mammalian SDF-1 proteins, or orthologs thereof obtained from other species.

SDF-1 biologically active fragments corresponding to one or more particular motifs and/or domains or to arbitrary sizes, for example, at least 5, 10, 25, 50, or 75 amino acids in length are within the scope of the present invention. The fragments can be produced (recombinantly or by chemical synthesis) and tested to identify those peptidyl fragments which can function as analogs of native SDF-1 protein.

SDF-1 variants have a peptide sequence that differs from a native SDF-1 protein in one or more amino acids. The peptide sequence of such variants can feature a deletion, addition, or substitution of one or more amino acids of a native SDF-1 protein. Amino acid insertions are preferably of about 1 to 4 contiguous amino acids, and deletions are preferably of about 1 to 10 contiguous amino acids.

SDF-1 variants can be generated through various techniques known in the art. For example, SDF-1 variants can be made by mutagenesis, such as by introducing discrete point mutation(s), or by truncation. Mutation can give rise to a SDF-1 variant having substantially the same functional activity of native SDF-1 protein. In particular, agonistic forms of the protein may be generated that constitutively express on or more of the functional activities of a native SDF-1 protein. Other SDF-1 protein variants that can be generated include those that are resistant to proteolytic cleavage, as for example, due to mutations which alter protease target sequences. Whether a change in the amino acid sequence of a peptide results in a variant having one or more functional activities of a native SDF-1 protein can be readily determined by testing the variant for a native SDF-1 protein functional activity, for example, testing the ability of the variant to stimulate the proliferation of MPCs as described herein.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of SDF-1 gene variants. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

At present SDF-1 is the only known naturally occurring agonist of the G-coupled seven transmembrane CXCR4 receptor (also known in the art as fusin or LESTR). Furthermore, MPCs have been shown to express the CXCR4 receptor (human molecule provided as SEQ ID NO:3). Thus, the biological effects of SDF-1 described herein are most likely mediated through the chemokine receptor CXCR4. Accordingly, SDF-1 analogs useful for the methods of the invention may also be CRCX4 agonists. However, the present invention does not exclude the possibility that MPCs express a receptor other than CXCR4 through which the biological activities described herein are mediated wholly, or in conjunction with another receptor such as CRCX4.

As used herein, the term "SDF-1 analog" refers to any molecule which is structurally or functionally related to SDF-1 and is suitable for use in the methods of the invention. Preferably, the SDF-1 analog is an antagonist of SDF-1 binding to CXCR4. SDF-1 analogs include biologically active fragments, variants and derivatives of naturally occurring SDF-1 as described above.

Examples of SDF-1 analogs include molecules described in US 20050065064, US 20050059584, and Pelus et al., Exp. Hematol. 33:295, 2005. In addition, evidence suggests the HIV-1 coat protein gp120 acts as a SDF-1 analog (Tran et al., J. Neuroimmunol. 160, 68 2005). Furthermore, studies have shown that AMD3100 (AnorMED Inc, British Columbia, Canada) and ALX40-4C (Allelix Biopharmaceuticals Inc, Canada) can act as agonists of the CXCR4 receptor (Zhang et al., J. Biol. Chem. 277, 24515 2002).

A variety of peptide or mimetic (including peptido-mimetics) SDF-1 protein analogs can be made utilizing conventional techniques. For example, antibodies or antibody fragments can be made against receptors (such as CXCR4) that bind SDF-1, and then screened to identify those that act as analogs of a native SDF-1 protein. Further, SDF-1 analogs can be identified by screening libraries of other molecules (such as small organic or inorganic molecules) by identifying those that bind SDF-1 protein receptors such as CXCR4. Those identified can be further characterized as agonists based on the type of signals they induce or prevent in cells.

SDF-1 analogs useful for the methods of the invention can also be identified and/or verified using the CXCR4 Receptor Agonist Redistribution™ Assay (BioImage A/S, Soeberg, Denmark).

Further examples of SDF-1 analogs are compounds containing structures corresponding to various regions or portions of SDF-1. In one embodiment, the analog comprises an N-terminal region and a C-terminal region joined together by means of a linker. In other embodiments, the amino acid residues of SDF-1 are cyclized, e.g., by etherification of lysine and serine residues or by other means known in the art. In still other embodiments, the SDF-1 analog comprises an amino acid sequence derived from the wild-type chemokine sequence but with one or more of the cysteines replaced with another amino acid. Other embodiments include chemokine analogs comprising an N-terminal region, an internal region containing up to three anti-parallel β-sheets, a C-terminal region containing an α-helical structure, a combination of the N- and C-terminal regions linked together directly, a combination of a N-terminal and internal region, or a combination of an internal and C-terminal region, or finally a combination of N-terminal, internal and C-terminal regions. The regions selected from the N-terminal, internal and C-terminal regions may be 5, 6, 7, 8, 9, 10, 11, 12, 13, 14, 15, 16, 17, 20, 25, 30, 35, 40, 41, or 45 amino acids in length.

SDF-1 analogs useful for the methods of the invention may include derivatives such as C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine residue is replaced with a phenethylamide analogue (e.g., Ser-Ile-phenethylamide as an analog of the tripeptide Ser-Ile-Phe), glycosylated chemokine derivatives, polyethylene glycol modified derivatives, or biotinylated derivatives.

The SDF-1 analogs useful for the methods of the invention may be coupled directly or indirectly to at least one modifying group. The term "modifying group" is intended to include structures that are directly attached to the peptidic structure (e.g., by covalent bonding or covalent coupling), as well as those that are indirectly attached to the peptidic structure (e.g., by a stable non-covalent bond association or by covalent coupling through a linker to additional amino acid residues). The term "modifying group" may also refer to mimetics, analogs or derivatives thereof, which may flank the SDF-1 core peptidic structure. For example, the modifying group can be coupled to the amino-terminus or carboxy-terminus of a SDF-1 peptidic structure, or to a peptidic or peptidomimetic region flanking the core structure. Alternatively, the modifying group can be coupled to a side chain of at least one amino acid residue of a SDF-1 peptidic structure, or to a peptidic or peptido-mimetic region flanking the core domain (e.g., through the epsilon amino group of a lysyl residue(s); through the carboxyl group of an aspartic acid residue(s) or a glutamic acid residue(s); through a hydroxy group of a tyrosyl residue(s), a serine residue(s) or a threonine residue(s); or any other suitable reactive group on an amino acid side chain). The modifying groups covalently coupled to the peptidic structure can be attached by means and using methods well known in the art for linking chemical structures, including, for example, amide, alkylamino, sulfide, carbamate or urea bonds.

In some embodiments, the modifying group may comprise a cyclic, heterocyclic or polycyclic group. The term "cyclic group," as used herein, includes cyclic saturated or unsaturated (i.e., aromatic) group having from 3 to 10; from 4 to 8; or 5, 6, or 7 carbon atoms. Exemplary non-aromatic cyclic groups include cyclopropyl, cyclobutyl, cyclopentyl, cyclohexyl, and cyclooctyl. The term "heterocyclic group" includes optionally substituted, saturated or unsaturated, three- to eight-membered cyclic structures in which one or more skeletal atoms is oxygen, nitrogen, sulfur, or combinations thereof. Cyclic groups or heterocyclic groups may be unsubstituted or substituted at one or more ring positions. A cyclic group may for example be substituted with halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN. The cyclic group may also be linked to a substituent, such as halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN by means of a saturated or unsaturated chain of 1, 2, 3, 4, 5, 6, 7, 8, or more carbon atoms; additionally one or more of the carbon atoms may be replaced with an oxygen, nitrogen, or sulfur atoms.

SDF-1 analogs useful for the methods of the invention may be modified by the addition of polyethylene glycol (PEG). PEG modification may lead to improved circulation time, improved solubility, improved resistance to proteolysis, reduced antigenicity and immunogenicity, improved bioavailability, reduced toxicity, improved stability, and easier formulation. PEGylation may also result in a substantial reduction in bioactivity.

SDF-1 analogs useful for the methods of the invention may be prepared in a "prodrug" form, wherein the compound itself does not act as a SDF-1 analog, but rather is capable of being transformed, upon metabolism in vitro and/or in vivo, into a SDF-1 analog. For example, in this type of compound, the modifying group can be present in a prodrug form that is capable of being converted upon metabolism into the form of an active SDF-1 analog. Such a prodrug form of a modifying group is referred to herein as a "secondary modifying group." A variety of strategies are known in the art for preparing peptide prodrugs that limit metabolism in order to optimize delivery of the active form of the peptide-based drug.

The various features and embodiments of the present invention, referred to in individual sections above apply, as appropriate, to other sections. In particular, features specified in one section may be combined with features specified in other sections, as appropriate.

Production of Genetically Modified Cells

In a further aspect of the invention, the MPC or precursors cells derived therefrom, are genetically modified to produce SDF-1, or peptide analogs thereof. Typically, the cells will be genetically modified such that SDF-1, or the peptide analog thereof, is secreted from the cells.

Genetically modified cells can be cultured in the presence of at least one cytokine in an amount sufficient to support growth of the modified cells. The modified cells are then selected wherein the encoded polypeptide is overexpressed. The genetically modified cells thus obtained may be used immediately (e.g., in transplant), cultured and expanded in vitro, or stored for later uses. The modified cells may be stored by methods well known in the art, e.g., frozen in liquid nitrogen.

Genetic modification as used herein encompasses any genetic modification method which involves introduction of an exogenous or foreign polynucleotide into a MPC or precursor cell derived therefrom or modification of an endogenous gene within a MPC or precursor cell derived therefrom. Genetic modification includes but is not limited to transduction (viral mediated transfer of host DNA from a host or donor to a recipient, either in vitro or in vivo), transfection (transformation of cells with isolated viral DNA genomes), liposome mediated transfer, electroporation, calcium phosphate transfection or coprecipitation and others. Methods of transduction include direct co-culture of cells with producer cells (Bregni et al., Blood 80:1418-1422, 1992) or culturing with viral supernatant alone with or without appropriate growth factors and polycations (Xu et al., Exp. Hemat. 22:223-230, 1994).

A polynucleotide encoding SDF-1, or a peptide analog thereof, is typically introduced to a host cell in a vector. The vector typically includes the necessary elements for the transcription and translation of the inserted coding sequence. Methods used to construct such vectors are well known in the art. For example, techniques for constructing suitable expression vectors are described in detail in Sambrook et al., Molecular Cloning: A Laboratory Manual, Cold Spring Harbor Press, N.Y. (3rd Ed., 2000); and Ausubel et al., Current Protocols in Molecular Biology, John Wiley & Sons, Inc., New York (1999).

Vectors may include but are not limited to viral vectors, such as retroviruses, adenoviruses, adeno-associated viruses, and herpes simplex viruses; cosmids; plasmid vectors; synthetic vectors; and other recombination vehicles typically used in the art. Vectors containing both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). Specific examples include, pSG, pSV2CAT, pXt1 from Stratagene; and pMSG, pSVL, pBPV and pSVK3 from Pharmacia.

Preferred vectors include retroviral vectors (see, Coffin et al., "Retroviruses", Chapter 9 pp; 437-473, Cold Springs Harbor Laboratory Press, 1997). Vectors useful in the invention can be produced recombinantly by procedures well known in the art. For example, WO94/29438, WO097/21824 and WO97/21825 describe the construction of retroviral packaging plasmids and packing cell lines. Exemplary vectors include the pCMV mammalian expression vectors, such as pCMV6b and pCMV6c (Chiron Corp.), pSFFV-Neo, and pBluescript-Sk+. Non-limiting examples of useful retroviral vectors are those derived from murine, avian or primate retroviruses. Common retroviral vectors include those based on the Moloney murine leukemia virus (MoMLV-vector). Other MoMLV derived vectors include, Lmily, LINGFER, MINGFR and MINT (Chang et al., Blood 92:1-11, 1998). Additional vectors include those based on Gibbon ape leukemia virus (GALV) and Moloney murine sarcoma virus (MOMSV) and spleen focus forming virus (SFFV). Vectors derived from the murine stem cell virus (MESV) include MESV-MiLy (Agarwal et al., J. of Virology, 72:3720-3728, 1998). Retroviral vectors also include vectors based on lentiviruses, and non-limiting examples include vectors based on human immunodeficiency virus (HIV-1 and HIV-2).

In producing retroviral vector constructs, the viral gag, pol and env sequences can be removed from the virus, creating room for insertion of foreign DNA sequences. Genes encoded by foreign DNA are usually expressed under the control a strong viral promoter in the long terminal repeat (LTR). Selection of appropriate control regulatory sequences is dependent on the host cell used and selection is within the skill of one in the art. Numerous promoters are known in addition to the promoter of the LTR. Non-limiting examples include the phage lambda PL promoter, the human cytomegalovirus (CMV) immediate early promoter; the U3 region promoter of the Moloney Murine Sarcoma Virus (MMSV), Rous Sacroma Virus (RSV), or Spleen Focus Forming Virus (SFFV); Granzyme A promoter, and the Granzyme B promoter. Additionally inducible or multiple control elements may be used. The selection of a suitable promoter will be apparent to those skilled in the art.

Such a construct can be packed into viral particles efficiently if the gag, pol and env functions are provided in trans by a packing cell line. Therefore, when the vector construct is introduced into the packaging cell, the gag-pol and env proteins produced by the cell, assemble with the vector RNA to produce infectious virons that are secreted into the culture medium. The virus thus produced can infect and integrate into the DNA of the target cell, but does not produce infectious viral particles since it is lacking essential packaging sequences. Most of the packing cell lines currently in use have been transfected with separate plasmids, each containing one of the necessary coding sequences, so that multiple recombination events are necessary before a replication competent virus can be produced. Alternatively the packaging cell line harbors a provirus. The provirus has been crippled so that although it may produce all the proteins required to assemble infectious viruses, its own RNA cannot be packaged into virus. RNA produced from the recombinant virus is packaged instead. Therefore, the virus stock released from the packaging cells contains only recombinant virus. Non-limiting examples of retroviral packaging lines include PA12, PA317, PE501, PG13, PSI.CRIP, RDI 14, GP7C-tTA-G10, ProPak-A (PPA-6), and PT67. Reference is made to Miller et al., Mol. Cell Biol. 6:2895, 1986; Miller et al., Biotechniques 7:980, 1989; Danos et al., Proc. Natl. Acad. Sci. USA 85:6460, 1988; Pear et al., Proc. Natl. Acad. Sci. USA 90:8392-8396, 1993; and Finer et al., Blood 83:43-50, 1994.

Other suitable vectors include adenoviral vectors (see, Frey et al., Blood 91:2781, 1998; and WO 95/27071) and adeno-associated viral vectors. These vectors are all well know in the art, e.g., as described in Chatterjee et al., Current Topics in Microbiol. And Immunol., 218:61-73, 1996; Stem cell Biology and Gene Therapy, eds. Quesenberry et al., John Wiley & Sons, 1998; and U.S. Pat. Nos. 5,693,531 and 5,691,176. The use of adenovirus-derived vectors may be advantageous under certain situation because they are not capable of infecting non-dividing cells. Unlike retroviral DNA, the adenoviral DNA is not integrated into the genome of the target cell. Further, the capacity to carry foreign DNA is much larger in adenoviral vectors than retroviral vectors. The adeno-associated viral vectors are another useful delivery system. The DNA of this virus may be integrated into non-dividing cells, and a number of polynucleotides have been successful introduced into different cell types using adeno-associated viral vectors.

In some embodiments, the construct or vector will include two or more heterologous polynucleotide sequences; a) the nucleic acid sequence encoding SDF-1 or a peptide analog thereof, and b) one or more additional nucleic acid sequence. Preferably the additional nucleic acid sequence is a polynucleotide which encodes a selective marker, a structural gene, a therapeutic gene, a CXCR4 receptor or a further cytokine/chemokine gene.

A selective marker may be included in the construct or vector for the purposes of monitoring successful genetic modification and for selection of cells into which DNA has been integrated. Non-limiting examples include drug resistance markers, such as G148 or hygromycin. Additionally negative selection may be used, for example wherein the marker is the HSV-tk gene. This gene will make the cells sensitive to agents such as acyclovir and gancyclovir. The NeoR (neomycin/G148 resistance) gene is commonly used but any convenient marker gene may be used whose gene sequences are not already present in the target cell can be used. Further non-limiting examples include low-affinity Nerve Growth Factor (NGFR), enhanced fluorescent green protein (EFGP), dihydrofolate reductase gene (DHFR) the bacterial hisD gene, murine CD24 (HSA), murine CD8a (lyt), bacterial genes which confer resistance to puromycin or phleomycin, and β-galactosidase.

The additional polynucleotide sequence(s) may be introduced into the host cell on the same vector as the polynucleotide sequence encoding SDF-1 or peptide analog thereof, or the additional polynucleotide sequence may be introduced into the host cells on a second vector. In a preferred embodiment, a selective marker will be included on the same vector as the polynucleotide encoding SDF-1 or peptide analog thereof.

The present invention also encompasses genetically modifying the promoter region of the endogenous SDF-1 gene such that expression of the endogenous gene is upregulated resulting in the increased production of SDF-1 compared to a wild type MPC or precursor cell derived therefrom.

Administration of Stromal Derived Factor-1 (SDF-1) and Analogs Thereof

Methods of the present invention may involve administration of SDF-1 or an analog thereof to a subject in order to enhance proliferation and/or survival of MPC or progeny derived therefrom in situ.

These methods may involve administering SDF-1 or an analog thereof topically, systematically, or locally such as within an implant or device.

In one particular embodiment the invention provides a method of enhancing proliferation and/or survival of MPC or progeny derived therefrom in a subject in need thereof by administering SDF-1 or an analog thereof systemically to the subject. For example, the SDF-1 or analog thereof may be administered by subcutaneous or intramuscular injection.

This embodiment of the invention may be useful for the treatment of systemic degenerative diseases where increased proliferation and/or survival of MPC in particular tissues is desirable. Examples of systemic degenerative diseases that can be treated in this way include osteoporosis or fractures, degenerative diseases of cartilage, atherosclerosis, peripheral artery diseases or cardiovascular diseases and the like.

Thus, according to the present invention, compositions comprising SDF-1 or an analog thereof in a therapeutically or prophylactically effective amount may be used in treating diseases or disorders selected from the group consisting of autoimmune diseases, acute chronic inflammation, cancer, cardiovascular disease, infectious disease, and inflammatory disorders including rheumatoid arthritis, chronic inflammatory bowel disease, chronic inflammatory pelvic disease, multiple sclerosis, asthma, osteoarthritis, atherosclerosis, psoriasis, rhinitis, autoimmunity, and organ transplant rejection. In one example, such compositions include SDF-1 or an analog thereof in a therapeutically or prophylactically effective amount sufficient to be used to assist in stimulating the production of tissue specific cells.

A "therapeutically effective amount" refers to an amount effective, at dosages and for periods of time necessary, to achieve enhanced proliferation and/or survival of MPC or progeny derived therefrom.

A "prophylactically effective amount" refers to an amount effective, at dosages and for periods of time necessary, to achieve the desired prophylactic result, such as preventing or inhibiting death of MPC or progeny derived therefrom.

In particular embodiments, a preferred range for therapeutically or prophylactically effective amounts of SDF-1 or an analog thereof may be 0.1 nM-0.1 M, 0.1 nM-0.05 M, 0.05 mM-15 µM or 0.01 nM-10 µM. It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners.

The amount of SDF-1 or an analog thereof in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier.

It will be appreciated that the SDF-1 or analog thereof may be administered in the form of a composition comprising a pharmaceutically acceptable carrier or excipient.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical formulations for parenteral administration may include liposomes. Liposomes and emulsions are well known examples of delivery vehicles or carriers that are especially useful for hydrophobic drugs. Depending on biological stability of the therapeutic reagent, additional strategies for protein stabilization may be employed. Furthermore, one may administer the drug in a targeted drug delivery system, for example, in a liposome coated with target-specific antibody. The liposomes will bind to the target protein and be taken up selectively by the cell expressing the target protein.

Therapeutic compositions typically should be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof.

The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition.

Prolonged absorption of the injectable compositions can be brought about by including in the composition an agent which delays absorption, for example, monostearate salts and gelatin. Moreover, the SDF-1 or analog thereof may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Additionally, suspensions of the compounds of the invention may be prepared as appropriate oily suspensions for injection. Suitable lipophilic solvents or vehicles include fatty oils such as sesame oil; or synthetic fatty acid esters, such as ethyl oleate or triglycerides; or liposomes. Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, SDF-1 or an analog thereof may be formulated with one or more additional compounds that enhance the solubility of the SDF-1 or analog.

If the compounds of the invention are to be administered by inhalation, they may be conveniently delivered in the form of an aerosol spray presentation from pressurized packs or a nebuliser; together with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin, for example, for use in an inhaler may be formulated containing a powder mix of the compound and a suitable powder base such as starch or lactose.

Administration of Cellular Compositions of the Present Invention

The cellular compositions of the present invention comprising MPC and/or progeny derived therefrom may be useful for the regeneration of tissue of various types, including bone, cartilage, tendon, ligament, muscle, skin, and other connective tissue, as well as nerve, cardiac, liver, lung, kidney, pancreas, brain, and other organ tissues.

In some embodiments, the compositions of the present invention may be administered in combination with an appropriate matrix, for instance, for supporting the MPC and/or progeny derived therefrom and providing a surface for bone, cartilage, muscle, nerve, epidermis and/or other connective tissue growth. The matrix may be in the form of traditional matrix biomaterials. The matrix may provide slow release of the expressed protein and differentiated cells and/or the appropriate environment for presentation thereof. In some embodiments, various collagenous and non-collagenous proteins are expected to be upregulated and secreted from the MPC or progeny derived therefrom. This phenomenon accelerates tissue regeneration by enhancing matrix deposition. Matrix proteins can also be expressed in the genetically engineered cells and enhance the engraftment and attachment of transplanted cells into the transplant area.

The choice of matrix material is based on biocompatibility, biodegradability, mechanical properties, cosmetic appearance and interface properties. The particular application of the cellular based compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

The cellular compositions of the invention may be used to treat patients requiring the repair or replacement of cartilage or bone tissue resulting from disease or trauma or failure of the tissue to develop normally, or to provide a cosmetic function, such as to augment facial or other features of the body. Treatment may entail the use of the cells of the invention to produce new cartilage tissue or bone tissue. For example, compositions comprising undifferentiated or chondrogenic differentiation-induced precursor cells may be used to treat a cartilage condition, for example, rheumatoid arthritis or osteoarthritis or a traumatic or surgical injury to cartilage. As another example, compositions comprising bone precursor cells may be used to treat bone conditions, including metabolic and non-metabolic bone diseases. Examples of bone conditions include meniscal tears, spinal fusion, spinal disc removal, spinal reconstruction, bone fractures, bone/spinal deformation, osteosarcoma, myeloma, bone dysplasia, scoliosis, osteoporosis, periodontal disease, dental bone loss, osteomalacia, rickets, fibrous osteitis, renal bone dystrophy, and Paget's disease of bone.

The cellular compositions of the invention may be administered alone or as admixtures with other cells. Cells that may be administered in conjunction with the compositions of the present invention include, but are not limited to, other multipotent or pluripotent cells or chondrocytes, chondroblasts, osteocytes, osteoblasts, osteoclasts, bone lining cells, stem cells, or bone marrow cells. The cells of different types may be admixed with a composition of the invention immediately or shortly prior to administration, or they may be co-cultured together for a period of time prior to administration.

The cellular compositions of the invention may be administered with other beneficial drugs or biological molecules (growth factors, trophic factors). When the MPC and/or progeny derived therefrom are administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics. As another example, the cells may be co-administered with scar inhibitory factor as described in U.S. Pat. No. 5,827,735, incorporated herein by reference.

In one embodiment, cellular compositions of the invention are administered as undifferentiated cells, i.e., as cultured in Growth Medium. Alternatively, the cellular compositions may be administered following exposure in culture to conditions that stimulate differentiation toward a desired phenotype, for example, an osteogenic phenotype.

The cellular compositions of the invention may be surgically implanted, injected, delivered (e.g., by way of a catheter or syringe), or otherwise administered directly or indirectly to the site in need of repair or augmentation. The cells may be administered by way of a matrix (e.g., a three-dimensional scaffold). The cells may be administered with conventional pharmaceutically acceptable carriers. Routes of administration of the cells of the invention or compositions or components (e.g., ECM, cell lysate, conditioned medium) thereof include intramuscular, ophthalmic, parenteral (including intravenous), intraarterial, subcutaneous, oral, and nasal administration. Particular routes of parenteral administration include, but are not limited to, intramuscular, subcutaneous, intraperitoneal, intracerebral, intraventricular, intracerebroventricular, intrathecal, intracisternal, intraspinal and/or peri-spinal routes of administration.

When cells are administered in semi-solid or solid devices, surgical implantation into a precise location in the body is typically a suitable means of administration. Liquid or fluid pharmaceutical compositions, however, may be administered to a more general location (e.g., throughout a diffusely affected area, for example), from which they migrate to a particular location, e.g., by responding to chemical signals.

Other embodiments encompass methods of treatment by administering pharmaceutical compositions comprising cellular components (e.g., cell lysates or components thereof) or products (e.g., extracellular matrix, trophic and other biological factors produced through genetic modification).

Dosage forms and regimes for administering cellular compositions described herein are developed in accordance with good medical practice, taking into account the condition of the individual patient, e.g., nature and extent of the condition being treated, age, sex, body weight and general medical condition, and other factors known to medical practitioners. Thus, the effective amount of a pharmaceutical composition to be administered to a patient is determined by these considerations as known in the art.

In some embodiments of the invention, it may not be necessary or desirable to immunosuppress a patient prior to initiation of therapy with cellular compositions of the present invention. Accordingly, transplantation with allogeneic, or even xenogeneic, MPC or progeny derived therefrom may be tolerated in some instances.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. MPC or progeny derived therefrom may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, MPC or progeny derived therefrom may be genetically modified to reduce their immunogenicity.

Survival of transplanted MPC or progeny derived therefrom in a living patient can be determined through the use of a variety of scanning techniques, e.g., computerized axial tomography (CAT or CT) scan, magnetic resonance imaging (MRI) or positron emission tomography (PET) scans. Determination of transplant survival can also be done post mortem by removing the target tissue, and examining it visually or through a microscope. Alternatively, cells can be treated with stains that are specific for cells of a specific lineage. Transplanted cells can also be identified by prior incorporation of tracer dyes such as rhodamine- or fluorescein-labeled microspheres, fast blue, bisbenzamide, ferric microparticles, or genetically introduced reporter gene products, such as beta-galactosidase or beta-glucuronidase.

Functional integration of transplanted MPC or progeny derived therefrom into a subject can be assessed by examining restoration of the function that was damaged or diseased, for example, restoration of joint or bone function, or augmentation of function.

Cellular compositions of the invention may include one or more bioactive factors, for example but not limited to a growth factor, a differentiation-inducing factor, a cell survival factor such as caspase inhibitor, an anti-inflammatory agent such as p38 kinase inhibitor, or an angiogenic factor such as VEGF or bFGF. Some examples of bioactive factors include PDGF-bb, EGF, bFGF, IGF-1, and LIF.

Alternatively, MPC or progeny derived therefrom to be transplanted may be genetically engineered to express such growth factors, antioxidants, antiapoptotic agents, anti-inflammatory agents, or angiogenic factors.

Pharmaceutical compositions of the invention may comprise homogeneous or heterogeneous populations of MPC or progeny derived therefrom, extracellular matrix or cell lysate thereof, or conditioned medium thereof in a pharmaceutically acceptable carrier. Pharmaceutically acceptable carriers for the cells of the invention include organic or inorganic carrier substances suitable which do not deleteriously react with the cells of the invention or compositions or components thereof. To the extent they are biocompatible, suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences (17.sup.th Ed., Mack Pub. Co., Easton, Pa.) and WO 96/05309, each of which are incorporated by reference herein.

One or more other components may be added to transplanted cells, including selected extracellular matrix components, such as one or more types of collagen known in the art, and/or growth factors, platelet-rich plasma, and drugs. Alternatively, the cells of the invention may be genetically engineered to express and produce for growth factors. Details on genetic engineering of the cells of the invention are provided herein.

In a non-limiting embodiment, a formulation comprising the cells of the invention is prepared for administration directly to the site where the production of new tissue, such as bone tissue, is desired. For example, and not by way of limitation, the MPC or progeny derived therefrom may be suspended in a hydrogel solution for injection. Examples of suitable hydrogels for use in the invention include self-assembling peptides, such as RAD16. Alternatively, the hydrogel solution containing the cells may be allowed to harden, for instance in a mold, to form a matrix having cells dispersed therein prior to implantation. Or, once the matrix has hardened, the cell formations may be cultured so that the cells are mitotically expanded prior to implantation. The hydrogel is an organic polymer (natural or synthetic) which is cross-linked via covalent, ionic, or hydrogen bonds to create a three-dimensional open-lattice structure which entraps water molecules to form a gel. Examples of materials which can be used to form a hydrogel include polysaccharides such as alginate and salts thereof, peptides, polyphosphazines, and polyacrylates, which are crosslinked ionically, or block polymers such as polyethylene oxide-polypropylene glycol block copolymers which are cross-linked by temperature or pH, respectively. In some embodiments, the support for the MPC or progeny derived therefrom is biodegradable.

In some embodiments of the invention, the formulation comprises an in situ polymerizable gel, as described, for example, in U.S. Patent Application Publication 2002/0022676; Anseth et al., J. Control Release, 78(1-3): 199-209 (2002); Wang et al., Biomaterials, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)] phosphazene (PCPP) can be synthesized, which is crosslinked with dissolved multivalent cations in aqueous media at room temperature or below to form hydrogel matrices.

Biodegradable polyphosphazenes have at least two differing types of side chains, acidic side groups capable of forming salt bridges with multivalent cations, and side groups that hydrolyze under in viva conditions, e.g., imidazole groups, amino acid esters, glycerol and glucosyl.

Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom, Other "R" groups can be organic residues that do not participate in hydrolysis, such as methyl phenoxy groups or other groups shown in the scientific paper of Allcock et al., Macromolecule 10:824 (1977). Methods of synthesis of the hydrogel materials, as well as methods for preparing such hydrogels, are known in the art.

Other components may also be included in the formulation, including but not limited to any of the following: (1) buffers to provide appropriate pH and isotonicity; (2) lubricants; (3) viscous materials to retain the cells at or near the site of administration, including, for example, alginates, agars and plant gums; and (4) other cell types that may produce a desired effect at the site of administration, such as, for example, enhancement or modification of the formation of tissue or its physicochemical characteristics, or as support for the viability of the cells, or inhibition of inflammation or rejection. The cells may be covered by an appropriate wound covering to prevent cells from leaving the site. Such wound coverings are known as those of skill in the art.

Formulation of a Bone Tissue Patch

Culture or co-cultures of MPC or progeny derived therefrom in a pre-shaped well enables the manufacture of a tissue patch of pre-determined thickness and volume. The volume of the resulting tissue patch is dependent upon the volume of the well and upon the number of MPC or progeny derived therefrom in the well. Tissue of optimal pre-determined volume may be prepared by routine experimentation by altering either or both of the aforementioned parameters.

The cell contacting surface of the well may be coated with a molecule that discourages adhesion of MPC or progeny derived therefrom to the cell contacting surface. Preferred coating reagents include silicon based reagents i.e., dichlorodimethylsilane or polytetrafluoroethylene based reagents, i.e., TEFLON. Procedures for coating materials with silicon based reagents, specifically dichlorodimethylsilane, are well known in the art. See for example, Sambrook et al. (1989) "Molecular Cloning A Laboratory Manual", Cold Spring Harbor Laboratory Press, the disclosure of which is incorporated by reference herein. It is appreciated that other biocompatible reagents that prevent the attachment of cells to the surface of the well may be useful in the practice of the instant invention.

Alternatively, the well may be cast from a pliable or moldable biocompatible material that does not permit attachment of cells per se. Preferred materials that prevent such cell attachment include, but are not limited to, agarose, glass, untreated cell culture plastic and polytetrafluoroethylene, i.e., TEFLON. Untreated cell culture plastics, i.e., plastics that have not been treated with or made from materials that have an electrostatic charge are commercially available, and may be purchased, for example, from Falcon Labware, Becton-Dickinson, Lincoln Park, N.J. The aforementioned materials, however, are not meant to be limiting. It is appreciated that any other pliable or moldable biocompatible material that inherently discourages the attachment of MPC or progeny derived therefrom may be useful in the practice of the instant invention.

MPC or progeny derived therefrom in suspension may be seeded into and cultured in the pre-shaped well. The MPC or progeny derived therefrom may be induced to differentiate to a chondrogenic or osteogenic phenotype in culture in the well or may have been induced to differentiate prior to seeding in the well. The cells may be diluted by the addition of culture medium to a cell density of about $1 \times 10^5$ to $1 \times 10^9$ cells per milliliter.

The cells may form a cohesive plug of cells. The cohesive plug of cells may be removed from the well and surgically implanted into the tissue defect. It is anticipated that undifferentiated MPC or progeny derived therefrom may differentiate in situ thereby to form tissue in vivo.

Bone defects may be identified inferentially by using computer aided tomography (CAT scanning); X-ray examination, magnetic resonance imaging (MRI), analysis of synovial fluid or serum markers or by any other procedures known in the art. Defects in mammals also are readily identifiable visually during arthroscopic examination orduring open surgery of the joint. Treatment of the defects can be effected during an arthroscopic or open surgical procedure using the methods and compositions disclosed herein.

Accordingly, once the defect has been identified, the defect may be treated by the following steps of (1) surgically implanting at the pre-determined site a tissue patch prepared by the methodologies described herein, and (2) permitting the tissue patch to integrate into pre-determined site.

The tissue patch optimally has a size and shape such that when the patch is implanted into the defect, the edges of the implanted tissue contact directly the edges of the defect. In addition, the tissue patch may be fixed in place during the surgical procedure. This can be effected by surgically fixing the patch into the defect with biodegradable sutures and/or by applying a bioadhesive to the region interfacing the patch and the defect.

In some instances, damaged tissue may be surgically excised prior to the implantation of the patch of tissue.

Transplantation of MPC or Progeny Derived Therefrom Using Scaffolds

The cellular compositions of the invention or co-cultures thereof may be seeded onto or into a three-dimensional scaffold and implanted in vivo, where the seeded cells will proliferate on the framework and form a replacement tissue, such as bone tissue, in vivo in cooperation with the cells of the patient.

For example, but not by way of limitation, the scaffold may be designed such that the scaffold structure: (1) supports the seeded cells without subsequent degradation; (2) supports the cells from the time of seeding until the tissue transplant is remodeled by the host tissue; (2) allows the seeded cells to attach, proliferate, and develop into a tissue structure having sufficient mechanical integrity to support itself in vitro, at which point, the scaffold is degraded. A review of scaffold design is provided by Hutmacher, J. Biomat. Sci. Polymer Edn., 12(1):107-124 (2001).

Scaffolds of the invention can be administered in combination with any one or more growth factors, cells, for example stem cells, bone marrow cells, chondrocytes, chondroblasts, osteocytes, osteoblasts, osteoclasts, bone lining cells, or their precursors, drugs or other components described above that stimulate tissue formation or otherwise enhance or improve the practice of the invention. The MPC or progeny derived therefrom to be seeded onto the scaffolds may be genetically engineered to express growth factors or drugs.

The cells of the invention can be used to produce new tissue in vitro, which can then be implanted, transplanted or otherwise inserted into a site requiring tissue repair, replacement or augmentation in a patient.

In a non-limiting embodiment, the cells of the invention are used to produce a three-dimensional tissue construct in vitro, which is then implanted in vivo. As an example of the production of three-dimensional tissue constructs, see U.S. Pat. No. 4,963,489, which is incorporated herein by reference. For example, the cells of the invention may be inoculated or "seeded" onto a three-dimensional framework or scaffold, and proliferated or grown in vitro to form a living tissue that can be implanted in vivo.

The cells of the invention can be grown freely in a culture vessel to sub-confluency or confluency, lifted from the culture and inoculated onto a three-dimensional framework. Inoculation of the three-dimensional framework with a high concentration of cells, e.g., approximately $10^6$ to $5 \times 10^7$ cells per milliliter, will result in the establishment of the three-dimensional support in relatively shorter periods of time.

Examples of scaffolds which may be used in the present invention include nonwoven mats, porous foams, or self assembling peptides. Nonwoven mats may, for example, be formed using fibers comprised of a synthetic absorbable copolymer of glycolic and lactic acids (PGA/PLA), sold under the tradename VICRYL (Ethicon, Inc., Somerville, N.J.). Foams, composed of, for example, poly(epsilon-caprolactone)/poly(glycolic acid) (PCL/PGA) copolymer, formed by processes such as freeze-drying, or lyophilized, as discussed in U.S. Pat. No. 6,355,699, are also possible scaffolds. Hydrogels such as self-assembling peptides (e.g., RAD16) may also be used. These materials are frequently used as supports for growth of tissue.

The three-dimensional framework may be made of ceramic materials including, but not limited to: mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS (University of Florida, Gainesville, Fla.), and mixtures thereof. There are a number of suitable porous biocompatible ceramic materials currently available on the commercial market such as SURGIBON (Unilab Surgibone, Inc., Canada), ENDOBON (Merck Biomaterial France, France), CEROS (Mathys, A. G., Bettlach, Switzerland), and NTERPORE (Interpore, Irvine, Calif., United States), and mineralized collagen bone grafting products such as HEALOS (Orquest, Inc., Mountain View, Calif.) and VITOSS, RHAKOSS, and CORTOSS (Orthovita, Malvern, Pa.). The framework may be a mixture, blend or composite of natural and/or synthetic materials. In some embodiments, the scaffold is in the form of a cage. In a preferred embodiment, the scatfold is coated with collagen.

According to a preferred embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling.

In another preferred embodiment the cells of the invention are seeded onto foam scaffolds that may be composite structures. In addition, the three-dimensional framework may be molded into a useful shape, such as that of the external portion of the ear, a bone, joint or other specific structure in the body to be repaired, replaced or augmented.

In another preferred embodiment, the cells are seeded onto a framework comprising a prosthetic device for implantation into a patient, as described in U.S. Pat. No. 6,200,606, incorporated herein by reference. As described therein, a variety of clinically useful prosthetic devices have been developed for use in bone and cartilage grafting procedures. (see e.g. Bone Grafts and Bone Substitutions. Ed. M. B. Habal & A. H. Reddi, W. B. Saunders Co., 1992). For example, effective knee and hip replacement devices have been and continue to be widely used in the clinical environment. Many of these devices are fabricated using a variety of inorganic materials having low immunogenic activity, which safely function in the body. Examples of synthetic materials which have been tried and proven include titanium alloys, calcium phosphate, ceramic hydroxyapatite, and a variety of stainless steel and cobaltchrome alloys. These materials provide structural support and can form a scaffolding into which host vascularization and cell migration can occur.

The framework may be treated prior to inoculation of the cells of the invention in order to enhance cell attachment. For example, prior to inoculation with the cells of the invention, nylon matrices could be treated with 0.1 molar acetic acid and incubated in polylysine, PBS, and/or collagen to coat the nylon. Polystyrene could be similarly treated using sulfuric acid.

In addition, the external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In some embodiments, the scaffold is comprised of or is treated with materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PURSPAN (The Polymer Technology Group, Inc., Berkeley, Calif.). These materials can be further treated to render the scaffold non-thrombogenic. Such treatments include anti-thrombotic agents such as heparin, and treatments which alter the surface charge of the material such as plasma coating.

In some embodiments, the surface of the scaffold is textured. For example, in some aspects of the invention, the scaffold is provided with a groove and ridge pattern. The grooves are preferably less than about 500 microns, more preferably less than about 100 microns, and most preferably between about 10 nanometers and 10 microns. Such "microgrooves" allow the cells to align and/or migrate guided by the surface grooves.

In some embodiments, it is important to re-create in culture the cellular microenvironment found in vivo, such that the extent to which the cells of the invention are grown prior to implantation in vivo or use in vitro may vary. In addition, growth factors, chondrogenic differentiation inducing agents, osteogenic inducing agents, and angiogenic factors may be added to the culture medium prior to, during, or subsequent to inoculation of the cells to trigger differentiation and tissue formation by the MPC or progeny derived therefrom or co-cultures thereof.

The three-dimensional framework may be modified so that the growth of cells and the production of tissue thereon is enhanced, or so that the risk of rejection of the implant is reduced. Thus, one or more biologically active compounds, including, but not limited to, anti-inflammatories, immunosuppressants or growth factors, may be added to the framework.

Therapeutic Uses for Extracellular Matrix or Cell Lysates.

As an alternative to implanting the cells of the invention, or living tissue produced therefrom, a subject in need of tissue repair, replacement, or augmentation may benefit from the administration of a component or product of MPC or progeny derived therefrom (particularly where they have been genetically modified), such as the extracellular matrix (ECM) or cell lysate produced by those cells.

In some embodiments, after the cells of the invention have been cultured in vitro, such as, for example, by using a three-dimensional scaffold system described herein, such that a desired amount of ECM has been secreted onto the framework. Once ECM is secreted onto the framework, the cells may be removed. The ECM may be processed for further use, for example, as an injectable preparation.

In some embodiments, the cells are killed and cellular debris (e.g., cellular membranes) is removed from the framework. This process may be carried out in a number of different ways. For example, the living tissue can be flash-frozen in liquid nitrogen without a cryopreservative, or the tissue can be immersed in sterile distilled water so that the cells burst in response to osmotic pressure. Once the cells have been killed, the cellular membranes may be disrupted and cellular debris removed by treatment with a mild detergent rinse, such as EDTA, CHAPS or a zwitterionic detergent. An advantage to using a mild detergent rinse is that it solubilizes membrane-bound proteins, which are often highly antigenic.

Alternatively, the tissue can be enzymatically digested and/or extracted with reagents that break down cellular membranes. Example of such enzymes include, but are not limited to, hyaluronidase, dispase, proteases, and nucleases (for example, deoxyribonuclease and ribonuclease). Examples of detergents include non-ionic detergents such as, for example; alkylaryl polyether alcohol (TRITON™ X-100), octylphenoxy polyethoxy-ethanol (Rohm and Haas Philadelphia, Pa.), BRIJ-35, a polyethoxyethanol lauryl ether (Atlas Chemical Co., San Diego, Calif.), polysorbate 20 (TWEEN 20™), a polyethoxyethanol sorbitan monolaureate (Rohm and Haas), polyethylene lauryl ether (Rohm and Haas); and ionic detergents such as, for example, sodium dodecyl sulphate, sulfated higher aliphatic alcohols, sulfonated alkanes and sulfonated alkylarenes containing 7 to 22 carbon atoms in a branched or unbranched chain.

Scaffolds comprising the ECM may be used therapeutically as described above. Alternatively, ECM may be collected from the scaffold. The collection of the ECM can be accomplished in a variety of ways, depending, for example, on whether the scaffold is biodegradable or non-biodegradable. For example, if the framework is non-biodegradable, the ECM can be removed by subjecting the framework to sonication, high pressure water jets, mechanical scraping, or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM can be processed in toto for subsequent injection. Alternatively, the ECM can be removed from the biodegradable framework by any of the methods described above for collection of ECM from a non-biodegradable framework. All collection processes are preferably designed so as not to denature the ECM or cell lysate produced by the cells of the invention.

Embodiments of the present invention will now be described in detail with reference to the following non-limiting examples.

EXAMPLES

Materials and Methods
Subjects and Cell Culture.

Bone marrow (BM) aspirates were obtained from the posterior iliac crest of healthy adult volunteers (19-35 years old) following informed consent, according to procedures approved by the ethics committee of the Royal Adelaide Hospital, South Australia. Bone marrow mononuclear cells (BMMNCs) were prepared as previously described (Gronthos et al. J Cell Sci. 116: 1827-1835, 2003). Primary BMSSC cultures were established in α-MEM (Minimum Essential Media) supplemented with 20% fetal calf serum, 2 mM L-glutamine, and 100 µM L-ascorbate-2-phosphate as previously described (Gronthos et al. J Cell Sci. 116: 1827-1835, 2003). BMSSC clonal cell lines were generated by limiting dilution from day 14 colonies derived from STRO-$1^{bri}$/VCAM-$1^+$ sorted cells as described below, following subculture in serum replete medium for proliferation, RT-PCR, imunohistochemistry, and developmental studies.

Magnetic-Activated Cell Sorting (MACS).

This was performed as previously described (Gronthos et al., Isolation, Purification and In Vitro Manipulation of Human Bone Marrow Stromal Precursor Cells. In Marrow Stromal Cell Culture. Owen M. and Beresford J. N. (eds). Cambridge University Press UK, Chapter 3, p. 26-42, 1998; Gronthos and Simmons, Blood 85(4): 929-940, 1995). In brief, approximately $1-3 \times 10^8$ normal human bone marrow mononuclear cells were sequentially incubated with STRO-1 supernatant, anti-IgM-biotin, streptavidin microbeads and finally streptavidin FITC (Caltag Laboratories, Burlingame, Calif.) before being separated on a Mini MACS magnetic column (Miltenyi Biotec Inc., Auburn, Calif.) according to the manufacturers instructions.

Fluorescence-Activated Cell Sorting (FACS).

The STRO-$1^+$ MACS isolated cells were labelled with streptavidin conjugated FITC, then incubated with either purified anti-CD106 (VCAM-1) antibody 6010 or anti-CD146 (MUC-18) antibody or isotype control 1B5 (10 µg/ml) for 30 minutes on ice, washed and incubated with phycoerythrin (PE) conjugated goat anti-mouse IgG antibody (1/50; Southern Biotechnology Associates, Birmingham, Ala.) for an additional 20 minutes on ice. Cells were sorted using a FACStar$^{PLUS}$ flow cytometer (Becton Dickinson, Sunnyvale, Calif.). The STRO-$1^{bri}$/CD106$^+$ or STRO-$1^{bri}$/CD146$^+$ cells were cultured in alpha-Modification of Eagle's Medium supplemented with 20% fetal calf serum, L-glutamine 2 mM, ascorbate-2-phosphate (100 µM) to initiate primary culture in 5% $CO_2$, at 37° C. humidified atmosphere.

Two-Colour Flow Cytometric Analysis using Indirect Immuofluorescence.

This procedure has been reported previously (Gronthos et al., Isolation, Purification and In Vitro Manipulation of Human Bone Marrow Stromal Precursor Cells. In Marrow Stromal Cell Culture. Owen M. and Beresford J. N. (eds). Cambridge University Press UK, Chapter 3, p. 26-42, 1998). Briefly, primary cultures of MPC or MPC derived cells were liberated by trypsin/EDTA digest then incubated for 30 min on ice. Approximately $2 \times 10^5$ cells were washed then resuspended in 200 µl of primary antibody cocktail for 1 hr on ice. The primary antibody cocktail consisted of saturating concentrations of the mouse IgM monoclonal antibody STRO-1 and a mouse IgG monoclonal antibody or rabbit IgG for each tube (Table 1). For the staining with antibodies reactive with intracellular antigens the cells were first washed with PBS then permeablized by treatment with 70% ethanol on ice for ten minutes then washed prior to staining. The mouse isotype IgM and IgG negative control Mabs were treated under the same conditions. Following incubation with primary antibodies, cells were washed and exposed to saturating levels of goat anti-mouse IgM µ-chain specific-FITC (1/50 dilution) and either goat anti-mouse IgG γ-specific-PE (1/50 dilution) or anti-rabbit Ig-specific-PE (1/50 dilution) (Southern Biotechnology Associates) in a final volume of 100 µl. The cells were incubated for 45 min on ice, then washed twice then fixed in FAX FIX (PBS supplemented with 1% (v/v), 2% (w/v) D-glucose, 0.01% sodium azide). The cells were then analysed on an Epics®-XL-MCL flow cytometer (Beckman Coulter, Hialeah, Fla.).

Carboxyfluorescein Diacetate Succinimidyl Ester (CFSE) Labelling.

The cell-permeant fluorescein-based dye CFSE was used to study division-related phenotypic and functional changes during MPC derived cell development. CFSE covalently attaches to cytoplasmic components of cells, resulting in uniform bright fluorescence, which upon cell division is equally distributed between daughter cells. This technique allows the resolution of up to eight cycles of cell division by flow cytometry. Single cell suspensions of ex vivo expanded MPC derived cells were washed once, resuspended in 1 ml of PBS/0.1% BSA and 2 µl of 5 mM CFSE (final 10 µM) was added prior to incubating at 37° C. for 10 mins. The staining was quenched by the addition of 5 volumes of ice cold culture medium α-MEM-10 and incubated on ice for 5 mins. The cells were washed three times in the culture medium and then plated at low density $1 \times 10^5$ in culture flasks (T-25). At various time points, cells were detached by trypsin-EDTA and analysed by flow cytometric analysis.

Reverse Transcriptase Polymerase Chain Reaction (RT-PCR) Analysis.

Primary MPC derived cultures were liberated by trypsin/EDTA treatment then stained with STRO-1 supernatant as described above. Following washing the cells were incubated with phycoerythrin (PE) conjugated goat anti-mouse IgM antibody (1/50; Southern Biotechnology Associates, Birmingham, Ala.) for an additional 20 minutes on ice. Cells were sorted using a FACStar$^{PLUS}$ flow cytometer (Becton Dickinson, Sunnyvale, Calif.). Total cellular RNA was prepared from either $2 \times 10^6$ STRO-$1^{bri}$ or STRO-$1^{dim}$ sorted primary cells, chondrocyte pellets and other induced cultures and lysed using RNAzolB extraction method (Biotecx Lab. Inc., Houston, Tex.), according to the manufacturer's recommendations. RNA isolated from each subpopulation was then used as a template for cDNA synthesis, prepared using a First-strand cDNA synthesis kit (Pharmacia Biotech, Uppsala, Sweden). The expression of various transcripts was assessed by PCR amplification, using a standard protocol as described previously (Gronthos et al., J. Bone and Min. Res. 14:48-57, 1999). Primers sets used in this study are shown in Table 2. Following amplification, each reaction mixture was analysed by 1.5% agarose gel electrophoresis, and visualised by ethidium bromide staining. RNA integrity was assessed by the expression of GAPDH.

Differentiation of CFU-F In Vitro.

We have previously reported the conditions for the induction of human BM stromal cells to develop a mineralized bone matrix in vitro cultured in αMEM supplemented with 10% FCS, 100 µM L-ascorbate-2-phosphate, dexamethasone $10^{-7}$ M and 3 mM inorganic phosphate (Gronthos et al., Blood. 84: 4164-4173, 1994). Mineral deposits were identified by positive von Kossa staining. Adipogenesis was induced in the presence of 0.5 mM methylisobutylmethylxanthine, 0.5 µM hydrocortisone, and 60 µM indomethacin as previously described (Gimble, J. M. Marrow stromal adipocytes. In *Marrow stromal cell culture*. Owen M. and Beresford J. N. (eds). Cambridge: Cambridge University Press UK. Chapter 5, p. 67-87, 1998). Oil Red O staining was used to identify lipid-laden fat cells. Chondrogenic differentiation was assessed in aggregate cultures treated with 10 ng/ml TGF-β3 as described (Pittenger et al., Science, 284:143-147, 1999).

In Vivo Assay of Bone Formation.

The adherent cells derived from STRO-1$^{bri}$/VCAM-1$^+$ cells at passage 2-3 were trypsinised, mixed with 40 mg hydroxyapatite/tricalcium phosphate ceramic particles (Zimmer Corporation, Warsaw, Ind.) and then implanted into subcutaneous pockets on the dorsal surface of two month old SCID mice as described previously (Gronthos et al., Proceedings of the National Academy of Sciences (USA), 97 (25): 13625-13630, 2000). These procedures were performed in accordance to specifications of an approved animal protocol (Adelaide University AEC# M/079/94). Implants were recovered after 6-8 weeks, fixed in 4% paraformaldehyde for 2 days, then decalcified for a further ten days in 10% EDTA prior to embedding in paraffin. For histological analysis, 5 μm sections of the implants were prepared and stained with haematoxylin and eosin (Gronthos et al., Proceedings of the National Academy of Sciences (USA), 97 (25): 13625-13630, 2000).

Neural Tissue Development.

Monolayer cultures are grown in Neuroblast A medium (Invitrogen/GIBCO)+5% horse serum, 1% fetal calf serum, L-glutamine (2 mM), transferrin (100 μg/ml), insulin (2 μg/ml), retinoic acid 0.5 mM, brain-derived neurothrophic factor (10 ng/ml).

Fat Development.

Monolayer cultures are grown in alpha-Modification of Eagle's Medium (JRI) supplemented with 10% fetal calf serum, L-glutamine 2 mM, ascorbate-2-phosphate (100 μM), 0.5 mM methylisobutylxanthine, 0.5 mM hydrocortisone, 60 mM indomethicin.

Cartilage Development:

Pellet cultures in polypropylene tubes are grown in alpha-Modification of Eagle's Medium supplemented with 1% bovine serum albumin, transferrin (100 μg/ml), insulin (2 μg/ml), L-glutamine (2 mM), ascorbate-2-phosphate (100 μM/ml), dexamethasone ($10^{-8}$M), with BMP-7 (50 ng/ml), TGFβ$_3$ (10 ng/ml).

Skeletal/Cardiac Muscle Development.

Monolayer cultures are grown in alpha-Modification of Eagle's Medium supplemented with 10% fetal calf serum, L-glutamine (2 mM), ascorbate-2-phosphate (100 μM/ml), and 5-azacytodine (5 μM/ml).

Epithelial Development.

Monolayer cultures are grown in keratinocyte basal medium (Clontenics) supplemented with Bovine Pituitary Extract (50 μg/ml), epidermal growth factor (10 ng/ml), Hydrocortisone (0.5 μg/ml), Insulin (5 μg/ml).

Osteoblasts, Tendon, Ligament or Odontoblast Development.

Monolayer cultures are grown in alpha-Modification of Eagle's Medium supplemented with 10% fetal calf serum, L-glutamine 2 mM, ascorbate-2-phosphate (100 μM), Dexamethasone ($10^{-7}$M) and BMP-2 (50 ng/ml)

Pericyte or Smooth Muscle Cell Development.

Cultures of 20,000 ex vivo cultured MPCs per well are grown in alpha-Modification of Eagle's Medium supplemented with 10% fetal calf serum, L-glutamine 2 mM, ascorbate-2-phosphate (100 μM), platelet derived growth factor-BB (10 ng/ml) suspended over 200 l of matrigel in 48-well plates.

Primary Antibodies.

Primary antibodies used in this study were as follows: STRO-1 (mouse IgM [immunoglobulin M]) (Gronthos et al. J Cell Sci. 116: 1827-1835, 2003), anti-human alkaline phosphatase antibody (B4-78, mouse IgG1; Hybridoma Studies Bank, University of Iowa, Ames), anti-human CXCR4 antibody (mouse IgG2b; Chemicon International, Temecula, Calif.), and anti-human annexin V antibody (mouse IgG1; Chemicon) were used as either tissue culture supernatant diluted 1:2 or as purified immunoglobulin 10 μg/mL, respectively. Isotype-matched control mouse monoclonal antibodies used in this study included 1A6.12 (IgM), 1B5 (IgG1), and 1A6.11 (IgG2b) (kindly provided by Prof L. K. Ashman, University of Newcastle, NSW, Australia).

Purification of BMSSCs.

Figure 1:
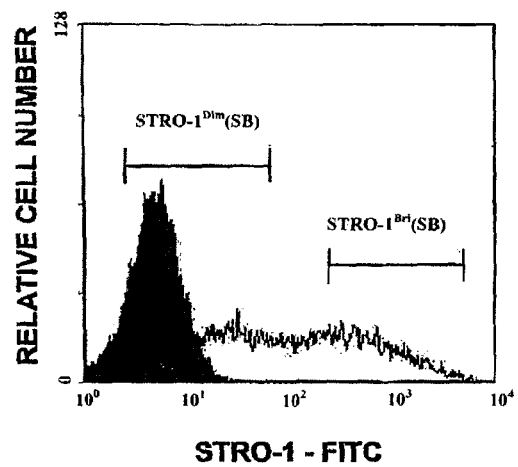
FIG. 1. Gene expression profile of STRO-1$^{bri}$ or STRO-1$^{dim}$ expressing cells derived from cultured MPC. Single cell suspensions of ex vivo expanded bone marrow MPC were prepared by trypsin/EDTA treatment. Cells were stained with the STRO-1 antibody which was subsequently revealed by incubation with goat-anti murine IgM-fluorescein isothiocyanate. Total cellular RNA was prepared from purified populations of STRO-1$^{dim}$ or STRO-1$^{bri}$ expressing cells, following fluorescence activated cell sorting (A). Using RNAzolB extraction method, and standard procedures, total RNA was isolated from each subpopulation and used as a template for cDNA synthesis. The expression of various transcripts was assessed by PCR amplification, using a standard protocol as described previously (Gronthos et al. J Cell Sci. 116:1827-1835, 2003). Primers sets used in this study are shown in Table 2. Following amplification, each reaction mixture was analysed by 1.5% agarose gel electrophoresis, and visualised by ethidium bromide staining (B). Relative gene expression for each cell marker was assessed with reference to the expression of the house-keeping gene, GAPDH, using ImageQant software (C).
Figure 1:
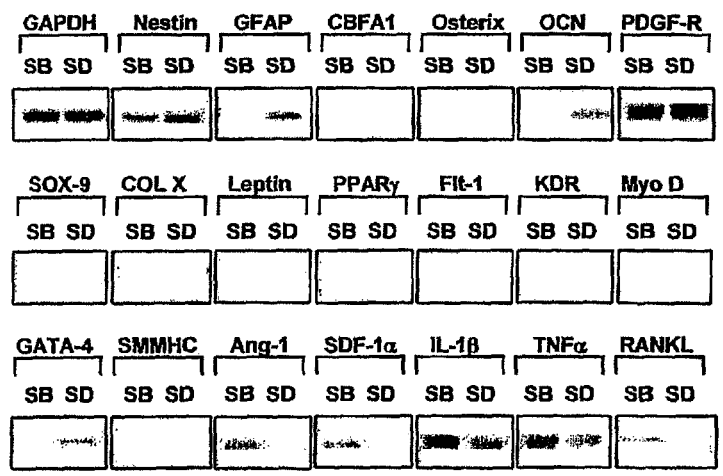
Figure 1:
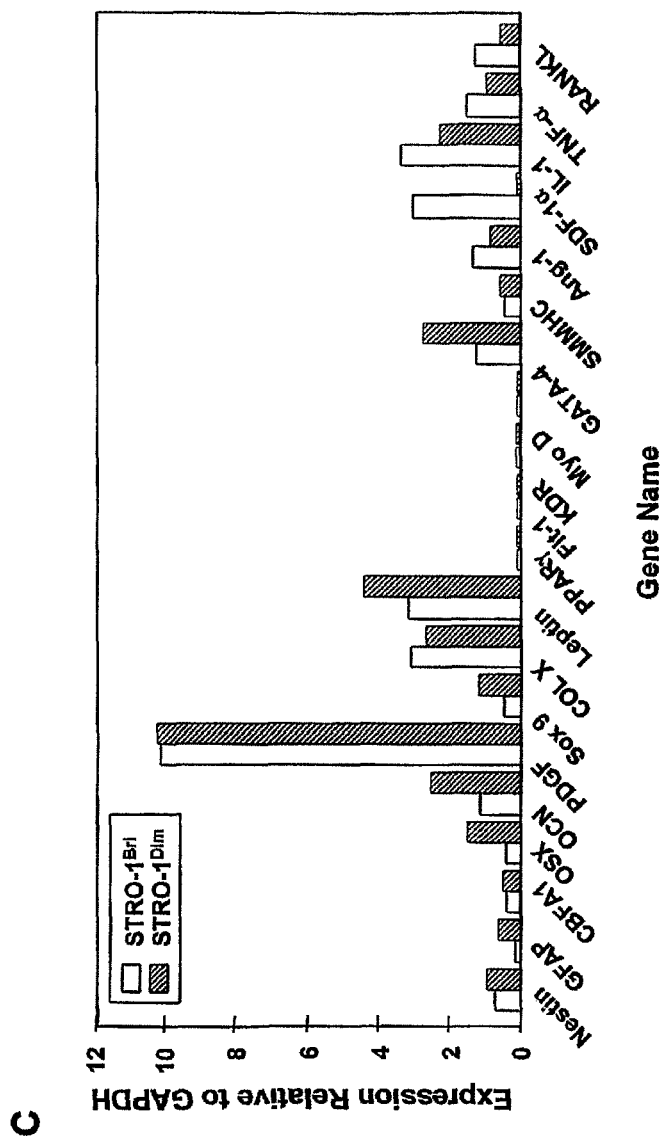

This was performed essentially as previously described (Gronthos et al. J Cell Sci. 116: 1827-1835, 2003; Gronthos and Simmons, Blood. 85: 929-940, 1995). In brief, approximately 1 to 3×10$^8$ adult human BMMNCs were incubated with blocking buffer (Hanks balanced salt solution [HBSS] supplemented with 1% human serum, 1% bovine serum albumin, and 5% fetal bovine serum), then sequentially incubated with STRO-1 supernatant, anti-IgM-biotin, streptavidin microbeads (Miltenyi Biotec, Auburn, Calif.), and finally streptavidin fluorescein isothiocyanate (FITC; Caltag Laboratories, Burlingame, Calif.) before being separated on a Mini magnetic-activated cell sorting (MACS) magnetic column (Miltenyi Biotec), according to the manufacturer's recommendations. The MACS-isolated STRO-1+ bone marrow mononuclear cells were subsequently sorted by using a FACStar flow cytometer (Becton Dickinson, Sunnyvale, Calif.), based on their high (STRO-1bright) or low (STRO-1dull) STRO-1 expression (FIG. 1A).

Isolation of STRO-1/Alkaline Phosphatase BMSSC Subpopulations.

Secondary cultures of human BMSSCs were prepared as single-cell suspensions by trypsin/EDTA (ethylenediaminetetraacetic acid) digest and then incubated with antibodies identifying STRO-1 and the bone-associated antigen alkaline phosphatase (AP), B4-78, as described by Gronthos et al., J Bone Miner Res. 14: 47-56, 1999. Approximately 2×10$^7$ cells were incubated with antibodies reactive to STRO-1 and alkaline phosphatase (B4-78) for 1 hour on ice. Replicate tubes were incubated with the corresponding single color and negative control antibodies. After Washing, the samples were incubated with goat anti-mouse IgG1-FITC and IgM-PE (phycoerythrin) antibodies (Southern Biotechnology Associates, Birmingham, Ala.) as secondary detection agents for 45 minutes on ice. Following washing, the cells were subsequently sorted to purity by double sorting, using a FACStar flow cytometer (Becton Dickinson), based on the 4 STRO-1/AP BMSSC subpopulations (Gronthos et al., J Bone Miner Res. 14: 47-56, 1999; Pan et al., Bone 34(1):112-23, 2004; and Atkins et al., J Bone Miner Res. 18(6):1088-98, 2003).

Calcium Flux Assays.

Single-cell suspensions of trypsin-detached secondary BMSSC cultures were resuspended to a concentration of 1×10$^6$ cells/mL in HBSS supplemented with 1% fetal calf serum (FCS) and 1.25 mM CaCl$_2$. The cells were incubated with 2 μM fura-2-AM (fura-2 acetoxymethyl ester; Molecular Probes, Eugene, Oreg.) for 30 minutes at 37° C. Excess fura-2-AM was removed by washing the cells twice, and the cells were resuspended in 2 mL HBSS containing 1% FCS and 1.25 mM CaCl$_2$ to a final concentration of 1×10$^6$ cells/mL. [Ca2+]$_i$ was measured using spectrofluorometer (LS55 Luminescence spectrometer, Perkin Elmer, Boston, Mass.), with alternating excitation of 340 and 380 nm and fluorescence emission at 510 nma. After establishing a base line level of [Ca2+]$_i$, the cells were treated with 30 ng/mL SDF-1a. When a stable peak of [Ca2+]$_i$ in response to SDF-1a was achieved, the BMSSCs were permeabilized with 0.1 mM digitonin, and ethylene glycol tetraacetic acid (EGTA) was added to a final concentration of 5 mM. The digitonin and EGTA measurements were used to calibrate [Ca2+]$_i$ with regard to fura 2-AM fluorescence in each sample using a calibration equation as previously described (Grynkiewicz et al., J Biol Chem. 260: 3440-3450, 1985)

Colony Efficiency Assays.

Colony-forming assays were performed using MACS/FACS-isolated STRO-1bright BMMNCs and then plated at a density of 5×10$^4$ per well in 24-well plates under serum-deprived conditions as previously described (Gronthos et al. J Cell Sci. 116: 1827-1835, 2003; Gronthos and Simmons, Blood. 85: 929-940, 1995). Cells were plated in the presence of different cytokine combinations. Growth factors used in this study included α-interferon 2a (30 000 IU/mL; F Hoffmann-La Roche, Basel, Switzerland), platelet-derived growth factor-BB (5 ng/mL), interleukin-4 (30 ng/mL), and stromal derived factor-1 (30 ng/mL; CytoLab/PeproTech, Rehovot, Israel). The cultures were terminated at day 14, and the number of CFU-Fs enumerated following staining with 0.1% (wt/vol) toluidine blue in 1% paraformaldehyde. Aggregates of greater than 50 cells were scored as CFU-F-derived colonies.

Flow Cytometric Analysis.

BMSSC cultures were prepared by trypsin/EDTA digest, then resuspended in blocking buffer for 30 minutes. Single-cell suspensions were then incubated with either anti-CXCR4 antibody or 1A6.11 at a concentration of 10 μg/mL for 1 hour on ice. Similarly, high SDF-1-expressing BMSSC and vector control cell lines were prepared by trypsin/EDTA treatment, blocked, then incubated with either anti-annexin V antibody or the isotype-matched control antibody, 1D4.5. After washing, the cells were incubated with the secondary detection reagents, goat anti-mouse IgG1- or IgG2b-FITC-conjugated antibodies (1/50; Southern Biotechnology Associates) for 45 minutes on ice. Following washing, the samples were analyzed using an Epics-XL-MCL flow cytometer (Beckman Coulter, Hialeah, Fla.).

RT-PCR Analysis

Total RNA was prepared from 2×10$^4$ STRO-1$^{bright}$-, STRO-1$^{dull}$-, and STRO-1$^{negative}$-sorted bone marrow mononuclear cells; cultured BMSSC STRO-1/alkaline phosphatase-sorted subpopulations; or the human osteosarcoma cell line, MG63, using the cRNA STAT-60 system (TEL-TEST, Friendswood, Tex.). Total RNA isolated from each subpopulation was then used as a template for cDNA synthesis, prepared using a first-strand cDNA synthesis kit (Pharmacia Biotech, Uppsala. Sweden). The expression of various transcripts was assessed by PCR amplification, using a standard protocol as previously described. 5 Primer sets used in this study were as follows: SDF-1 (forward, 5'-gacccgcgctcgtccgcc-3' (SEQ ID NO: 4); reverse, 5'-gctggactcctactgtaaggg-3' (SEQ ID NO: 5)); CXCR4 (forward, 5'-tctggagaaccagcgttac-3' (SEQ ID NO: 6); reverse, 5'-gacgccaacaragaccacct-3' (SEQ ID NO: 7)); GAPDH {forward, 5'-catggagaaggctggggctc-3' (SEQ ID NO: 8); reverse, 5'-cactgacacgttggcagtgg-3' (SEQ ID NO: 9)}. Amplified products were analyzed by 1.5% agarose gel electrophoresis and visualized by ethidium bromide staining. Semiquantitative analysis of transcript abundance was assessed relative to GAPDH expression using ImageQant software (Molecular Dynamics, JO Sunnyvale, Calif.).

Generation of Transduced BMSSC Lines.

Retroviral expression constructs were generated with the retroviral vector pLNCX2 (Clontech Laboratories, Palo Alto, Calif.) encoding the full-length human SDF-1 cDNA amplified using the PCR forward (5'-aataactcgagac-ccgcgctcgtccgcc-3' (SEQ ID NO: 10)) and reverse (5'-aattaacggccgctggactcctactgtaaggg-3' SEQ ID No: 11)) primer set (underlined), constructed with XhoI and NotI (bold) restriction sites, respectively. The packaging cell line PT67 was transfected with either the SDF-1-containing constructs or pLNCX2 vector alone using Fugene-6-reagent (Boehringer Mannheim, Mannheim, Germany), then selected with 800 μg/mL G418 (Sigma, Castle Hill, NSW, Australia). Harvested supernatant containing infectious particles from stable l'T67 lines was used to transduce cultured BMSSCs in the presence of 5 μg/mL polybrene (Sigma). Stable multicolony-derived BMSSCs expressing high levels of SDF-1α and control cell lines were established following selection with 800 μg/mL 0418. Secreted SDF-1α concentrations were measured from supernatant filtered through a 0.2-μm tilter using a standard SDF-1 enzyme-linked immunosorbent assay (ELISA) kit according to the manufacturer's specifications (R&D Systems, Minneapolis, Minn.).

Construction of a BMSSC cDNA Subtraction Hybridization Library.

In preliminary studies, STRO-1dull-expressing marrow cells (glycophorin-A+ nucleated red cells) and STRO-1bright-expressing cells (CFU-F population) were isolated by the MACS/FACS procedure as described in "Purification of BMSSCs." Total RNA was prepared from STRO-1bright and STRO-1dull cells pooled from 5 different marrow samples (2 men and 3 women, aged 19-32 years) using the RNA STAT-60 system (TEL-TEST). First-strand synthesize was performed using the SMART cDNA synthesis kit (Clontech Laboratories). The resultant mRNA/single-stranded cDNA hybrid was amplified by long-distance PCR (Advantage 2 PCR kit; Clontech) using specific primer sites at the 3' and 5' prime ends formed during the initial RT process according to the manufacturer's specifications. Following RsaI digestion of the STRO-1bright cDNA, 2 aliquots were used to ligate different specific adaptor oligonucleotides using the Clontech PCR-Select cDNA Subtraction Kit. Two rounds of subtractive hybridization were performed using STRO-1bright (tester) and STRO-1 dull (driver) cDNA, and vice versa, according to the manufacturer's protocol. This procedure was also performed in reverse using STRO-1dull tester cDNA hybridized against STRO-1bright driver cDNA.

Differential Screening of BMSSC Subtraction Library.

To identify genes uniquely expressed by STRO-1bright BMSSC population, STRO-1bright-subtracted cDNA was ligated into a T/A cloning vector (AdvaTAge PCR cloning kit; Clontech) then transformed into DH5α *Escherichia coli*. Two hundred randomly selected, ampicillin-resistant bacterial clones were amplified by PCR using the Clontech PCR-Select Differential Screening Kit according to the manufacturer's specifications. Briefly, the cDNA was used to construct replicate low-density microarray filters (zeta-probe GT membranes; BioRad, Hercules, Calif.) using a BRL Hybri-dot 96-well format manifold vacuum system as recommended by the manufacturer. Subtracted STRO-1bright and subtracted STRO-1dull cDNA were denatured at 95° C. then labeled with 50 μCi (1.85 MBq) α-[32P] dCTP (3000 Ci [1.85 MBq]/mmol; ICN Radiochemicals, Irvine, Calif.) using Klenow enzyme (exo-; 5 U) for 40 minutes at 37° C. The DNA probes were hybridized to replicate filters overnight at 72° C., using Clontech Express Hyb. The filters were washed 4 times with 2× standard saline citrate (SSC)/0.5% sodium dodecyl sulfate (SDS) and 2 times with 0.2×SSC/0.5% SDS at 68° C., then screened using a PhosphoImager and analyzed using ImageQuant software (Molecular Dynamics).

Differentiation of CFU-F In Vitro.

We have previously reported the conditions for the induction of human BM stromal cells to develop a mineralized bone matrix in vitro cultured in α-MEM supplemented with 10% FCS, 100 μM L-ascorbate-2-phosphate, dexamethasone 10-7 M, and 3 mM inorganic phosphate (Gronthos at al., Blood. 84: 4164-4173, 1994).

Ectopic Bone Formation Assay.

The adherent cells derived from STRO-1bright-sorted bone marrow mononuclear cells at passage 2 to 3 were trypsinized, mixed with 40 mg hydroxyapatite/tricalcium phosphate ceramic particles (Zimmer, Warsaw, Ind.) and then implanted into subcutaneous pockets on the dorsal surface of 8-week-old nonobese diabetic/severe combined immunodeficient (NOD/SCID) mice as described previously (Gronthos et al. J Cell Sci. 116: 1827-1835, 2003). These procedures were performed in accordance to specifications of an approved animal protocol (The University Adelaide AEC no. M29/2002). Implants were recovered after 8 weeks, fixed in 4% paraformaldehyde for 2 days, and then decalcified for a further 10 days in 10% EDTA prior to embedding in paraffin. Each transplant was cut into 2 pieces, then placed cut-surface down for paraffin embedding. For histologic analysis, 5-μm sections of the implants were prepared and stained with hematoxylin and eosin (H&E) representative of the middle and either end of each transplant approximately 3 to 4 mm in length. The amount of new bone formation was calculated as a percentage of the total surface area present in 12 tissue sections. Measurement of new bone formation was assessed using Scion Imaging Software (Frederick, Md.) as previously described (Shi et al. Nat Biotechnol. 20: 587-591, 2002).

Statistics.

The Student t test was used for pairwise comparisons as indicated. Statistical significance was given at P less than 0.05. One-way analysis of variance (ANOVA) was used for multiple comparisons as indicated. Statistical significance between the groups was determined using the Fisher projected least significance difference test at P less than 0.05.

Figure 2:
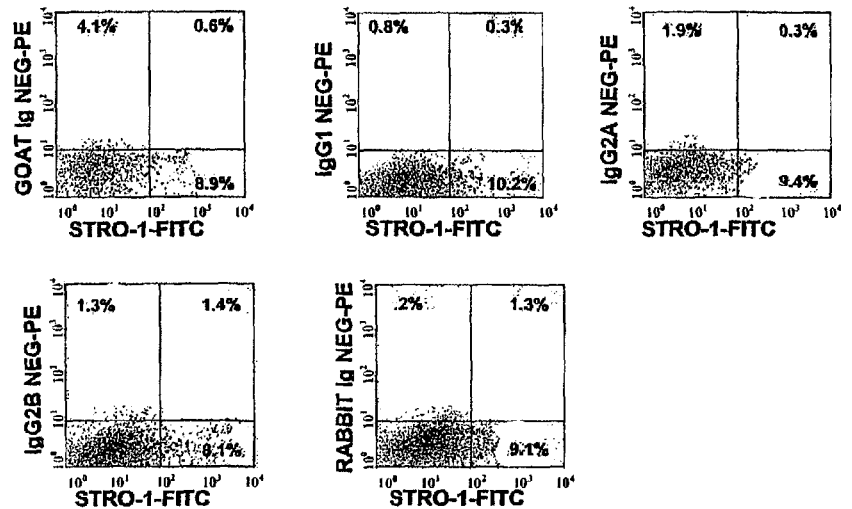
FIG. 2. Immunophenotypic expression pattern of ex vivo expanded cells derived from bone marrow MPCs. Single cell suspensions of ex viva expanded cells derived bone marrow MPC were prepared by trypsin/EDTA detachment and subsequently incubated with the STRO-1 antibody in combination with antibodies identifying a wide range of cell lineage-associated markers. STRO-1 was identified using a goat anti-murine IgM-fluorescein isothiocyanate while all other markers were identified using either a goat anti-mouse or anti-rabbit IgG-phycoerythrin. For those antibodies identifying intracellular antigens, cell preparations were first labelled with the STRO-1 antibody, fixed with cold 70% ethanol to permeabilize the cellular membrane and then incubated with intracellular antigen-specific antibodies. Isotype matched control antibodies were used under identical conditions. Dual-colour flow cytometric analysis was performed using a COULTER EPICS flow cytometer and list mode data collected. The dot plots represent 5,000 listmode events indicating the level of fluorescence intensity for each lineage cell marker (y-axis) and STRO-1 (x-axis). The vertical and horizontal quadrants were established with reference to the isotype matched negative control antibodies.
Figure 2:
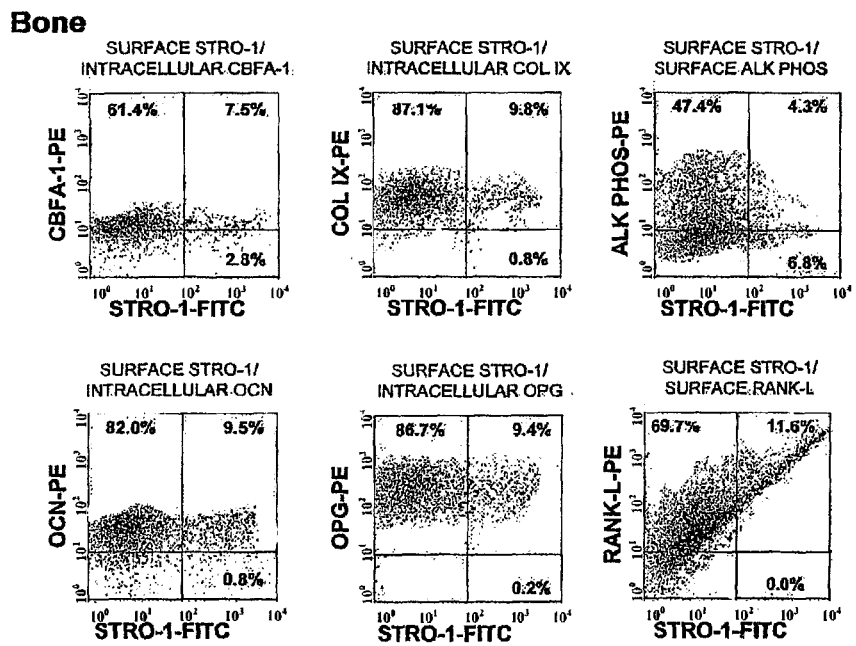
Figure 2:
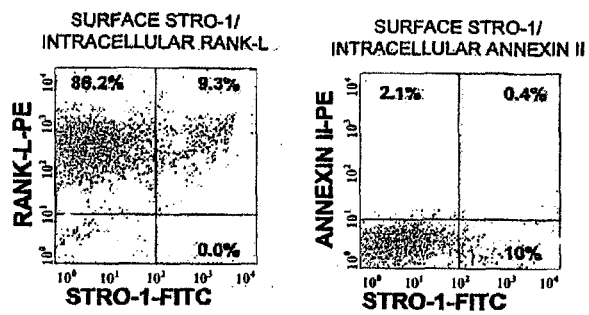
Figure 2:
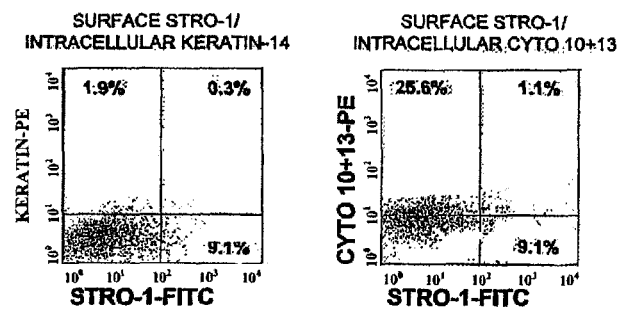
Figure 2:
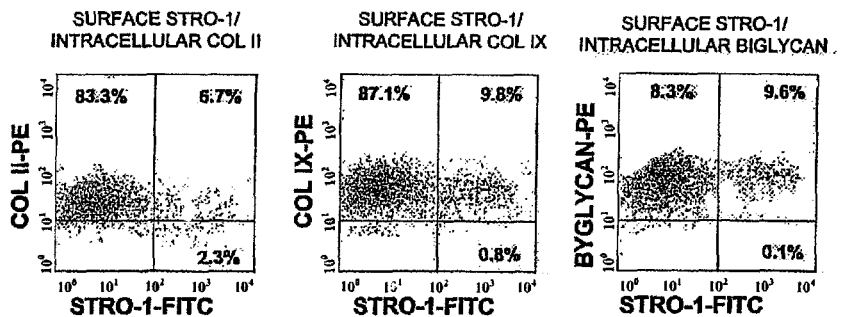
Figure 2:
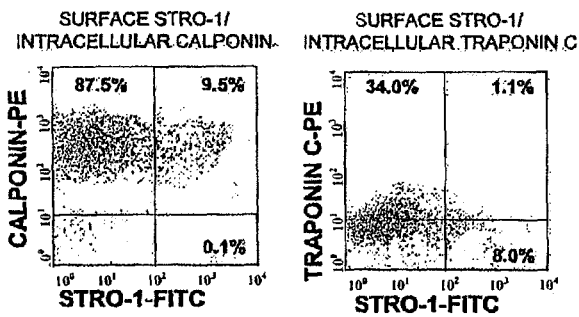
Figure 2:
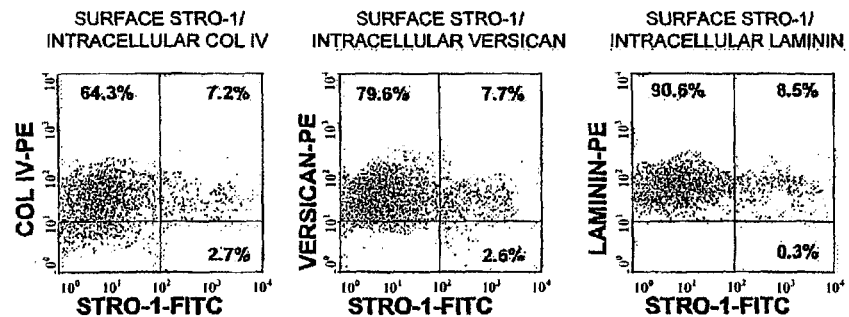
Figure 2:
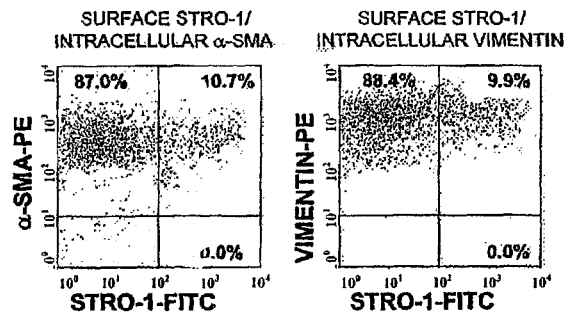
Figure 2:
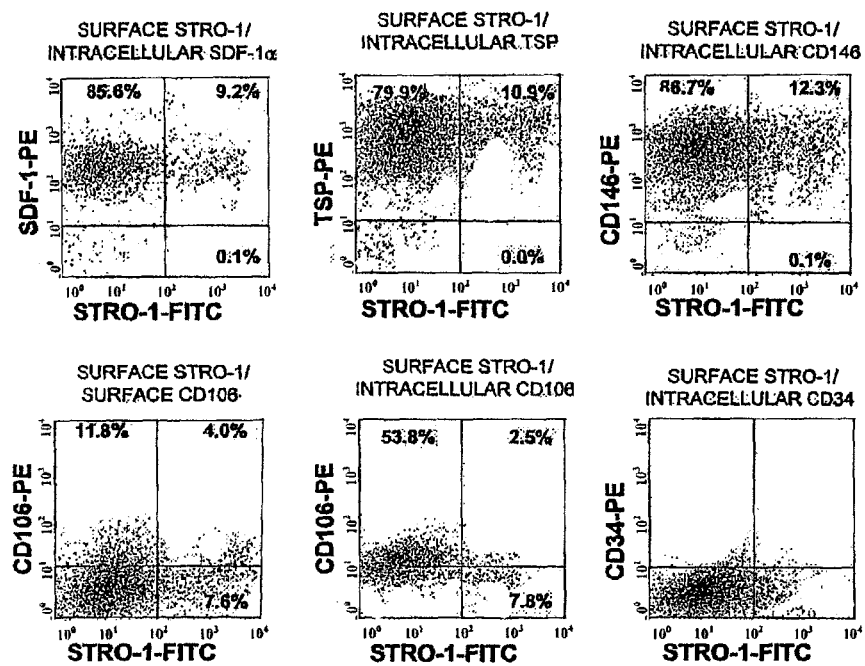
Figure 2:
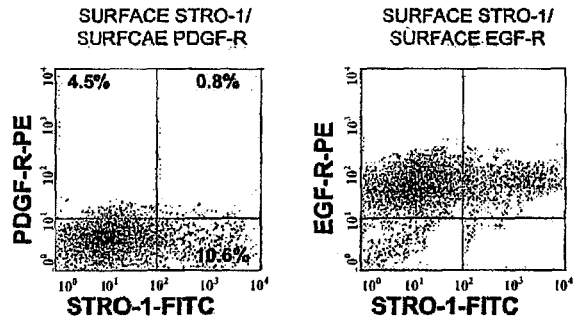
Figure 2:
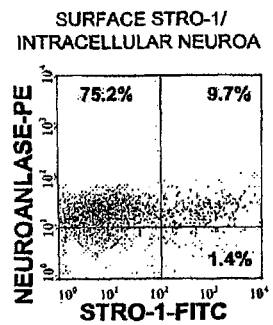
Figure 2:
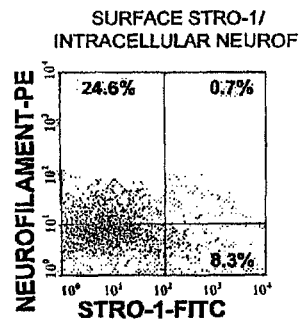
Figure 2:
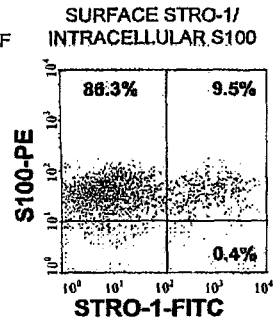

Example 1: Stro-1$^{dim}$ Cultured Cells are More Committed while Stro-1$^{bri}$ Cells are Less Committed Precursor Cells We have previously reported that multipotential mesenchymal precursor cells (MPC) can be purified from adult human bone marrow mononuclear cells based on the phenotype STRO-1$^{bri}$/VCAM-1 (CD106)$^+$ or STRO-1$^{bri}$/MUC-18 (CD146)$^+$ (Gronthos et al. J. Cell Sci 116:1827-1835, 2003; Shi and Gronthos JBMR 18(4): 696-704, 2003; PCTAU2004/000416). The MPC population can be readily expanded in vitro under defined culture conditions (Gronthos et al. J. Cell Sci 116:1827-1835, 2003). We now present data characterising the ex vivo expanded MPC progeny based on markers associated with different cell lineages, at both the mRNA and protein level, using reverse transcription-polymerase chain reaction (RT-PCR) and flow cytometric analysis, respectively. Whilst, all freshly isolated bone marrow MPC express STRO-1 at high levels (Stro-1$^{bri}$), the majority of cells down regulate STRO-1 expression (Stro-1$^{dim}$) following ex vivo expansion (Gronthos et al. J. Cell Sci 116:1827-1835, 2003). In the first series of experiments, semi-quantitative RT-PCR analysis was employed to examine the gene expression profile of various lineage-associated genes expressed by STRO-1$^{dim}$ or STRO-1$^{bri}$ populations, isolated by fluorescence activated cell sorting (FIG. 1A). Relative gene expression for each cell marker was assessed with reference to the expression of the house-keeping gene, GAPDH, using ImageQant software (FIG. 1B, C). In addition, dual-colour flow cytometric analysis was used to examine the protein expression profile of ex vivo expanded MPC based on their expression of a wider range of cell lineage-associated markers in combination with the STRO-1 antibody (FIG. 2). A summary of the general phenotype based on the gene and protein expression of STRO-1$^{dim}$ and STRO-1$^{bri}$ cultured cells is presented in Table 3. The data indicate that ex viva expanded STRO-1$^{bri}$ MPC exhibit differentially higher expression of markers associated with perivascular cells, including angiopoietin-1, VCAM-1, SDF-1, IL-1$_\beta$, TNFα, and RANKL. Conversely, STRO-1$^{dim}$ ex vive expanded cells expressed higher levels of nestin, GFAP, osterix, osteocalcin, SOX9, GATA-4, leptin, and smooth muscle myosin heavy chain. It therefore appears that ex viva expanded STRO-1$^{bri}$ MPC exhibit a more immature and perivascular-like phenotype in comparison to STRO-1$^{dim}$ cells which exhibit a phenotype characteristic of more committed precursor cell types including chondroblasts, osteoblasts, adipoblasts, epithelial cells, neural progenitors and cardiomyoblasts. Comparisons between the protein and gene expression profiles of STRO-1$^{dim}$ and STRO-1$^{bri}$ cultured cells are summarises in Tables 3 and 4.

Figure 3:
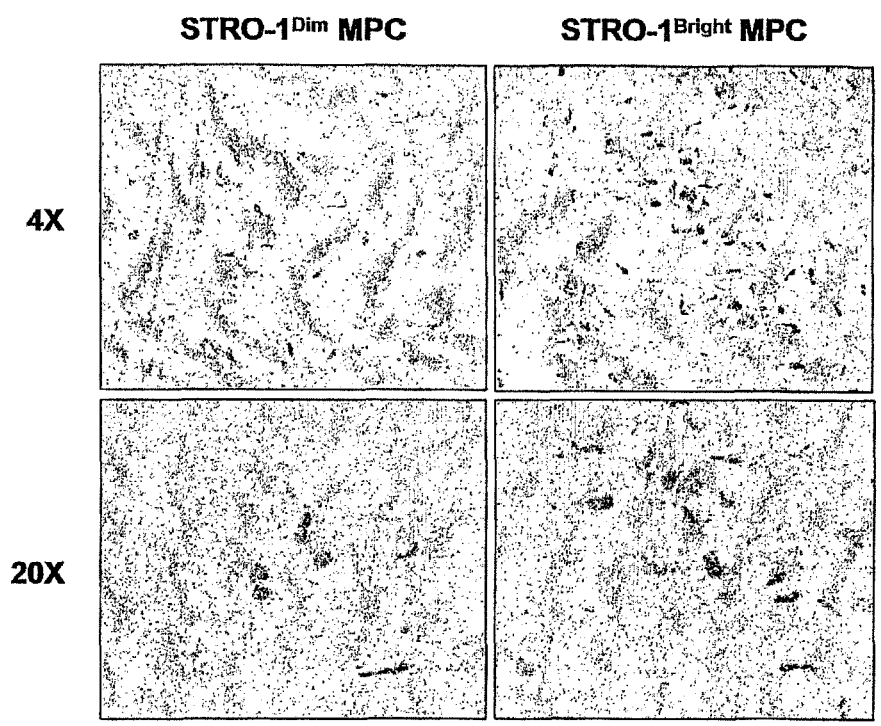
FIG. 3. Adipogenic Development In Vitro. Single cell suspensions were generated by trypsin/EDTA digest from secondary cultures of ex vive expanded cells, derived from STRO-1$^{bri}$/VCAM-1$^+$ sorted bone marrow cells. The expanded cells were then isolated according to their expression of STRO-1 using single colour fluorescence activated cell sorting as shown in FIG. 1A. STRO-1$^{bri}$ and STRO-1$^{dim}$ sorted MPC derived cells were then plated overnight, into 6-well plates, at a density of 1×10$^5$ cells per well under regular growth medium. On the following day the culture medium was replaced with adipogenic inductive medium as described in the methods. The cultures were fed twice a week thereafter for a total period of three weeks at which time the cells were fixed and stained for Oil red O. Low (4×) and high (20×) power magnifications are shown depicting Oil red O staining of lipid containing adipocytes scattered throughout the adherent stromal layers. On average 22±5 Oil red O positive adipocytes were identified in the STRO-1$^{bri}$ cultures (per unit area at 20×, n=9 fields) when compared to 7±2 adipocytes (per unit area at 20×, n=9 fields) in the STRO-1$^{dim}$ cultures.
Figure 4:
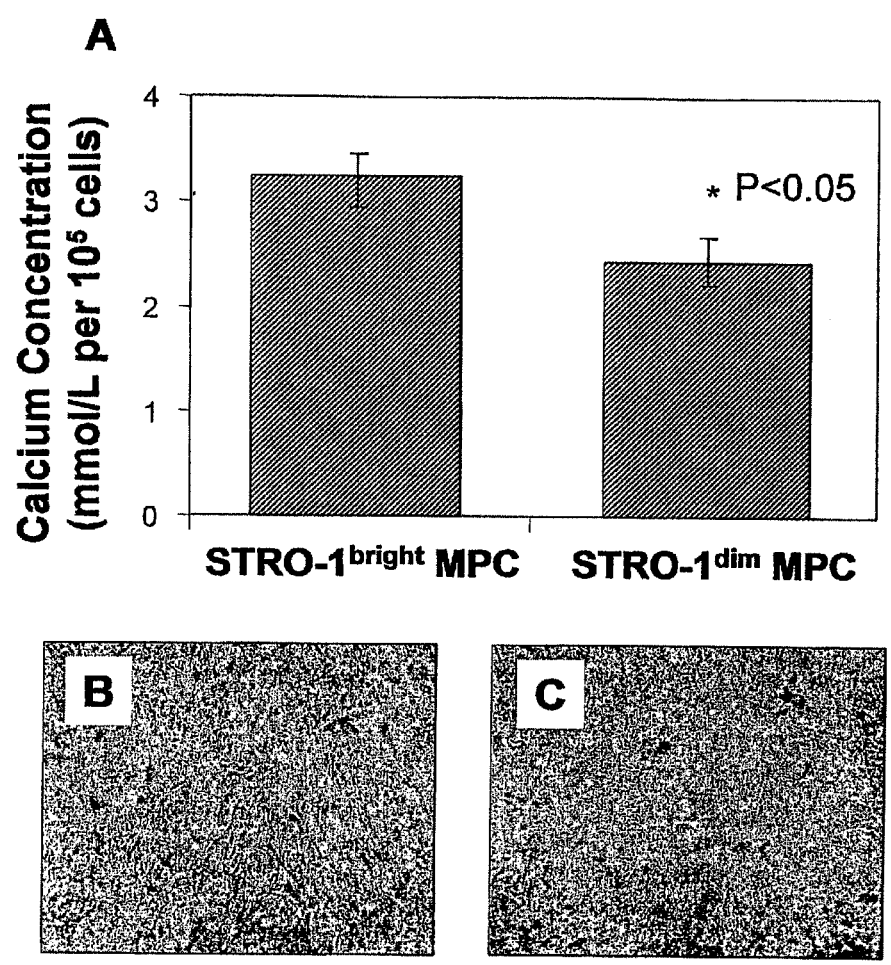
FIG. 4. Osteogenic Development In Vitro. Single cell suspensions were generated by trypsin/EDTA digest from secondary cultures of ex vivo expanded cells, derived from STRO-1$^{bri}$/VCAM-1$^+$ sorted bone marrow cells. The expanded cells were then isolated according to their expression of STRO-1 using single colour fluorescence activated cell sorting (FACS) as shown in FIG. 1A. STRO-1$^{bri}$ and STRO-1$^{dim}$ FACS isolated cells were then plated overnight, into 48-well plates, at a density of 0.3×10$^5$ cells per well under regular growth medium (four replicates per condition). On the following day the culture medium was replaced with osteogenic inductive medium as described in the methods. The cultures were fed twice a week thereafter for a total period of three weeks at which time the cells were washed then treated with 0.6N HCl to extract the calcium within the mineralized deposits. Samples were reacted with o-cresolphthalein-complexon and the colorimetric reaction was read at 570 nm. The absolute calcium concentration was determined according to a standard curve for calcium. (A) Calcium measurements showed that the STRO-1$^{bri}$ cultures synthesised significantly (*; p<0.05; t-test) more mineral when compared to the STRO-1$^{dim}$ cultures. Replicate cultures were fixed and stained for Alizarin red staining depicting typical levels of mineralised deposits in the adherent layers of STRO-1$^{bri}$ (B) and STRO-1$^{dim}$ (C) cultures.
Figure 5:
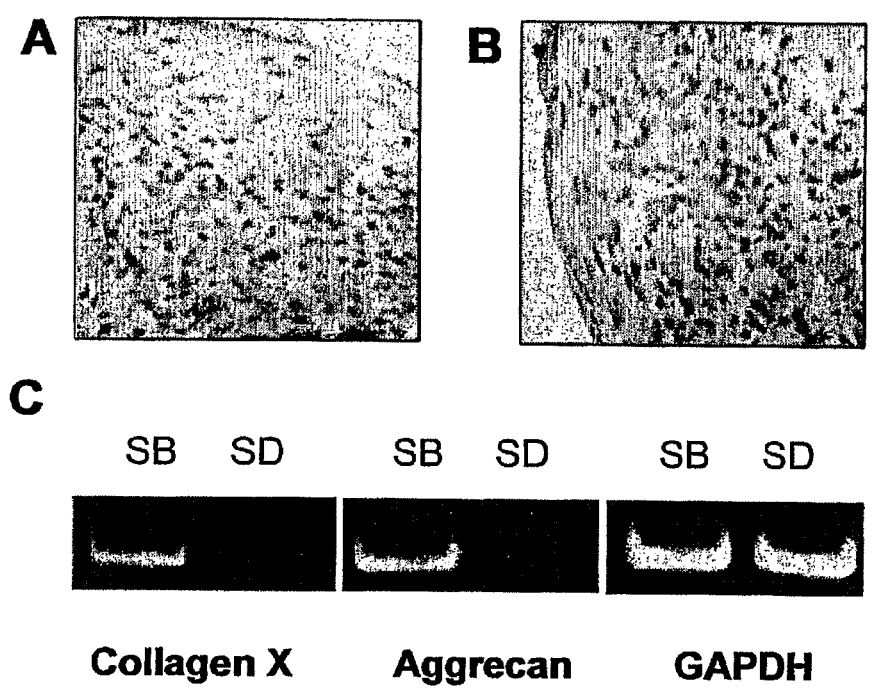
FIG. 5. Chondrogenic Development In Vitro. Single cell suspensions were generated by trypsin/EDTA digest from secondary cultures of ex vivo expanded cells, derived from STRO-1$^{bri}$/VCAM-1$^+$ sorted bone marrow cells. The expanded cells were then isolated according to their expression of STRO-1 using single colour fluorescence activated cell sorting (FACS) as shown in FIG. 1A. STRO-1$^{bri}$ and STRO-1$^{dim}$ FACS isolated cells were then pelleted into polypropylene tubes at a density of 2.5×10$^5$ cells per tube and cultured in chondrogenic inductive media. The cultures were fed twice a week thereafter for a total period of three weeks. Cell pellets were retrieved and used for histological examination or preparation for total RNA as described in the methods. Both STRO-1$^{bri}$ (A) and STRO-1$^{dim}$ (B) cell populations were capable of forming cell pellets containing chondrocyte-like cells. RT-PCR analysis indicated that the STRO-1$^{bri}$ (SB) population demonstrated higher levels of the cartilage associated genes collagen type X and aggrecan when compared to the STRO-1$^{dim}$ (SD) cell population (C).

Example 2: Differential Capacity of STRO-1$^{dim}$ and STRO-1$^{bri}$ Cultured Cells to Differentiate In Vitro We next examined whether the observed differences in the gene and protein expression profiles of STRO-1$^{dim}$ and STRO-1$^{bri}$ cultured cells was reflective of any functional differences in their capacity to differentiate into multiple cell lineages. Cultures of ex vivo expanded STRO-1$^{bri}$/CD146$^+$ derived cells were isolated by FACS based on their expression of STRO-1 antigen as described above. FACS isolated STRO-1$^{dim}$ and STRO-1$^{bri}$ cultured cells were subsequently plated under inductive conditions for fat (FIG. 3), bone (FIG. 4) and cartilage (FIG. 5) formation. In all cases STRO-1$^{bri}$ cultured cells showed a higher capacity to form fat, bone and cartilage under the specified conditions when compared with STRO-1$^{dim}$ cultured cells. The data from these experiments, substantiate the gene and protein expression results obtained above, demonstrating that STRO-1$^{bri}$ cultured cells are a primitive population containing a high proportion of less committed precursor cells that can be influenced to differentiate towards any specified cell lineage under the appropriate culture conditions (FIGS. 3, 4, 5) and may be referred to as MPC. Conversely, the STRO-1$^{dim}$ cultured cells contain a high proportion of committed cells representative of various lineages and may be referred to as TSCC. It is proposed that the Stro-1$^{dim}$ population is heterogenous comprising cells separately committed to range of different tissue types.

Figure 6:
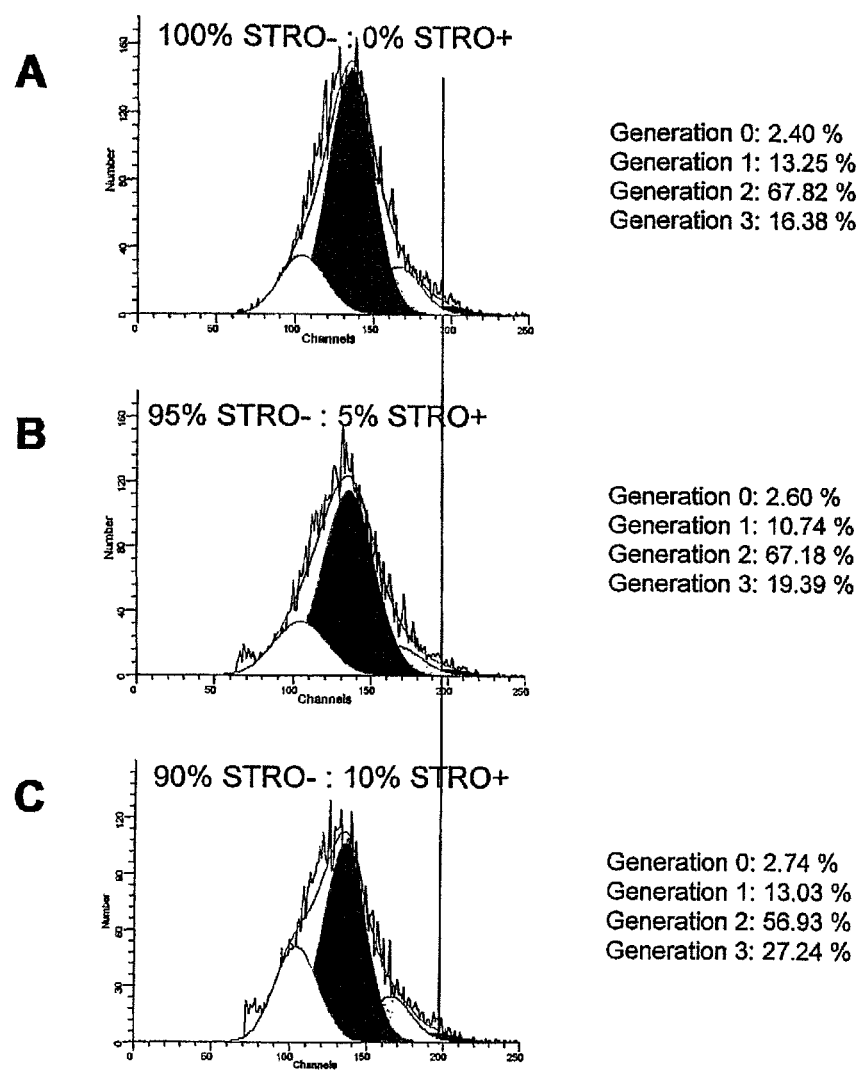
FIG. 6. STRO-1$^{Bri}$ cells induce the proliferation of STRO-1$^{dim}$ cells. Single cell suspensions of ex vive expanded bone marrow MPC were prepared by trypsin/EDTA treatment. Cells were stained with the STRO-1 antibody and sorted into populations of STRO-1$^{dim}$ or STRO-1$^{bri}$ expressing cultured cell populations as described in FIG. 1. Cells were labelled with CFSE as described in the methods. Unlabelled cells were used to establish a negative control (auto-fluorescence) . Colcemid® (100 ng/ml) was used to inhibit cell division and provided an input labelling index (Generation 0). Unlabelled STRO-1$^{bri}$ were subsequently added back to the CFSE-labelled STRO-1$^{dim}$ cells at a ratio of (A) 0 STRO-1$^{bri}$ cells: 1×10$^5$ STRO-1$^{dim}$ cells (0%); (B) 0.05×10$^5$ STRO-1$^{bri}$ cells: 0.95×10$^5$ STRO-1$^{dim}$ cells (5%); (C) 0.1×10$^5$ STRO-1$^{bri}$ cells: 0.9×10$^5$ STRO-1$^{dim}$ cells (10%); (D) 0.2× 10$^5$ STRO-1$^{bri}$ cells: 0.8×10$^5$ STRO-1$^{dim}$ cells (20%); (E) 0.5×10$^5$ STRO-1$^{bri}$ cells: 0.5×10$^5$ STRO-1$^{dim}$ cells (50%). The add-mixtures were cultured for a period of 7 days, harvested, and analysed by flow cytometry as described in the methods. Cell proliferation was analysed using the ModFit LT for win 32 (Version 2.0). The STRO-1$^{bri}$ cells (R1) were found to stimulate the proliferation of STRO-1$^{dim}$ cells in a dose-dependent manner.
Figure 6:
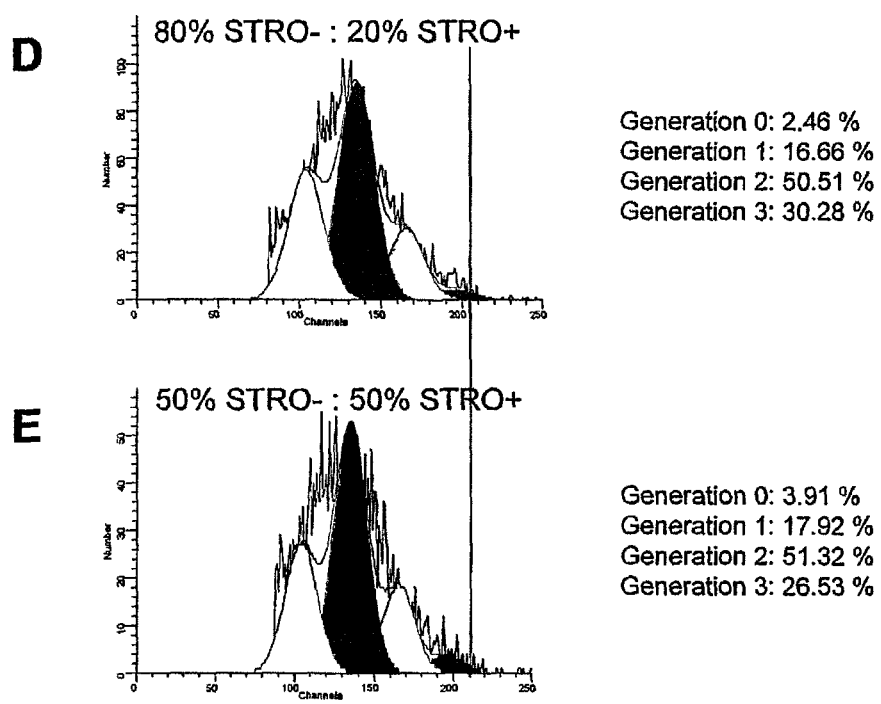

Example 3: STRO-1$^{bri}$ Cells can Modify the Growth Potential of Tissue Specific Committed Cells In Vitro and In Vive The identification of the two different ex vivo expanded MPC derived cell populations representative of different developmental stages has significant implications in the use of whole cultured preparations derived from Stro-1$^{bri}$ cells for clinical therapies. Initial studies were design to examine the influence of primitive, less committed STRO-1$^{bri}$ cultured MPC on the growth of more mature and committed STRO-1$^{dim}$ cultured TSCC. Experiments were designed to add increasing percentages of FACS isolated STRO-1$^{bri}$ cultured MPC with FACS isolated STRO-1$^{dim}$ cultured TSCC, previously labelled with a fluorescent tag, CFSE. FIG. 6 shows that the proliferation of labelled STRO-1$^{dim}$ cells is effected by the presence of unlabelled STRO-1$^{bri}$ cells. When a CFSE labelled cell divides the two daughter cells contain half the fluorescence of the parental cell. Therefore, different generations of daughter cells are represented as fluorescent distributions with proportionate ever decreasing fluorescence intensity, where the curve on the far right of the histogram (intersected by vertical line) represents the point of the initial STRO-1$^{dim}$ population (FIG. 6). The data demonstrated that a higher proportion of STRO-1$^{dim}$ cells were stimulated to increase their proliferation rates, where more cells were shown to be undergoing at least 3 to 4 divisions, following the addition of greater than 5% STRO-1$^{bri}$ cells. Therefore, it follows that in order to get a sustainable and efficient ex vivo expansion of unfractionated MPC derived cells the cultures require the presence of greater than 5% of STRO-1$^{bri}$ cells within the population.

Figure 7:
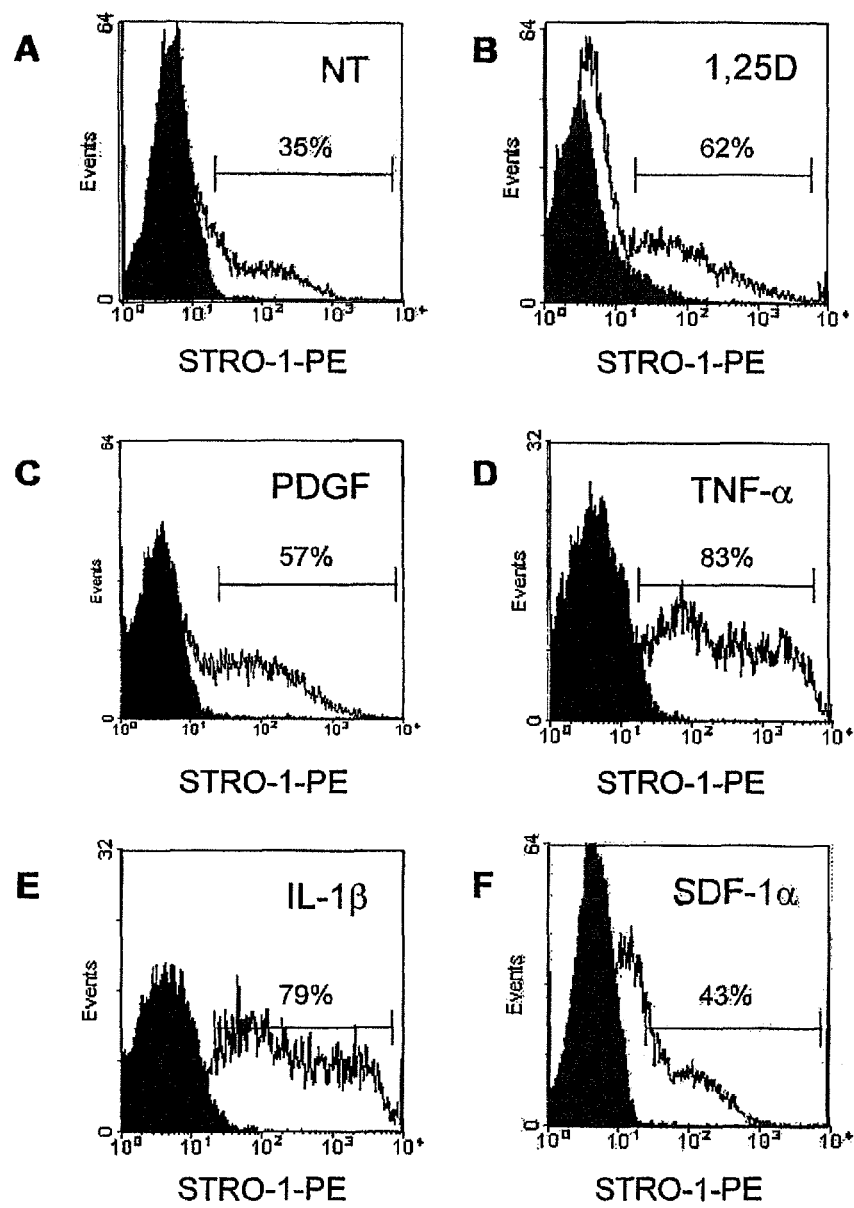
FIG. 7. Cytokines and osteotropic agents increase the number of STRO-1$^{bri}$ cells in culture. Established cultures of MPC were cultured in basal medium supplemented with 10% FCS (A), or a range of factors, including 1×10$^{-8}$M 1α,25-dihydroxyvitamin D$_3$ (1,25D) (B), 10 ng/ml Platelet derived growth factor (PDGF) (C), 10 ng/ml Tumour necrosis factor-alpha (TNF-α) (D); 10 ng/ml interleukin-1β (IL-1β) (E) and 30 ng/ml stromal derived factor 1-alpha (SDF-1α) (F), for 5 days, stained with STRO-1 mAb and analysed as described above. These factors were found to increase the number of STRO-1$^{bri}$ MPC. The results displayed are a representative example of 3 independent experiments.

Further investigations were performed to determine whether more primitive, less committed STRO-1$^{bri}$ cultured MPC could also influence the proliferation capacity of TSCC in vivo. Two in vivo models were used to address this question. The first model employed athymic nude rats that had undergone ligation of the left anterior descending (LAD) coronary artery and injected 48 hours later with saline, FACS isolated cultured human STRO-1$^{dim}$ and STRO-1$^{bri}$ cells and fresh aspirates of STRO-1 depleted bone marrow mononuclear cells (FIG. 7). After two weeks animals were sacrificed, and cardiac tissues were fixed and concomitantly stained with two monoclonal antibodies: the first being selectively reactive with the rat, but not the human, Ki67 antigen, and the second being reactive with the cardiomyocyte marker troponin I. Dually stained cells, indicative of proliferating rat cardiomyocytes, were detected by immunoperoxidase technique. Animals receiving STRO-1$^{bri}$ human cells demonstrated 2.5-5 fold higher numbers of proliferating rat cardiomyocytes compared with control animals receiving saline or STRO-1$^{dim}$ human cells (FIG. 7).

Figure 8:
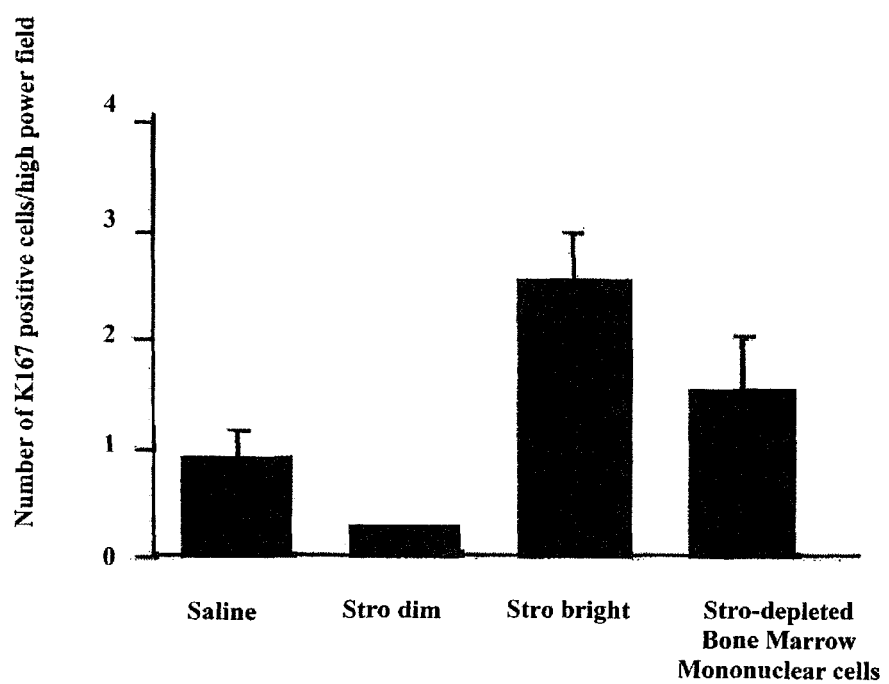
FIG. 8. Athymic nude rats underwent ligation of the left anterior descending (LAD) coronary artery and injected 48 hours later with saline, 1×10$^6$ human Stro-1$^{dim}$ cells, 1×10$^6$ human Stro-1$^{bri}$ cells or 1×10$^6$ human Stro-1-depleted bone marrow mononuclear cells. Two weeks later, animals were sacrificed, and cardiac tissues were fixed and concomitantly stained with two monoclonal antibodies: the first being selectively reactive with the rat, but not the human, Ki67 antigen, and the second being reactive with the cardiomyocyte marker troponin I. Dually stained cells, indicative of proliferating rat cardiomyocytes, were detected by immunoperoxidase technique. Animals receiving 1×10$^6$ Stro-1$^{bri}$ human cells demonstrated 2.5-5 fold higher numbers of proliferating rat cardiomyocytes compared with control animals receiving saline or 1×10$^6$ Stro-1$^{dim}$ human cells (p<0.05).

The second model utilized athymic nude rats injected subcutaneously with rat glioblastoma tumor cells, which constitutively secrete VEGF. Two weeks later, the rats received intratumor injections with either saline, FACS isolated human STRO-1$^{dim}$ or STRO-1$^{bri}$ human cells (FIG. 8). One week later, animals were sacrificed, and tumor tissues were fixed and concomitantly stained with two monoclonal antibodies: the first being reactive with the alpha-smooth muscle actin antigen expressed by smooth muscle cells, and the second being reactive with the vWF antigen expressed by vascular endothelial cells. Dually stained structures, indicative of arterioles and arteries containing both endothelium and smooth muscle, were detected by immunoperoxidase technique. Animals receiving STRO-1$^{bri}$ human cells demonstrated 3.5-8 fold higher numbers of arterioles and arteries at the site of cellular injection in the tumors compared with control animals receiving saline or STRO-1$^{dim}$ human cells (FIG. 8). No differences were seen at sites distal to where the human cells had been injected.

Figure 9:
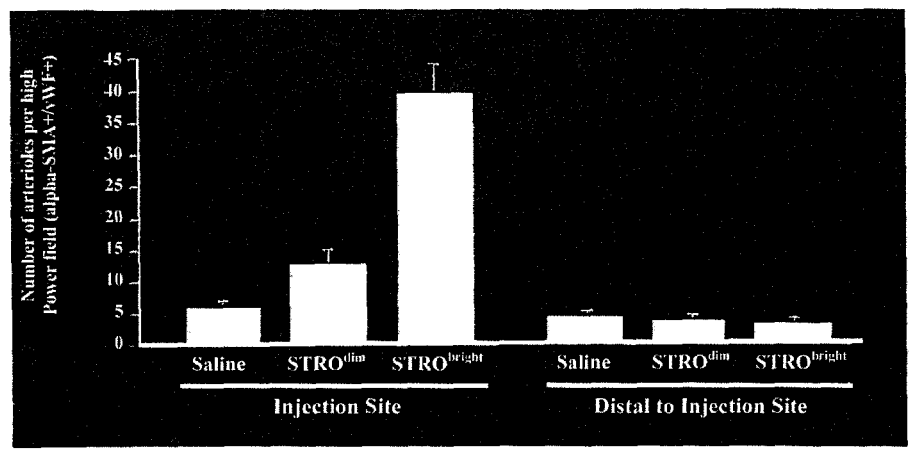
FIG. 9. Athymic nude rats were injected subcutaneously with rat glioblastoma tumor cells, which constitutively secrete VEGF. Two weeks later, the rats received intra-tumor injections with saline, 0.5×0$^6$ human Stro-1$^{dim}$ cells or 0.5× 10$^6$ human Stro-1$^{bri}$ cells. One week later, animals were sacrificed, and tumor tissues were fixed and concomitantly stained with two monoclonal antibodies: the first being reactive with the alpha-smooth muscle actin antigen expressed by smooth muscle cells, and the second being reactive with the vWF antigen expressed by vascular endothelial cells. Dually stained structures, indicative of arterioles and arteries containing both endothelium and smooth muscle, were detected by immunoperoxidase technique. Animals receiving 0.5×10$^6$ Stro-1$^{bri}$ human cells demonstrated 3.5-8 fold higher numbers of arterioles and arteries at the site of cellular injection in the tumors compared with control animals receiving saline or 1×10$^6$ Stro-1$^{dim}$ human cells (p<0.05). No differences were seen at sites distal to where the human cells had been injected.

Example 4: Increase in the Number of STRO-1$^{bri}$ MPC in Cell Cultures Derived from STRO-1 Positive Cells After demonstrating the capacity of STRO-1$^{bri}$ cultured MPC to increase the proliferation of more TSCC we next examined the effect of a range of growth factors to increase the proportion of ex vivo expanded STRO-1$^{bri}$ MPC (FIG. 9). Established cultures derived from STRO-1$^{bri}$/CD146$^+$ isolated bone marrow cells were grown in basal medium supplemented with 10% FCS (A) or a range of factors, including 1×10$^{-3}$M 1α,25-dihydroxyvitamin D$_3$ (1,25D) (B) 10 ng/ml Platelet derived growth factor (PDGF) (C), 10 ng/ml Tumor necrosis factor-alpha (TNF-α) (D); 10 ng/ml interleukin-1β (IL-1β) (E) and 30 ng/ml stromal derived factor 1-alpha (SDF-1α) (F), for 5 days, stained with STRO-1 mAb. (FIG. 9). These factors were found to greatly enhance the number of number of STRO-1$^{bri}$ MPC in vitro.

Figure 10:
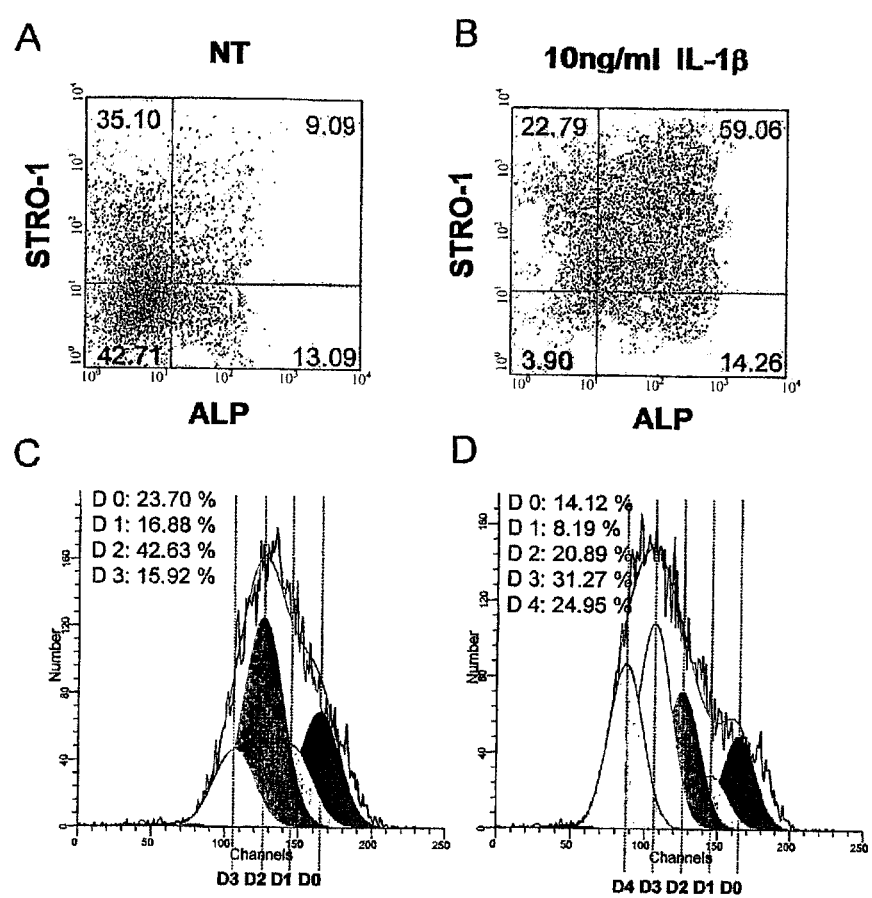
FIG. 10. IL-1β increases the proliferative potential of cells expanded from MPC. Cells were labelled with CFSE as described in the methods. Cells were subsequently cultured in the presence of 10 ng/ml IL-1β for 5 days, stained with STRO-1 and ALK PHOS mAb and analysed as described above. (A) non-treated (NT) and (B) IL-1β-treated cultures display an increase in the number of STRO-1$^{bri}$/ALP positive cells. This increase in STRO-1 expression is accompanied by an increase in cell proliferation as shown in (C) where untreated cultures have undergone four cell divisions, whilst (D) IL-1β treated cultures exhibit an increase in the number of cell divisions by increasing the number of STRO-1$^{bri}$ osteoprogenitor cells. The results displayed are a representative example of 3 independent experiments. Similar results were also obtained 1,25D, PDGF-BB, TNF-α, IL-1β, and SDF-1α were used to stimulate MPCs.

To investigate the mechanisms of how these factors enhanced the percentage of STRO-1$^{bri}$ expressing cells following ex vive expansion, cultured Stro-1$^{bri}$ were labelled with CFSE as described in the method then exposed to the various factors. FIG. 10 shows a representative experiment, where IL-1β increased the proliferative potential of MPC labelled with CFSE as described in the methods. Cells were cultured in the presence of 10 ng/ml IL-1β for 5 days, stained with STRO-1 mAb and analysed as described above. IL-1β was found to enhance the number of MPC divisions by increasing the number of bright STRO-1$^+$ osteoprogenitor cells. Similar results were also obtained 1,25D, PDGF-BB, TNF-α, IL-1β, and SDF-1α were used to stimulate MPCs.

Figure 11:
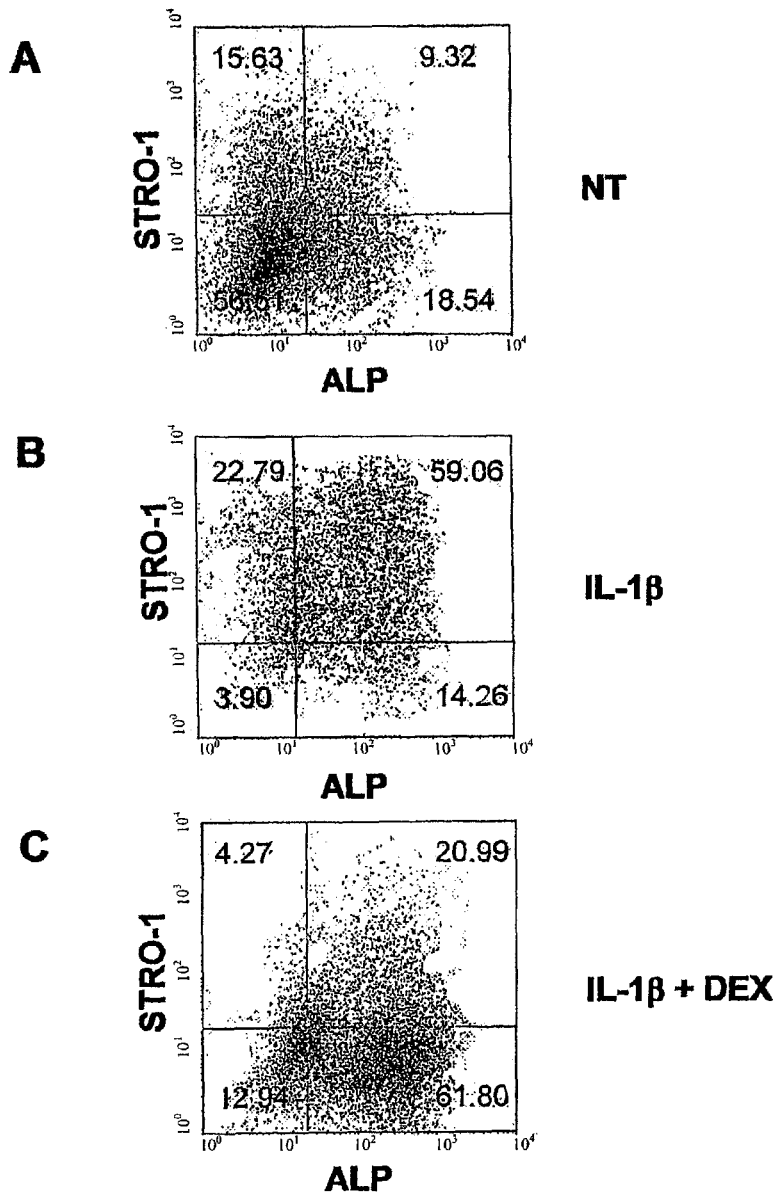
FIG. 11. IL-1β stimulates MPC proliferation and enhances their bone forming potential in the presence of the osteoinductive agent, dexamethasone. Human (A) ex vivo expanded progeny of MPC were seeded in 96-well plates at a cell density of 2,000 cells/well and cultured in α-MEM-10. Cultures were supplemented with IL-1β at the indicated concentrations and the cell number and viability quantitated at d7 using WST-1, as described in the methods. IL-1β at concentration 0.01 ng/ml significantly increased cell number to 136.6±1.2% of untreated control cultures (D, P=0.000003, Student t-test). A plateau effect was achieved at concentrations greater than 0.1 ng/ml. Values represent means±SEM of triplicate cultures of each concentration. (B & C) Ex vivo expanded progeny of MPC were seeded into 24-well plates at a cell density of $5\times10^4$/well in triplicate, and cultured in osteoinductive conditions, as described in the methods. The cells were treated with IL-1β at a concentration 10 ng/ml and cultures were "fed" weekly with fresh medium containing IL-1β. The release of free calcium from the matrix was achieved by treating the adherent cell layers under acidic condition as described in the methods. Samples were reacted with o-cresol-phthalein-complexon and the colorimetric reaction was read at 570 nm. The absolute calcium concentration was determined according to a standard curve for calcium. The results showed that mineral deposition was increased in cells treated with IL-1β (C) compared to untreated cells (B). The calcium level in IL-1β treated cells was significantly higher than that in untreated cells at both week 4 (P=0.00009, Student t-test) and week 6 (P=00004, Student t-test) (D). The results displayed are a representative example of 3 independent experiments, using stromal cells derived from three different donors.

Example 5: Increasing Proliferation of Stro-1$^{bri}$ Cells Also Increases the Number of Stro-1$^{dim}$ Cells The ability to enhance the proportion of STRO-1$^{bri}$ cultured MPC in the presence of various factors also correlated with an increase in the number of Stro-1$^{dim}$ cells. For example STRO-1$^{bri}$/Alk Phos$^+$ cells (FIG. 10B) a phenotype consistent with pre-osteoblastic cells (Gronthos et al., J Bone Miner Res. 14: 47-56, 1999; Pan et al., Bone 34(1): 112-23, 2004). We therefore examined whether this change in phenotype also correlated with an increased capacity of the induced STRO-1$^{bri}$ MPC to differentiate into bone forming cells, osteoblasts. FIG. 11 shows that IL-1β not only stimulated STRO-1 positive MPC proliferation, but also enhanced their bone forming potential in the presence of the osteoinductive agent, dexamethasone. IL-1β at concentration 0.01 ng/ml significantly increased MPC number to 136.6±1.2% of untreated control cultures (FIG. 11A). A plateau effect was achieved at concentrations greater than 0.1 ng/ml. Ex vivo expanded progeny of MPC were seeded into 24-well plates in the presence of osteoinductive conditions, as described in the methods. The cells were also treated with IL-1β at a concentration 10 ng/ml and cultures were "fed" weekly with fresh medium containing IL-1β. The absolute extracellular matrix calcium concentration was determined according to the methods. The results showed that mineral deposition was increased in cells treated with IL-1β (FIG. 11C) compared to untreated cells (FIG. 11B). The calcium level in IL-1β treated cells was significantly higher than that in untreated cells at both week 4 and week 6.

Figure 12:
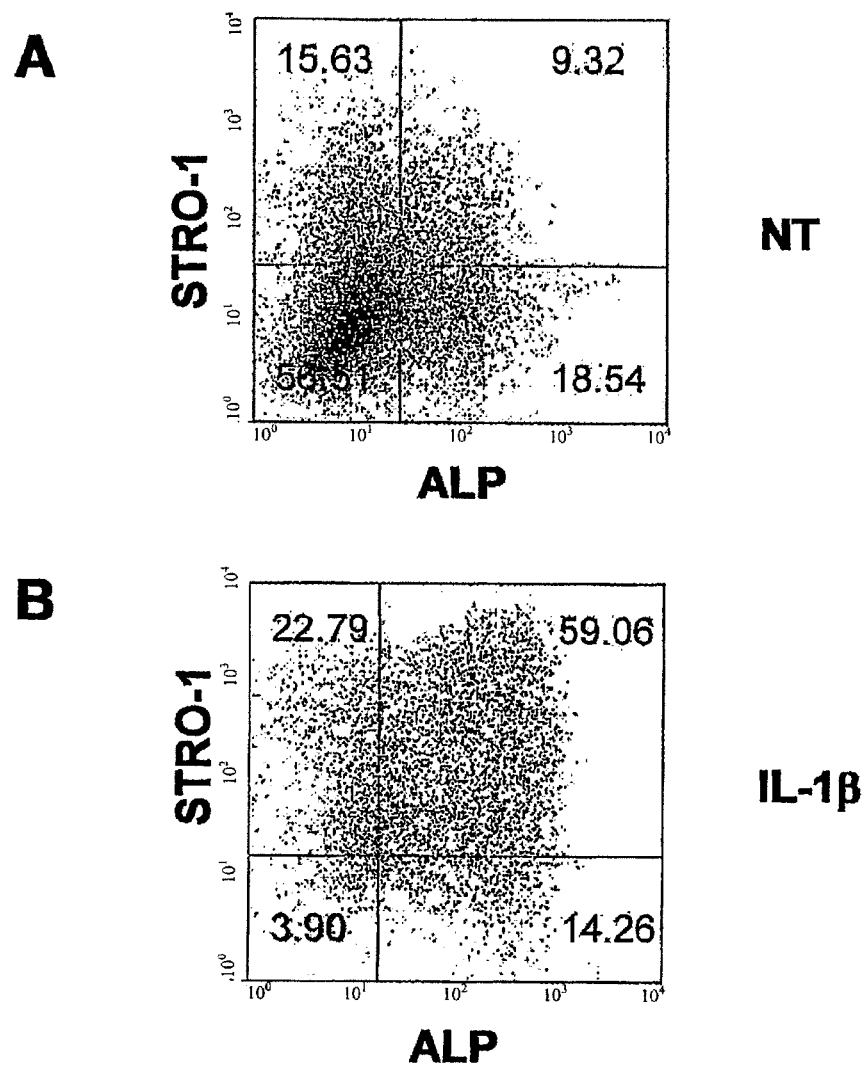
FIG. 12. IL-1β stimulates the proliferation and STRO-1$^{bri}$ MPC, whilst dexamethasone induces alkaline phosphatase (ALP) expression. Established cultures of human MPC were seeded in a 24-well plate at a cell density of $3\times10^4$/well in complete medium supplemented with (A) nothing (NT), (B) 10 ng/ml IL-1β or (C) $1\times10^{-8}$M Dexamethasone and (D) 10 ng/ml IL-1β and $1\times10^{-8}$M Dexamethasone. Cells were cultured for 21 days as described in the methods. The results suggest that the mitogenic action of IL-1β serves to increase the number of STRO-1$^{bri}$ MPC (B), which in turn stimulates the proliferation of the STRO-1$^{dim}$ cells (Refer FIG. 6). In addition, MPC acquire the expression of ALP in response to the FCS and ascorbate-2-phosphate present in the growth medium which is enhanced in response to the glucocorticosteroid, dexamethasone (dex) (D). The combined action of IL-1β and dex serve to enhance bone formation as seen in FIG. 11. The experiments were performed three times and a similar trend was observed in MPC derived from three different donors.
Figure 12:
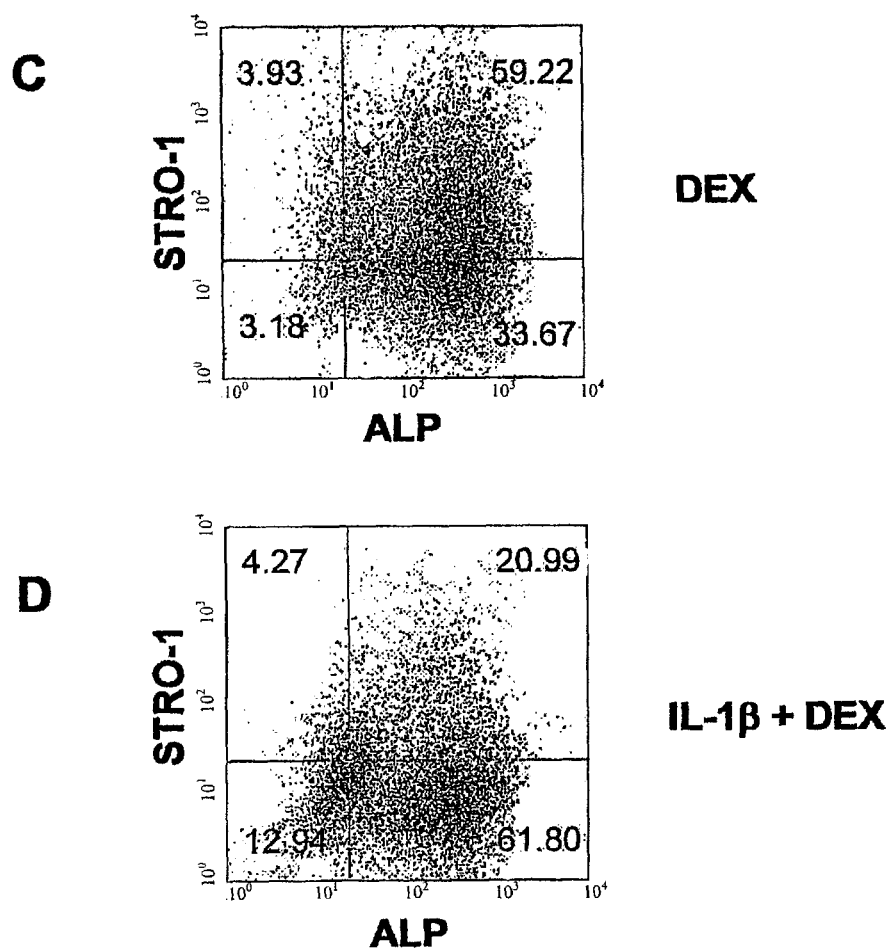
Figure 13:
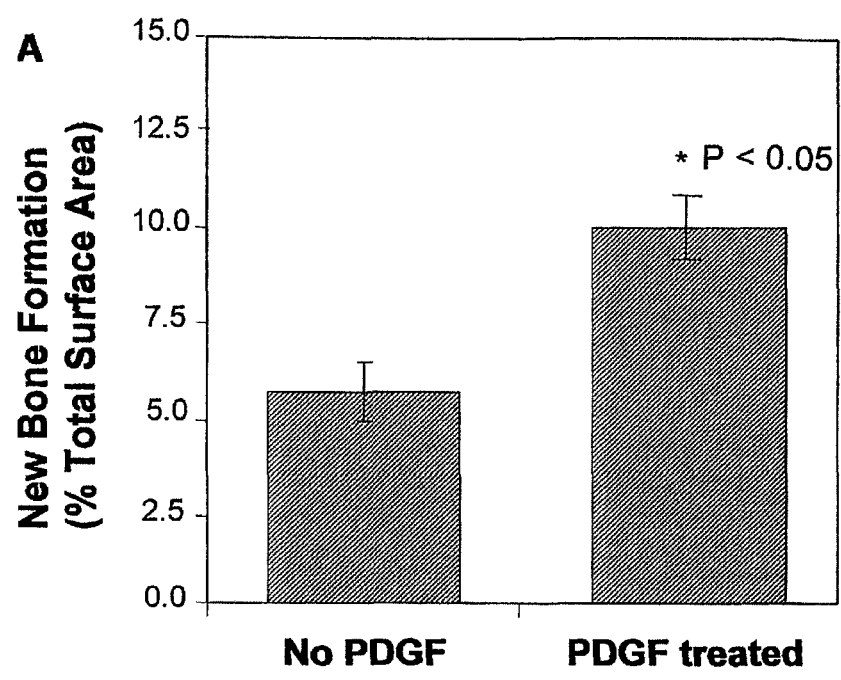
FIG. 13. Effect of PDGF on Bone Formation In Vivo. Semi-confluent secondary cultures of ex vivo expanded cells, derived from STRO-1$^{bri}$/VCAM-1$^+$ sorted bone marrow cells, were cultured in the presence or absence of PDGF-BB (10 ng/ml) for five days. Single cell suspensions were generated by trypsin/EDTA digest then incubated with 40 mg of hydroxyapetite/tricalcium phosphate particles (HA/TCP) for implantation into immunocompromised mice as described in the methods. After eight weeks, the harvested transplants were fixed and processed for histological examination. Analysis of new bone formation was determined using Scion Imaging software per surface area (20×) from three replicate transplants (A). Cultures pre-treated with PDGF-BB demonstrated significantly (*; p<0.05; t-test) more ectopic bone formation when compared to control untreated cultures. Typical images are shown depicting haematoxylin/eosin stained ectopic bone in cross-sections representative of untreated (B) and PDGF treated (C) transplants.
Figure 13:
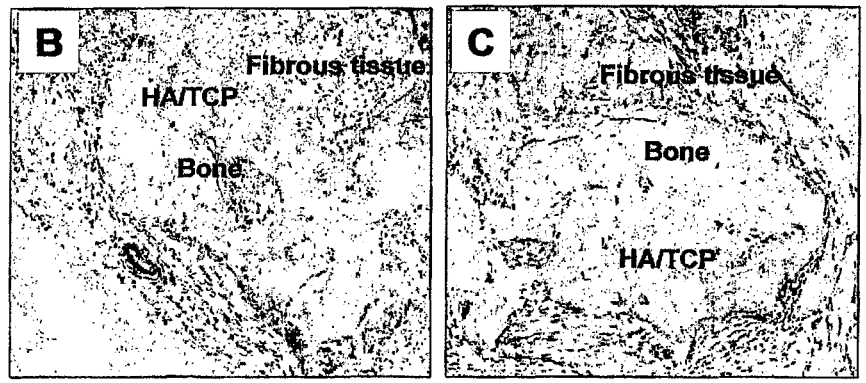

Data presented in FIG. 12 suggests that IL-1β stimulated the proliferation and STRO-1$^{Bri}$ MPC, resulting in an expansion of oetoprogenitors, whilst later addition of a secondary differentiation agent, dexamethasone, induced alkaline phosphatase (ALP) expression and loss of STRO-1 expression effectively enhancing the number of functional osteoblasts in vitro. The concept that, different factors can expand and regulate the STRO-1$^{Bri}$ MPC population was further tested in vivo. Semi-confluent secondary cultures of ex vivo expanded from Stro-1$^{bri}$ MPC, were cultured in the presence or absence of PDGF-BB (10 ng/ml) an additional factor known to enhance the number of ex viva expanded STRO-1$^{Bri}$ MPC (please refer to FIG. 9C). PDGF-induced and non-induced cell preparations were subsequently co-transplanted with hydroxyapetite/tricalcium phosphate particles (HA/TCP) into immunocompromised mice as described in the methods. After eight weeks, examination of the harvested transplants showed that cultures pre-treated with PDGF-BB exhibited significantly more ectopic bone formation (FIG. 13C) when compared with untreated control cultures (FIG. 13B) as quantitated by Scion Imaging (FIG. 13A).

Example 6: Purified Human BMSSCs Express High Levels of SDF-1

Figure 14:
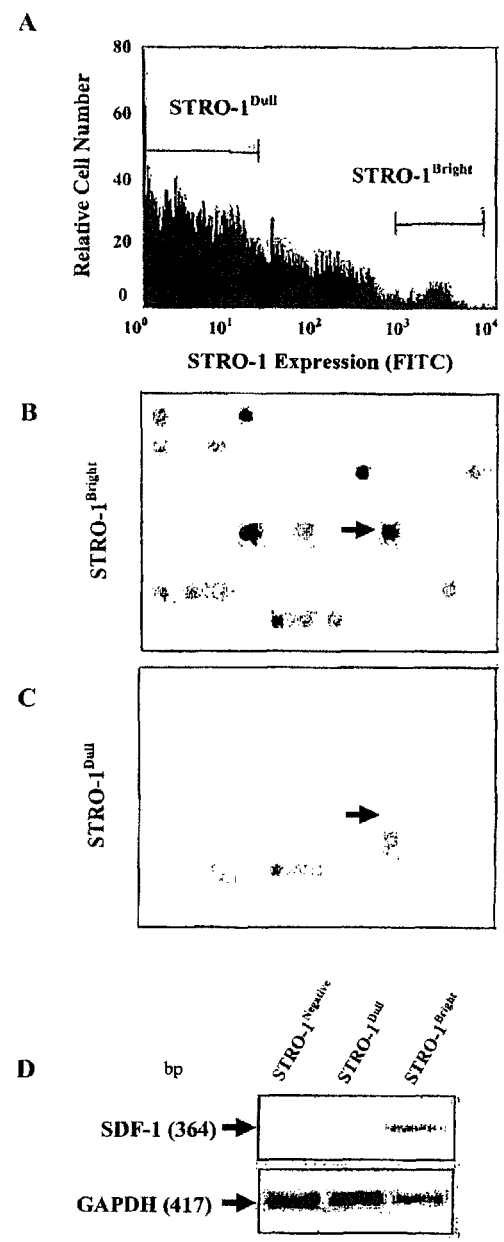
FIG. 14. BMSSCs express high levels of SDF-1. (A) MACS-isolated preparations of STRO-1$^+$ BMMNCs were partitioned into different STRO-1 subsets according to the regions, STRO-1$^{bright}$ and STRO-1$^{dull}$ using FACS. Total RNA was prepared from each STRO-1 subpopulation and used to construct a STRO-1$^{bright}$ subtraction hybridization library as described in "Materials and methods." (B-C) Replicate nitrocellulose filters, which have been blotted with representative PCR products amplified from bacterial clones transformed with STRO-1$^{bright}$ subtracted cDNA. The filters were then probed with either [$^{32}$P] deoxycytidine triphosphate (dCTP)-labeled STRO-1$^{bright}$ (B) or STRO-1$^{dull}$ (C) subtracted cDNA. The arrows indicate differential expression of 1 clone containing a cDNA fragment corresponding to human SDF-1. (D) Reverse transcriptase (RT)-PCR analysis demonstrating the relative expression of SDF-1 and glyceraldehyde-3-phosphate dehydrogenase (GAPDH) transcripts in total RNA prepared from freshly MACS/FACS-isolated BMMNC STRO-1 populations prior to culture, bp indicates base pair.

Subtractive hybridization has previously been used to increase the frequency of differentially expressed genes in rare cell populations (Xu et al., Cancer Res. 60: 1677-1682, 2000; Kingsley et al., Dev Growth Differ. 43: 133-143, 2001). In the present study, STRO-1$^{dull}$ (glycophorin-A$^+$ nucleated red cells) and the minor fraction of STRO-1$^{bright}$-expressing marrow cells (which includes all colony-forming BMSSCs) were isolated, using a combined MACS/FACS procedure as previously described (Gronthos et al. J Cell Sci. 116: 1827-1835, 2003) (FIG. 14A). For each sorted STRO-1 population, total RNA was prepared from 5 individual bone marrow donors and pooled. Following first-strand synthesis, STRO-1$^{bright}$ and STRO-1$^{dull}$ cDNA was subjected to a series of subtractive hybridization steps as described in "Materials and methods." To identify genes uniquely expressed by STRO-1$^{bright}$ BMSSC population, STRO-1$^{bright}$-subtracted cDNA was used to construct replicate low-density microarray filters comprising 200 randomly selected bacterial clones transformed with the STRO-1$^{bright}$ subtracted cDNAs ligated into a T/A cloning vector. The microarrays were subsequently probed with either [$^{32}$P] dCTP-labeled STRO-1$^{bright}$ or STRO-1$^{dull}$ subtracted cDNA (FIG. 14B-C). Differential screening identified a total of 44 clones, which were highly differentially expressed between the STRO-1$^{dull}$ and STRO-1$^{bright}$ subpopulations. DNA sequencing of all the differentially expressed clones revealed that only 1 clone was representative of a known stromal cell mitogen; namely, platelet-derived growth factor (PDGF) (Gronthos and Simmons, Blood. 85: 929-940, 1995). Interestingly, 6 of the 44 clones were found to contain DNA inserts corresponding to the chemokine, stromal-derived factor-1 (SDF-1). The high abundance of SDF-1 transcripts in human BMSSCs was confirmed by semiquantitative RT-PCR of total RNA prepared from freshly sorted STRO-1$^{bright}$, STRO-1$^{dull}$, and STRO-1$^{negative}$ bone marrow subpopulations (FIG. 14D).

Figure 15:
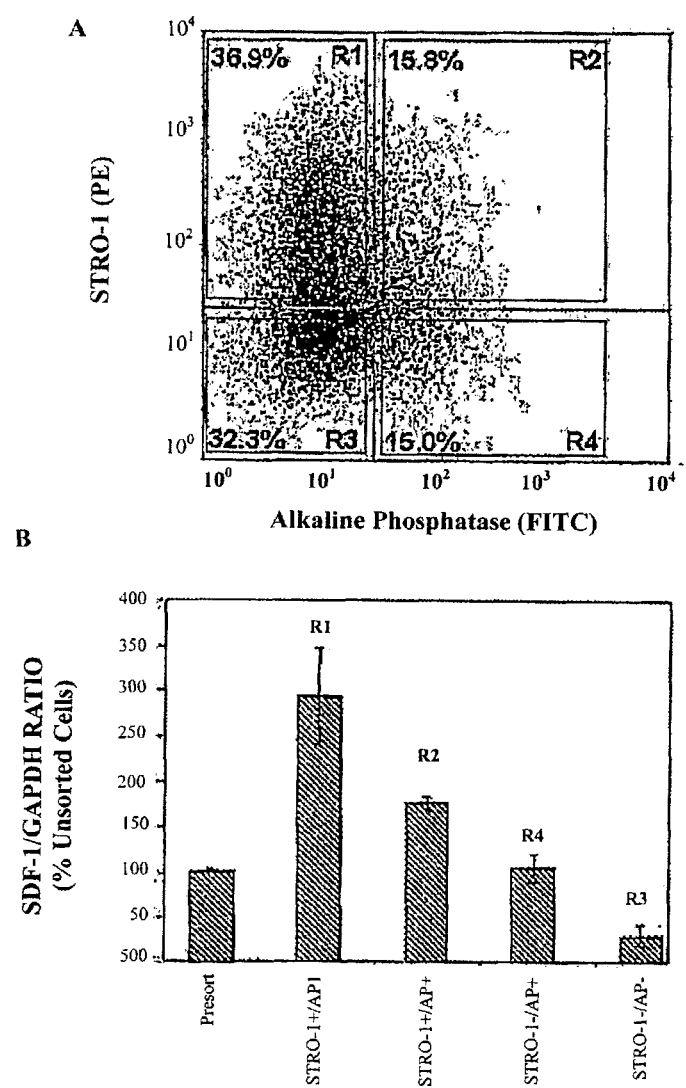
FIG. 15. Immature BMSSCs express higher levels of SDF-1 than more mature populations. (A) The dot plot represents dual flow cytometric analysis of single-cell suspensions of ex vivo-expanded BMSSCs examining cell surface expression of STRO-1 and AP antigens following culture in standard media. The different sorted STRO-1/AP subpopulations were isolated by FACS according to the sorting regions R1, R2, R3, and R4. (B) The graph depicts semiquantitative RT-PCR analysis of the relative expression of SDF-1 compared with the house keeping gene GAPDH, in total RNA prepared from unsorted and FACS-isolated cultured BMSSC populations according to their cell surface expression of STRO-1 and AP. The most immature osteogenic precursor population (STRO-1$^+$/AP$^-$) expressed higher levels than preosteoblasts (STRO-1$^+$/AP$^+$), followed by more mature osteoblast (STRO-1$^-$/AP$^+$) and osteocyte (STRO-1$^-$/AP$^-$) populations. The data represent the mean values±standard errors of 2 independent experiments, using secondary BMSSC cultures established from 2 different healthy bone marrow donors.

Example 7: SDF-1 is Preferentially Expressed by Immature Stromal Populations In Vitro We next examined whether the expression of SDF-1 was correlated to the developmental stage of BMSSCs in vitro. SDF-1 expression levels were assessed in different stromal populations by using an established in vitro model of osteogenic differentiation, based on the cell surface expression of STRO-1 and alkaline phosphatase (AP) (Gronthos et al., J Bone Miner Res. 14: 47-56, 1999; Stewart et al., J Bone Miner Res. 14: 1345-1356, 1999; Pan et al., Bone. 34(1): 112-23, 2004). Dual-color FACS was used to partition the different BMSSC STRO-1/AP subfractions according to the sorting regions (R1-R4) depicted in FIG. 15A. Each STRO-1/AP subfraction was double sorted to obtain more than 99.9% purity. Semiquantative RT-PCR examining SDF-1 expression was subsequently performed on total RNA isolated from each STRO-1/AP sorted population. The analysis revealed that the most immature stromal population STRO-1$^+$/AP$^-$ (osteoprogenitors) followed by STRO-1$^+$/AP$^+$ (preosteoblasts) expressed higher levels of SDF-1 in comparison to the most mature cell populations, STRO-1$^-$/AP$^+$ (osteoblasts) and STRO-1$^-$/AP$^-$ (osteocytes, bone lining cells) when normalized to the housekeeping gene GAPDH (FIG. 15B).

Figure 16:
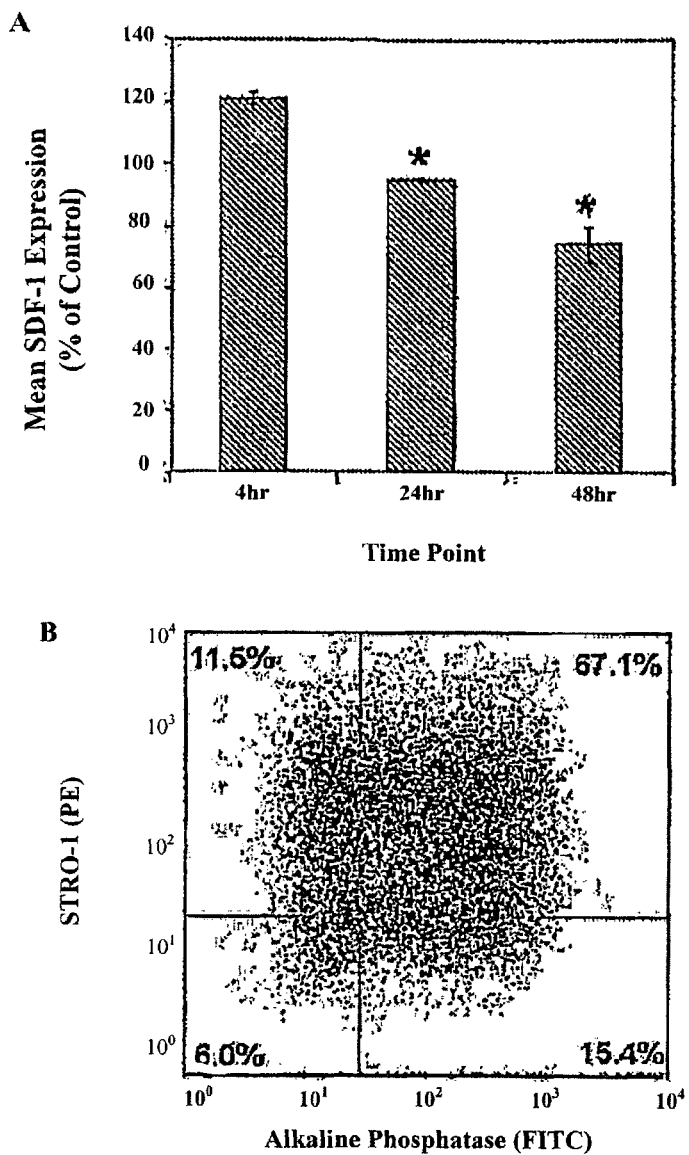
FIG. 16. SDF-1 is down-regulated by BMSSCs following osteoinduction. (A) Semiquantitative RT-PCR of SDF-1 expression relative to GAPDH by cultured BMSSCs in the presence of osteoinductive media over time. The mean values±standard errors represent 4 independent experiments. Osteoinductive conditions versus the corresponding controls were analyzed using paired t test at each time point with a significance value (*) of P<0.05. (B) The dot plot represents dual-colour flow cytometric analysis of single-cell suspensions of ex vivo-expanded BMSSCs, cultured for 48 hours in the presence of osteogenic induction media, based on the cell surface expression of STRO-1 and alkaline phosphatase antigens.

In parallel experiments, secondary cultures of BMSSCs, supplemented with osteogenic inductive media (supplemented with L-ascorbate-2-phosphate, dexamethasone, and inorganic phosphate), demonstrated a decrease in SDF-1 expression in a time-dependent manner (FIG. 16A). The data revealed that lower levels of SDF-1 expression were correlated with a higher proportion of preosteoblast-like cells (STRO-1$^+$/AP$^+$), following 48 hours of stimulation with osteogenic induction medium (FIG. 16B).

Example 8: BMSSCs Express the SDF-1 Receptor, CXCR4

Figure 17:
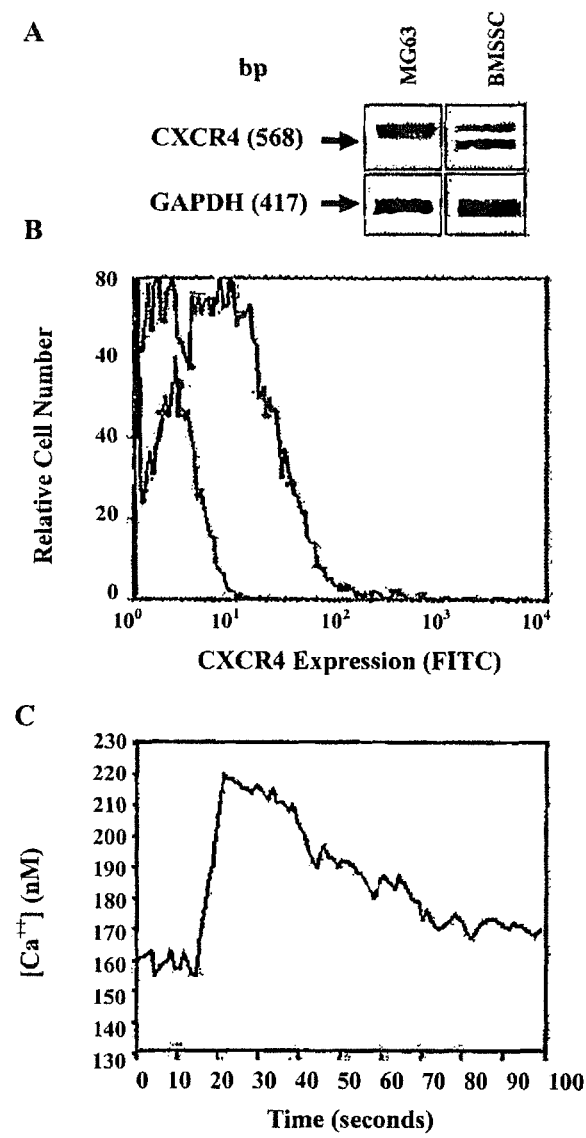
FIG. 17. BMSSCs express functional SDF-1 receptors. (A) RT-PCR analysis demonstrating the relative expression of CXCR4 and GAPDH transcripts in total RNA isolated from either primary BMSSC cultures or the human osteosarcoma cell line, MG63. (B) Single-cell suspensions of cultured BMSSCs were incubated with either a mouse anti-human CXCR4 antibody or the isotype-matched control antibody, 1A6.11 followed by a goat anti-mouse IgG$_1$ FITC-conjugated antibody. A representative histogram depicts the level of cell surface expression of CXCR4 (solid line) by BMSSCs relative to the control samples (dotted line) as assessed by flow cytometric analysis. (C) The graph demonstrates the levels of intracellular calcium measured in primary BMSSC cultures over time following the addition of human recombinant SDF-1α (30 ng/mL).

To determine whether SDF-1 could act as an autocrine factor, preliminary experiments using RT-PCR analysis confirmed that BMSSCs did in fact express the SDF-1 receptor, CXCR4 (FIG. 17A). Examination of CXCR4 expression by normal cultured BMSSCs and the human osteosarcoma cell line, MG63, revealed varying expression of the expected 568 base pair PCR product and a second, larger band. DNA sequence analysis confirmed the lower band as corresponding to the normal human CXCR4 isoform, while the larger band corresponded to a previously reported alternative splice variation (Gupta and Pillarisetti, J Immunol. 163: 2368-2372, 1999). BMSSCs were also shown to constitutively express low levels of CXCR4 protein at the cell surface as shown by flow cytometric analysis (FIG. 17B). Calcium mobilization studies were carried out to determine whether CXCR4 expressed by BMSSCs were functionally active. FURA-2-loaded BMSSCs were challenged with 30 ng/mL recombinant human SDF-1α (rhSDF-1α), resulting in a rapid and robust increase in intracellular calcium levels characteristic of SDF-1/CXCR4 signaling (FIG. 17C).

Example 9: Overexpression of SDF-1 Enhances the Potential of BMSSCs to Form Ectopic Bone In Vivo To determine whether SDF-1 had any functional role in stromal cell development, retroviral expression constructs containing the full-length human SDF-1 cDNA were used to transfect the packaging cell line PT67 as described in "Materials and methods." Harvested supernatant containing infectious particles were then used to generate stable, multicolony-derived BMSSC cell lines expressing high levels of SDF-1α and corresponding control cell lines transduced with empty pLNCX2 vector (FIG. 18A).

Figure 18:
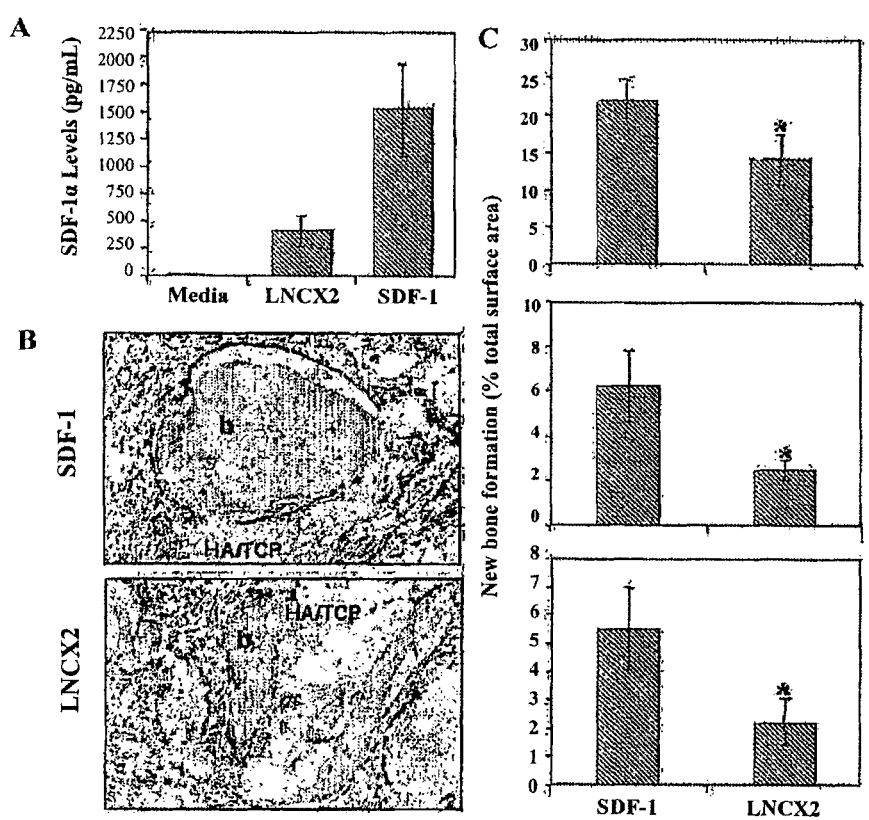
FIG. 18. Enforced SDF-1 expression by BMSSCs enhances their osteogenic potential (A) The retroviral packaging line PT67 was used to transduce secondary BMSSC cultures, derived from 3 different bone marrow aspirates, with a pLNCX2 construct containing either human SDF-1 cDNA or vector alone. Stable multicolony-derived high SDF-1-expressing BMSSCs and corresponding control lines were generated after G418 selection. Triplicate samples of tissue culture supernatant were assessed for SDF-1α levels using a commercially available ELISA kit. The data represent the mean values±standard errors generated from 3 different high SDF-1-expressing BMSSC cell lines versus the corresponding controls. (B) Single-cell suspensions of each of the transduced BMSSC lines were mixed with hydroxyapatite (HA/TCP) particles and then implanted subcutaneously into NOD/SCID mice. The images represent cross-sections of 8-week-old harvested transplants of new bone (b) formed by high SDF-1-expressing BMSSCs (SDF-1) and control cell lines (LNCX2) stained with hematoxylin & eosin (×200). Images were captured with an Olympus BX50 light microscope (Olympus, Tokyo, Japan) equipped with an Olympus D11 digital camera. Magnification ×200. (C) Each graph represents a different high SDF-1-expressing BMSSC line and corresponding control cell line derived from 3 different bone marrow donors. The level of new bone formation is expressed as a percentage of the total tissue surface area analyzed from 12 representative tissue sections, using Scion Imaging software. The data represent the mean values±standard errors from duplicate transplants. Statistical differences (*) of P<0.05 between the SDF-1 high-expressing BMSSC lines and corresponding controls were determined using the unpaired t test.

Cell lines derived from 3 individual bone marrow aspirates were implanted into immunocompromised mice in combination with hydroxyapatite/tricalcium phosphate particles, as described in "Materials and methods." Scion Imaging analysis of histologic sections from the harvested implants showed significantly greater levels (P<0.05, t test) of ectopic bone formation per area in those transplants containing high SDF-1-expressing BMSSC lines in comparison to the vector controls (FIG. 18C).

Parallel studies were performed to identify potential mechanisms of the observed SDF-1-mediated enhanced bone formation capacity. Surprisingly, we failed to detect any statistical difference in the capacity of high SDF-1-expressing BMSCs to form mineralized deposits of hydroxyapatite in vitro above the vector control cell lines (data not shown). Furthermore, we failed to detect any consistent differences in the expression of various bone-associated genes (BMP2, BMP4, CBFA1, osterix, osteocalcin, alkaline phosphatase [AP]) between the high SDF-1-expressing and matched vector control BMSSC lines (data not shown), Collectively, these data suggested that SDF-1 imposed an indirect effect on bone formation in vivo.

Example 10: SDF-1 Mediates BMSSC Growth and Survival

We next examined the possibility that overexpression of SDF-1 may provide a growth or survival advantage to the transduced BMSSCs. This notion was supported by proliferation studies demonstrating that high SDF-1-expressing BMSSCs displayed a moderate but not significant increase in their growth capacity above that of the BMSSC vector control cell lines (FIG. 19A). Furthermore, BMSSC lines overexpressing SDF-1 also exhibited a greater resistance to the apoptosis-inducing effects of the inflammatory cytokine, IL-4, previously shown to inhibit the growth of BMSSCs in vitro (Gronthos and Simmons, Blood. 85: 929-940, 1995), as assessed by the trypan blue uptake method (FIG. 19B). In accordance with these findings, living cultures of overexpressing SDF-1 BMSSCs also showed decreased cell surface staining of the early apoptosis marker, annexin V, when challenged with IL-4 (FIG. 19C-D).

Comparative experiments were subsequently performed to determine the effects of exogenous SDF-1 on the growth of normal BMSSCs. Purified STRO-1-positive bone marrow cells were cultured under serum-deprived conditions, previously shown to enhance the formation of the earliest identifiable mesenchymal precursor cells, (CFU-F; fibroblastic colony-forming unit), in the presence of PDGF-BB to levels comparable to serum-replete cultures (Gronthos et al. J Cell Sci. 116: 1827-1835, 2003; Gronthos and Simmons, Blood. 85: 929-940, 1995). While exogenous rhSDF-1α showed no inherent ability to stimulate colony production alone, an increase in CFU-F number was observed in combination with PDGF-BB (FIG. 20). Moreover, addition of the known potent CFU-F inhibitor, α-interferon 2a (Gronthos and Simmons, Blood. 85: 929-940, 1995; Wang et al., Am J Hematol. 40: 81-85. 1992) demonstrated a typical decline in PDGF-BB-induced colony formation, which was shown to be partially reversible in the presence of SDF-1. The observed response in the presence of SDF-1 was found to be optimal at 30 ng/mL over a concentration range 0.1 to 100 ng/mL (FIG. 21). Collectively, these data suggest that SDF-1 plays a role in promoting the self-renewal and survival capacity of BMSSCs.

DISCUSSION

The present study demonstrates for the first time that the earliest detectable BMSSCs isolated directly from human bone marrow aspirates express high levels of SDF-1 prior to culture. We have previously reported that multipotential BMSSCs are localized within the bone marrow microenvironment among the perivascular cells of large blood vessels (Shi and Gronthos, J Bone Miner Res. 18: 696-704, 2003). These observations correspond with the published distribution pattern of SDF-1 in human bone marrow, where the highest levels of SDF-1 are expressed by cells that surround blood vessels, including periarterial regions and blood capillaries of the bone, and by some bone marrow stromal cells near the endosteum at sites of early myelopoiesis and B-lymphocyte development (Ponomaryov et al., J Clin Invest. 106: 1331-1339, 2000; Petit at al., Nat Immunol. 3: 687-694, 2002; Salvucci et al., Blood 99: 2703-2711, 2002). Importantly, mature osteogenic cell populations located at the bone surfaces, or osteocytes within the bone matrix, appear to lack SDF-1 expression in situ (Ponomaryov et al., J Clin Invest. 106: 1331-1339, 2000).

Previous work by Stewart et al (Stewart at al., J. Bone Miner Res. 14: 1345-1356, 1999) and our laboratory (Gronthos et al., J Bone Miner Res. 1999; 14: 47-56, 1999; Pan et al., Bone. 34(1):112-23, 2004) have shown that early preosteogenic cells exist in normal stromal cultures that express the mesenchymal stem cell marker, STRO-1; but lack the expression of the osteoblast-associated marker, alkaline phosphatase. Progression of these precursor cell populations toward a mature and functional osteoblastic phenotype correlates to the loss of STRO-1 expression and an acquisition of AP cell-surface expression (Gronthos et al., J Bone Miner Res. 1999; 14: 47-56, 1999; Stewart et al., J Bone Miner Res. 14: 1345-1356, 1999). Using this In vitro model of osteogenic cellular differentiation we have demonstrated that cultured BMSSC cells, representative of committed osteogenic populations, displayed decreased levels of SDF-1 when compared with more immature STRO-1$^+$ BMSSC fractions. Moreover, there was a significant diminution of SDF-1 expression following treatment of BMSSCs with osteogenic induction media, providing further evidence that high SDF-1 expression is linked with a more primitive, less committed stage of preosteogenic differentiation. Collectively, our data suggest that SDF-1 may act to localize primitive uncommitted BMSSC populations within their perivascular niche until required to proliferate and differentiate in response to environmental cues that may act to disrupt SDF-1/CXCR4 interactions.

While SDF-1 is thought to be critical in normal hematopoiesis, inflammation, and the metastasis of various tumors, little is known about the role of SDF-1 on the growth or differentiation of BMSSCs.

SDF-1 mediates its effects through its receptor, CXCR4, a transmembrane glycoprotein, belonging to the family of 0 protein-coupled molecules, where CXCR4 also acts as the main coreceptor for human immunodeficiency virus type-1 (Bleul et al., Nature 382: 829-833, 1996; Oberlin et al., Nature 382: 833-835, 1996; Ma et al., Proc Natl Acad Sci USA. 95: 9448-9453, 1998). Interestingly, we observed 2 CXCR4 splice variants both in normal cultured BMSSCs and the human osteosarcoma cell line, MG63. DNA sequence analysis confirmed the smaller splice variant to correspond to the normal human CXCR4 cDNA spanning exons 1 and 2, the abundant form found in normal BMSSCs. In contrast, the larger splice variant, found to be highly abundant in MG63 cells, corresponded to a previously described alternative splice variation, generated through the inclusion of transcribed DNA sequence from the intersecting intron, resulting in the addition of a further 9 amino acids (Gupta et al., J Immunol. 163: 2368-2372, 1999). Tissue distribution studies demonstrated that the smaller transcript was the predominant CXCR4 isoform found in normal tissues, while the larger transcript was highly expressed in various leukemic and carcinoma cell lines (Gupta et al., J Immunol. 163: 2368-2372, 1999). While both splice variants are active, the functional significance of the larger CXCR4 transcript has not yet been determined but may relate to the importance of SDF-1/CXCR4 in development as a mechanism to compensate for any errors that may occur in CXCR4 splicing during embryonic development.

In the present study, we demonstrated that BMSSCs constitutively expressed low cell-surface levels of functional CXCR4 protein as shown by flow cytometric analysis and calcium mobilization studies. Therefore, SDF-1/CXCR4 signaling may play a critical role in regulating BMSSC growth and migration.

In the present study we also showed that the majority of ex vivo-expanded BMSSCs begin to undergo partial osteogenic differentiation, which correlated with a decrease in SDF-1 expression. This maturation appeared to enhance the susceptibility of BMSSCs to factors that induce apoptosis. Our studies showed that BMSSC lines overexpressing SDF-1 exhibited increased protection against the apoptotic effects of IL-4, previously shown to inhibit the growth of BMSSCs in vitro (Gronthos and Simmons, Blood. 85: 929-940, 1995). Similar experiments demonstrated that high SDF-1-expressing BMSSC lines were more resistant to the induction of early apoptosis in the presence of IL-4.

The present study confirmed the survival and growth advantage conveyed by SDF-1 on the earliest identifiable mesenchymal precursor cells, freshly isolated STRO-1$^{bright}$ bone marrow cells that contain the CFU-F population. While exogenous rhSDF-1α showed no inherent ability to stimulate colony production alone, an increase in CFU-F number was observed when added in combination with PDGF-BB. The varied effect of SDF-1 on the growth rates between different BMSSC populations may be due to differences in the developmental stage of the freshly isolated primitive BMSSCs versus more mature ex vivo-expanded stromal cells. Therefore, PDGF and SDF-1 may act in synergy in promoting the self-renewal and survival capacity of BMSSCs.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 1

Antibodies used in this patent

| CELL TYPE | ANTIGEN | SOURCE ISOTYPE DILUTION |
|---|---|---|
| Skeletal Muscle | Myo D | Santa Cruz Rabbit Ig 1/50 |
| | Desmin | DAKO IgG1 10 ug/ml |
| Smooth Muscle | SMMHC | Sigma mIgG1 Acites 1/500 |
| | SMHC -FAST | Sigma mIgG1 10 ug/ml |
| | alphaSMAC | DAKO mIgG2a 10 ug/ml |
| | PDGF-R | Pharmigen mIgG 10 ug/ml |
| | Vimentin | DAKO mIgG1 10 ug/ml |
| Chondrocytes | Type II Collagen | Chemicon mIgG1 10 ug/ml |
| | Collagen IX | Chemicon mIgG2A 10 ug/ml |

TABLE 1-continued

Antibodies used in this patent

| CELL TYPE | ANTIGEN | SOURCE ISOTYPE DILUTION |
|---|---|---|
| | Aggrecan | Chemicon mIgG1 10 ug/ml |
| | Link Protein | DSHB mouse IgG2b 10 ug/ml |
| | S-100 | Chemicon rabbit Ig 1/100 |
| | Biglycan | Dr. Larry Fisher NIH RABBIT Ig 1/500 |
| Basal Fibroblasts | Laminin | Chemicon mIgG1 10 ug/ml |
| | Type IV Collagen | DAKO mIgG1 10 ug/ml |
| | Versican | DHSB 12C5 IgG1 10 ug/ml |
| Endothelial Cells | vWF | DAKO IgG1 mouse |
| | VCAM-1 | Chemicon IgG1 6G10 10 ug/ml |
| | Endoglin | BD IgG1 10 ug/ml |
| | MUC18 | In house CC9 IgG2a 10 ug/ml |
| | CD31 | DAKO IgG 10 ug/ml |
| | CD34 | DAKO mIgG1 10 ug/ml |
| | SDF-1 | R&D IgG1 10 ug/ml |
| Cardiomyocytes | calponin | Chemicon IgG1 10 ug/ml |
| | Troponin I | Accurate Chem and Sci Corp IgG1 10 ug/ml |
| | Troponin C | Chemicon mIgG2a 10 ug/ml |
| Neurons | NCAM | DAKO IgG2a 10 ug/ml |
| | GFAP | DAKO mIgG1 10 ug/ml |
| | Neuroanalase | DAKO RABBIT Ig 1/200 |
| | Neurofilament | OAKO IgG1 10 ug/ml |
| Bone | AP | DSHB mIgG1 10 ug/ml |
| | Type I Collagen | CHEMICON mouse IgG 10 ug/ml |
| | CBFA 1 | Alpha Diagnostic RABBIT Ig 1/200 |
| | OCN | Chemicon RABBIT Ig 1/200 |
| | OPG | R&D IgG2b 10 ug/ml |
| | RANKL | R&D IgG2a 10 ug/ml |
| | Annexin II | Santa Cruz RABBIT Ig 1/100 |
| Fat | CEPBalpha | Santa Cruz RABBIT Ig 1/200 |
| | PPARgamma | Santa Cruz RABBIT Ig 1/200 |
| | Leptin | Chemicon IgG 10 ug/ml |
| Epithelial Cells | Keratin 14 | DAKO mIgG 10 ug/ml |
| | Cytokeratin 10 + 13 | DAKO mIgG2a 10 ug/ml |
| | EGFR | Pharmingen mIgG 10 ug/ml |
| Fibroblast | Collagen III | Chemicon mIgG1 10 ug/ml |
| | NGFR | Santa Cruz mIgG1 10 ug/ml |
| | Fibroblast marker | SIGMA mIgG 10 ug/ml |
| Haematopoletic | CD14 | DAKO IgG2a 10 ug/ml |
| | CD45 | DAKO IgG1 10 ug/ml |
| | Glycophorin-A | DAKO IgG 10 ug/ml |

TABLE 2

RT-PCR primers and conditions for the specific amplification of human mRNA

| Target Gene | Sense/Antisense (5'-3') Primer Sequences | Product Size |
|---|---|---|
| GAPDH | CACTGACACGTTGGCAGTGG/ CATGGAGAAGGCTGGGGCTC | 417 |
| SDF-1 | GAGACCCGCGCTCGTCCGCC/ GCTGGACTCCTACTGTAAGGG | 364 |
| IL-1β | AGGAAGATGCTGGTTCCCTCTC/ CAGTTCAGTGATCGTACAGGTGC | 151 |
| FLT-1 | TCACTATGGAAGATCTGATTTCTTACAGT/ GGTATAAATACACATGTGCTTCTAG | 380 |
| TNF-α | TCAGATCATCTTCTCGAACC/ CAGATAGATGGGCTCATACC | 361 |
| KDR | TATAGATGGTGTAACCCGGA/ TTTGTCACTGAGACAGCTTGG | 450 |

TABLE 2-continued

RT-PCR primers and conditions for the specific amplification of human mRNA

| Target Gene | Sense/ Antisense (5'-3') Primer Sequences | Product Size |
|---|---|---|
| RANKL | AACAGGCCTTTCAAGGAGCTG/ TAAGGAGGGGTTGGAGACCTCG | 538 |
| Leptin | ATGCATTGGGAACCCTGTGC/ GCACCCAGGGCTGAGGTCCA | 492 |
| CBFA-1 | GTGGACGAGGCAAGAGTTTCA/ TGGCAGGTAGGTGTGGTAGTG | 632 |
| PPARγ2 | AACTGCGGGGAAACTTGGGAGATTCTCC/ AATAATAAGGTGGAGATGCAGGCTCC | 341 |
| OCN | ATGAGAGCCCTCACACTCCTC/ CGTAGAAGCGCCGATAGGC | 289 |
| MyoD | AAGCGCCATCTCTTGAGGTA/ GCGAGAAACGTGAACCTAGC | 270 |
| SMMHC | CTGGGCAACGTAGTAAAACC/ TATAGCTCATTGCAGCCTCG | 150 |
| GFAP | CTGTTGCCAGAGATGGAGGTT/ TCATCGCTCAGGAGGTCCTT | 370 |
| Nestin | GGCAGCGTTGGAACAGAGGTTGGA/ CTCTAAACTGGAGTGGTCAGGGCT | 460 |
| SOX9 | CTCTGCCTGTTTGGACTTTGT/ CCTTTGCTTGCCTTTTACCTC | 598 |
| Collagen type X | AGCCAGGGTTGCCAGGACCA/ TTTTCCCACTCCAGGAGGGC | 387 |
| Aggrecan | CACTGTTACCGCCACTTCCC/ ACCAGCGGAAGTCCCCTTCG | 184 |

TABLE 3

Summary of the Relative Gene Expression in STRO-1$^{Brl}$ and STRO-1$^{Dim}$ populations. A list of genes which displayed measurable and differential expression between the STRO-1$^{Brl}$ and STRO-1$^{Dim}$ populations as determined by reverse transcription-PCR are presented. Values represent the relative gene expression with reference to the house-keeping gene, GAPDH.

| Tissue | Marker | Gene Expression relative to GAPDH | |
|---|---|---|---|
| | | STRO-1$^{Brl}$ | STRO-1$^{Dim}$ |
| Neurons | GFAP (Glial Fibrillary Acidic Protein) | 0.1 | 0.7 |
| Bone | OCN (Osteocalcin) | 1.1 | 2.5 |
| | OSX (Osterix) | 0.4 | 1.3 |
| | CBFA-1 (Core Factor Binding Protein-1) | 0.3 | 0.6 |
| | RANKL (Receptor Activator of Nuclear Factor κ B) | 1.6 | 0.3 |
| Fat | Leptin | 3.1 | 4.2 |
| Cardiomyocytes | GATA-4 | 1.1 | 2.9 |
| Endothelial cells | Ang-1 (Angiopoietin-1) | 1.5 | 0.8 |
| | SDF-1-alpha (Stromal Derived factor-1-alpha) | 3.2 | 0.1 |
| Chondrocytes | Sox 9 | 0.3 | 1.1 |
| | COL X (Collagen X) | 3.5 | 2.8 |
| Pro-inflammatory Cytokines | TNF-alpha (Tumour necrosis alpha) | 1.7 | 0.9 |

TABLE 4

Summary of the Relative Protein Expression in STRO-1$^{Brl}$ and STRO-1$^{Dim}$ populations. A list of proteins which displayed differential expression between the STRO-1$^{Brl}$ and STRO-1$^{Dim}$ populations as determined by flow cytometry are presented. Values represent the relative mean fluorescence intensity of staining as described in FIG. 2.

| Tissue | Marker | Mean Fluorescence Intensity | |
|---|---|---|---|
| | | STRO-1$^{Brl}$ | STRO-1$^{Dim}$ |
| Neurons | Neurofilament | 1.7 | 20.5 |
| Bone | ALK PHOS (Alkaline Phophatase) | 5.7 | 44.5 |
| | RANKL (Receptor Activator of Nuclear Factor κ B) | 658.5 | 31.0 |
| Epithelial Cells | CytoKeratin 10 + 13 | 1.2 | 23.3 |
| | Cytokeratin 14 | 1.8 | 8.8 |
| Smooth Muscle | α-SMA (Alpha Smooth Muscle Actin) | 318.0 | 286.0 |
| Chondrocytes | Byglycan | 84.4 | 65.9 |
| Basal Fibroblast | Tenascin C | 22.2 | 6.9 |
| Cardiomyocyte | Troponin C | 2.5 | 15.0 |

The invention claimed is:

1. A method of increasing proliferation of STRO1$^{dim}$ cells, the method comprising: co-culturing:
   a) greater than 5% STRO1$^{bright}$ multipotent mesenchymal cells isolated from bone marrow mononuclear cells with
   b) STRO1$^{dim}$ cells isolated from bone marrow mononuclear cells
   such that proliferation of the STRO1$^{dim}$ cells is increased, wherein:
   i) the STRO1$^{bright}$ multipotent mesenchymal cells comprise a plurality of cells expressing VCAM1,
   ii) the STRO1$^{dim}$ cells comprise more committed precursor cell types than the STRO1$^{bright}$ multipotent mesenchymal cells,
   iii) the STRO1$^{bright}$ cells are more primitive than the STRO1$^{dim}$ cells, and
   iv) the STRO1$^{bright}$ cells emit at least a four-fold greater fluorescent signal than STRO1$^{dim}$ cells as determined by FACS analysis.

2. A method as claimed in claim 1, wherein the STRO1$^{dim}$ cells express CXCR4.

* * * * *